US007560263B2

(12) United States Patent
Kakkis et al.

(10) Patent No.: US 7,560,263 B2
(45) Date of Patent: Jul. 14, 2009

(54) COMPOSITIONS OF PROKARYOTIC PHENYLALANINE AMMONIA-LYASE AND METHODS OF TREATING CANCER USING COMPOSITIONS THEREOF

(75) Inventors: Emil D. Kakkis, Novato, CA (US); Michel C. Vellard, San Rafael, CA (US); Mubarack Muthalif, Novato, CA (US)

(73) Assignee: BioMarin Pharmaceutical Inc., Novato, CA (US)

( * ) Notice: Subject to any disclaimer, the term of this patent is extended or adjusted under 35 U.S.C. 154(b) by 0 days.

(21) Appl. No.: 12/107,731

(22) Filed: Apr. 22, 2008

(65) Prior Publication Data

US 2009/0047268 A1 Feb. 19, 2009

Related U.S. Application Data

(60) Provisional application No. 61/066,125, filed on Aug. 17, 2007.

(51) Int. Cl.
*C12N 9/88* (2006.01)
*A61K 38/00* (2006.01)

(52) U.S. Cl. .......................... 435/232; 530/345; 514/12

(58) Field of Classification Search .................. 435/232
See application file for complete search history.

(56) References Cited

U.S. PATENT DOCUMENTS

| | | | | |
|---|---|---|---|---|
| 4,252,822 | A | 2/1981 | Berry | |
| 4,562,151 | A | 12/1985 | Kishore | |
| 5,166,322 | A | 11/1992 | Shaw et al. | |
| 5,206,344 | A | 4/1993 | Katre et al. | |
| 5,690,929 | A | 11/1997 | Lishko et al. | |
| 5,753,487 | A | 5/1998 | Eigtved et al. | |
| 5,766,897 | A | 6/1998 | Braxton | |
| 5,981,239 | A | 11/1999 | Liu | |
| 6,057,292 | A | 5/2000 | Cunningham et al. | |
| 6,312,939 | B1 | 11/2001 | Roberts et al. | |
| 6,433,148 | B1 | 8/2002 | Abrahan et al. | |
| 6,451,986 | B1 | 9/2002 | Pettit | |
| 6,461,849 | B1 | 10/2002 | Olsen et al. | |
| 6,548,644 | B1 | 4/2003 | Pettit | |
| 6,586,398 | B1 | 7/2003 | Kinstler et al. | |
| 6,686,164 | B1 | 2/2004 | Olsen et al. | |
| 6,737,259 | B1 | 5/2004 | Clark | |
| 2002/0052038 | A1 | 5/2002 | Roberts et al. | |
| 2002/0102712 | A1 | 8/2002 | Yoshida et al. | |
| 2003/0082238 | A1 | 5/2003 | Babich et al. | |
| 2007/0048855 | A1 | 3/2007 | Gamez et al. | |
| 2008/0008695 | A1* | 1/2008 | Vellard et al. | 424/94.3 |
| 2009/0038023 | A1 | 2/2009 | Weiner et al. | |
| 2009/0047265 | A1 | 2/2009 | Kakkis et al. | |

FOREIGN PATENT DOCUMENTS

| | | |
|---|---|---|
| WO | WO 90/12874 | 11/1990 |
| WO | WO 03/072743 | 9/2003 |
| WO | WO 2004/044169 | 5/2004 |
| WO | WO 2006/034373 | 3/2006 |
| WO | WO 2008/006661 | 1/2008 |
| WO | WO 2008/069958 | 6/2008 |
| WO | WO 2008/153776 | 12/2008 |
| WO | WO 2009/025760 | 2/2009 |

OTHER PUBLICATIONS

Gura, Science, v278, 1997, pp. 1041-1042.*

Freshney, Culture of Animal Cells, A Manual of Basic Technique, Alan R. Liss, Inc., 1983, New York, p. 4.*

Dermer, Bio/Technology, 1994, vol. 12, p. 320.*

U.S. Appl. No. 11/451,999, filed Jun. 12, 2006, Vellard et al.

U.S. Appl. No. 12/107,736, filed Apr. 22, 2008, Kakkis et al.

U.S. Appl. No. 61/055,946, filed May 23, 2008, Fitzpatrick et al.

Abell et al., "The Effects of Phenylalanine Ammonia-Lyase on Leukemic Lymphocytes in Vitro," *Cancer Research*, 32:285-290 (1972).

Abell et al., "An In Vivo Evaluation of the Chemotherapeutic Potency of Phenylalanine Ammonia-Lyase," *Cancer Research*, 33:2529-2532 (1973).

Abell et al., "Phenylalanine Ammonia-Lyase from the Yeast *Rhodotorula glutinis*," *Methods in Enzymology*, 142:242-253 (1987).

Abrams et al., "Rational Antigen Modification as a Strategy to Upregulate of Downregulate Antigen Recognition," *Current Opinion Immunology*, 12:85-91 (2000).

Alunni et al., "Mechanisms of Inhibition of Phenylalanine Ammonia-Lyase by Phenol Inhibitors and Phenol/Glycine Synergistic Inhibitors," *Archives of Biochemistry and Biophysics*, 412:170-175 (2003).

Ambrus et al., "Phenylalanine Depletion for the Management of Phenylketonuria: Use of Enzyme Reactors with Immobilized Enzymes," *Science*, 201:837-839 (1978).

Ambrus et al., "Depletion of Phenylalanine in the Blood of Phenylketonuric Patients Using a PAL-Enzyme Reactor, an In Vitro Study," *Research Communications in Chemical Pathology and Pharmacology*, 37(1):105-111 (1982).

Ambrus et al., "In Vivo Safety of Hollow Fiber Enzyme-Reactors with Immobilized Phenylalanine Ammonia-Lyase in a Large Animal Model for Phenylketonuria," *The Journal of Pharmacology and Experimental Therapeutics*, 224(3):598-602 (1983).

Ambrus et al., "Extracorporeal Enzyme Reactors for Depletion of Phenylalanine in Phenylketonuria," *Annals of Internal Medicine*, 106:531-537 (1987).

(Continued)

*Primary Examiner*—Suzanne M. Noakes
(74) *Attorney, Agent, or Firm*—Jones Day

(57) ABSTRACT

The present invention is directed to phenylalanine ammonia-lyase (PAL) variants produced by prokaryotes, wherein such prokaryotic PAL variant has a greater phenylalanine-converting activity and/or a reduced immunogenicity as compared to a wild-type PAL. The invention provides compositions of prokaryotic PAL and biologically active fragments, mutants, variants or analogs thereof, as well as methods for the production, purification, and use of such compositions for therapeutic purposes, including the treatment of cancer.

26 Claims, 26 Drawing Sheets

OTHER PUBLICATIONS

Baedeker et al., "Structures of two Histidine Ammonia-Lyase Modifications and Implications for the Catalytic Mechanism," *European Journal of Biochemistry*, 269:1790-1797 (2002).
Becker et al., "Cloning, Sequencing, and Biochemical Characterization of the Nostocyclopeptide Biosynthetic Gene Cluster: Molecular Bases for Imine Macrocyclization," *Gene*, 325:35-42 (2004).
Bezanson et al., "Biosynthesis of Cinnamamide and Detection of Phenylalanine Ammonia-Lyase in *Streptomyces verticillatus," Canadian Journal of Microbiology*, 16:147-151 (1970).
Billett et al., "A Specific and Reversible Macromolecular Inhibitor of Phenylalanine Ammonia-Lyase and Cinnamic Acid-4-Hydroxylase in Gherkins," *Biochim. Biophys. Acta.*, 524:219-230 (1978).
Bourget et al., "Artificial Cell-Microencapsulated Phenylalanine Ammonia-Lyase," *Applied Biochemistry and Biotechnology*, 10:57-59 (1984).
Bourget et al., "Phenylalanine Ammonia-Lyase Immobilized in Semipermeable Microcapsules for Enzyme Replacement in Phenylketonuria," *Federation of European Biochemical Societies Letters*, 180(1):5-8 (1985).
Bourget et al., "Phenylalanine Ammonica-Lyase Immobilized in Microcapsules for the Depletion of Phenylalanine in Plasma in Phenylketonuric Rat Model," *Biochimica et Biophysica Acta*, 883:432-438 (1986).
Brannigan et al., "Protein Engineering 20 Years On," *Nature Reviews, Molecular Cell Biology*, 3:964-970 (2002).
Calabrese et al., "Crystal Structure of Phenylalanine Ammonia-Lyase: Multiple Helix Dipoles Implicated in Catalysis," *Biochemistry*, 43(36):11403-11416 (2004).
Chang et al., "A New Theory of Enterorecirculation of Amino Acids and Its Use for Depleting Unwanted Amino Acids Using Oral Enzyme-Artificial Cells, as in Removing Phenylalanine in Phenylketonuria," *Art. Cells Blood Subs. and Immob. Biotech.*, 23(1):1-21 (1995).
Chang et al., "Procedures for Micorencapsulation of Enzymes, Cells and Genetically Engineered Microorganisms," *Molecular Biotechnology*, 17:249-260 (2001).
Chen et al., "Tuning the Activity of an Enzyme for Unusual Environments: Sequential Random Mutagenesis of Subtilisin E for Catalysis in Dimethylformamide," *Proc. Natl. Acad. Sci. U.S.A.*, 90:5618-5622 (1993).
Chi et al., "Physical Stability of Proteins in Aqueous Solution: Mechanism and Driving Forces in Nonnative Protein Aggregation," *Pharmaceutical Research*, 21(6):1325-1336 (2003).
Chirino et al., "Minimizing the Immunogenicity of Protein Therapeutics," *Drug Discovery Today*, 9(2):82-90 (2004).
Christiansen et al., The Role of the MoFe protein alpha-125-Phe and beta-125-Phe Residues in *Aztobacter Vinelandii* MoFe-Fe Protein Interaction, *Journal of Inorganic Biochemistry*, 80:195-204 (2000).
D'Agostino, "Tetrahydrobiopterin and Mild Phenylketonuria," *New England Journal of Medicine*, 348:1723-1724 (2003).
Da Cunha, "Purification, Characterization and Induction of L-Phenylalanine Ammonia-Lyase in *Phaseolus Vulgaris," European Journal of Biochemistry*, 178:243-248 (1988).
Davis. "Mimicking Posttranslational Modifications of Proteins," *Science*, 303:480-482 (2004).
Delgado et al., "The Uses and Properties of PEG-Linked Proteins," *Critical Reviews in Therapeutic Drug Carrier Systems*, 9(3-4):249-304 (1992).
Dengler, et al., "Development of a Propidium Iodide Fluorescence Assay for Proliferation and Cytotoxicity Assays," *Anti-Cancer Drugs*, 6:522-532 (1995).
Egrie et al., "Development and Characterization of Novel Erythropoiesis Stimulating Protein (NESP)," *British Journal of Cancer*, 84(Suppl. 1):3-10 (2001).
Elstad et al., "Modulation of B16-B16 Murine Melanoma Metastatic Phenotype by Tyrosine and Phenylalanine Restriction in the Absence of Host Selection Pressures," *Anticancer Research*, 13:523-528 (1993).
Elstad et al., "Tyrosine and Phenylalanine Restriction Sensitizes Adriamycin-Resistant P388 Leukemia Cells to Adriamycin," *Nutrition and Cancer*, 25:47-60 (1996).
Fritz et al., "Phenylalanine Ammonia-Lyase," *The Journal of Biological Chemistry*, 251(15):4646-4650 (1976).
Fu et al., "Inflence of Tyrosine and Phenylalanine Limitation on Cytotoxicity of Chimeric TGF-α Toxins on B16BL6 Murine Melanoma in Vitro," *Nutrition and Cancer*, 31(1):1-7 (1998).
Fu et al., "Focal Adhesion Kinase-Dependent Apoptosis of Melanoma Induced Tyrosine and Phenylalanine Deficiency," *Cancer Research*, 59:758-765 (1999).
Fu et al., "Specific Amino Acid Dependency Regulates Invasiveness and Viability of Androgen-Independent Prostate Cancer Cells," *Nutrition and Cancer*, 45(1):60-73 (2003).
Fu et al., "Selective Amino Acid Restriction Targets Mitochondria to Induce Apoptosis of Androgen-Independent Prostate Cancer Cell," *Journal of Cellular Physiology*, 208:522-534 (2006).
Gamez et al., "Development of Pegylated Forms of Recombinant Rhodosporidium Toruloides Phenylalanine Ammonia-Lyase for the Treatment of Classical Phenylketonuria," *Molecular Theory*, 11(6):986-989 (2005).
Gilbert et al., "The Effect of Proteinases on Phenylalanine Ammonia-Lyase from the Yeast *Rhodotorula glutinis," Biochem. J.*, 199:715-723 (1981).
Gilbert et al., "Protection of Phenylalanine Ammonia-Lyase from Proteolytic Attack," *Biochemical and Biophysical Research Communications*, 131(2)557-563 (1985).
Goodson et al., "Site-Directed Pegylation of Recombinant Interleukin-2 at Its Glycosylation Site," *Biotechnology*, 8:343-346 (1990).
Graham, "Pegaspargase: A Review of Clinical Studies," *Advanced Drug Delivery Reviews*, 55:1293-1302 (2003).
Greenwald et al., "Effective Drug Delivery of PEGylated Drug Conjugates," *Advanced Drug Delivery Reviews*, 55:217-250 (2003).
Harris et al., "Effect of Pegylation on Pharmaceuticals," Nature Reviews, Drug Discovery, 2:214-221 (2003).
Hedstrom et al., "Converting Trypsin to Chymotrypsin: The Role of Surface Loops," *Science*, 255(5049):1249-1253 (1992).
Hermeling et al., "Structure-Immunogenicity Relationships of Therapeutic Proteins," *Pharmaceutical Research*, 21(6):897-903 (2004).
Hershfield et al., "Use of Site-Directed Mutagenesis to Enhance the Epitope-Shielding Effect of Covalent Modification of Proteins with Polyethylene Glycol," *Proc. Natl. Acad. Sci. USA*, 88:7185-7189 (1991).
Hershfield, Enzyme Replacement Therapy of Adenosine Deaminase Deficiency with Polyethylene Glycol-Modified Adenosine Deaminase (PEG-ADA), *Immunodeficiency*, 4:93-97 (1993).
Hill et al., "Investigation of the Early Steps in Soraphen A Biosynthesis," *Chemical Communications*, 12:1358-1359 (2003).
Hofmann et al., "Recent Advances in the Application of Expressed Protein Ligation to Protein Engineering," *Current Opinion in Biotechnology*, 13(4):297-303 (2002).
Hoffmann et al., "Sequence Analysis and Biochemical Characterization of the Nostopeptolide A Biosynthetic Gene Cluster from *Nostoc* sp. GSV224," *Gene*, 311:171-180 (2003).
Holden et al., "Chorismate Lyase: Kinetics and Engineering for Stability," *Biochim. Biphys. Acta*, 1594:160-167 (2002).
Hopfner et al., "New Enzyme Lineages by Subdomain Shuffling," *Proc. Natl. Acad. Sci., USA*, 95:9813-9818 (1998).
Hoskins et al., "Enzymatic Control of Phenylalanine Intake in Phenylketonuria," *The Lancet*, 392-394 (Feb. 23, 1980).
Hoskins et al., "Phenylalanine Ammonia Lyase in the Management of Phenylketonuria: The Relationship Between Ingested Cinnamate and Urinary Hippurate in Humans," *Research Communications in Chemical Pathology and Parmacology*, 35(5):275-282 (1982).
Hoskins et al., "The Metabolism of Cinnamic Acid by Healthy and Phenylketonuric Adults: a Kinetic Study," *Biomedical Mass Spectrometry*, 11(6):296-300 (1984).
Ikeda et al., "Phenylalanine Ammmonia-Lyase Modified with Polyethylene Glycol: Potential Therapeutic Agent for Phenylketonuria," *Amino Acids*, 29(3):283-287 (2005).
International Search Report and Written Opinion, PCT/US2005/033895, Sep. 5, 2006.

Kalaitzis et al., "Mutasynthesis of Enterocin and Wailupemycin Analogues," *Journal of the American Chemical Society*, 125:9290-9291 (2003).
Kalghatgi et al., "Multitubular Reactors with Immobilized L-Phenylalanine Ammonia-Lyase for Use in Extracorporeal Shunts." *Research Communications in Chemical Pathology and Pharmacology*, 27(3):551-561 (1980).
Kaufman, "A Model of Human Phenylalanine Metabolism in Normal Subjects and in Phenylalanine Patients," *Proc. Natl. Acad. Sci. USA*. 96:3160-3164 (1999).
Kerbel, "Human Tumor Xenografts as Predictive Clinical Models of Anticancer Drug Activity in Humans," *Cancer Biology & Therapy*, 2:(4)S134-S139 (2003).
Kim et al., "Trends in Enzyme Therapy for Phenylketonuria," *Molecular Therapy*, 10(2):220-224 (2004).
Kinstler et al., "Characterization and Stability of N-Terminally PEGylated rhG-CSF," *Pharmaceutical Research*, 13(7):996-1002 (1996).
Koch et al., "Large Neutral Amino Acid Therapy and Phenylketonuria: a Promising Approach to Treatment," *Molecular Genetics and Metabolism*, 79:110-113 (2003).
Koukol et al., "The Metabolism of Aromatic Compounds in Higher Plants," *The Journal of Biological Chemistry*, 236(10):2692-2698 (1961).
Kreitman, "Immunotoxins for Targeted Cancer Therapy," *The AAPS Journal*, 8(3):E532-551 (2006).
Kriwacki et al., "Combined Use of Proteases and Mass Spectrometry in Structural Biology," *Journal of Biomolecular Techniques*, 9(3):5-15 (1998).
Kyndt et al., "Characterization of a Bacterial Tyrosine Ammonia Lyase, a Biosynthetic Enzyme for the Photoactive Yellow Protein," *Federation of European Biochemical Societies Letters*, 512:240-244 (2002).
Langer et al., "Identification of Essential Amino Acids in Phenylalanine Ammonia-Lyase by Site-Directed Mutagenesis," *Biochemistry*, 36:10867-10871 (1997).
Langer et al., "Methylidene-Imidazole (MIO) from Histidine and Phenylalanine Ammonia-Lyase," *Advances in Protein Chemistry*, 58:175-188 (2001).
Larue et al., "An Extracorporeal Hollow-Fiber Reactor for Phenylketonuria Using Immobilized Phenylalanine Ammonia Lyase," *Dev. Pharmacol. Ther.*, pp. 9:73-81 (1986).
Lazar et al., "Designing Proteins for Therapeutic Applications," *Current Opinion in Structural Biology*, 13:513-518 (2003).
Lee et al., "N-Terminal Site-Specific Mono-PEGylation of Epidermal Growth Factor," *Pharmaceutical Research*, 20(5):818-825 (2003).
Leong et al., Adapting Pharmacokinetic Properties of a Humanized Anti-Interleukin-8 Antibody for Therapeutic Applications using Site-Directed Pegylation, *Cytokine*, 16:(3):106-119 (2001).
Levy, "Phenylketonuria: Old Disease, New Approach to Treatment," *Proc. Natl. Acad. Sci. USA*, 96:1811-1813 (1999).
Liu et al., "Study on a Novel Strategy to Treatment of Phenylketonuria," *Art. Cells Blood Subs. Immob. Biotech.*, 30(4):243-257 (2002).
Lu et al., "Pegylation: a Method for Assessing Topological Accessibilities in Kv1.3," *Biochemistry*, 40:13288-13301 (2001).
Lucke et al., "BH4-Sensitive Hyperphenylalaninemia: New Case and Review of Literature," *Pediatric Neurology*, 28(3):228-230 (2003).
Marconi et al., "Phenylalanine Ammonia-Lyase Entrapped in Fibers," *Biochimie*, 62:575-580 (1980).
Marshall et al., "Rational Design and Engineering of Therapeutic Proteins," *Drug Discovery Today*, 8(5):212-221 (2003).
Matalon et al., "Biopterin Responsive Phenylalanine Hydroxylase Deficiency," *Genetics in Medicine*, 6(1):27-32 (2004).
Maverakis et al., Autoreactive T Cells can be Protected from Tolerance Induction Through Competition by Flanking Determinants for Access to Class II MHC, *Proceedings of the National Academy of Sciences USA*, 100(9):5342-5347 (2003).
Meadows et al., "Dietary Influence of Tyrosine and Phenylalanine on the Response of B16 Melanoma to Carbidopa-Levodopa Methyl Ester Chemotherapy," *Cancer Res.*, 42:3056-3063 (1982).
Mehvar, "Modulation of the Pharmacokinetics and Pharmacodynamics of Proteins by Polyethylene Glycol Conjugation," *J. Pharm. Pharmaceut. Sci.*, 3(1):125-136 (2000).
Meyer et al., "Reduced Antibody Response to Streptavidin Through Site-Directed Mutagenesis," *Protein Science*, 10:491-503 (2001).
Moffitt et al., "Discovery of Two Cyanobacterial Phenylalanine Ammonia Lyases: Kinetic and Structural Characterization," *Biochemistry*, 46:1004-1012 (2007).
Molineux, G., "Pegylation: Engineering Improved Pharmaceuticals for Enhanced Therapy," *Cancer Treatment Reviews*, 28(Suppl.A):13-16 (2002).
Moola et al., "*Erwinia chrysanthemi* L-Aspariginase: Epitope Mapping and Production of Antigenically Modified Enzymes," *Biochemical Journal*, 302:921-927 (1994).
Moore, "Biosynthesis of Marine Natural Products: Microorganisms (Part A)," *Natural Products Reports*, 22:580-593 (2005).
National Institutes of Health, "Phenylketonuria (PKU): Screening and Management," *NIH Consensus Statement*, 17(3):1-33 (2000).
Nunez et al., "PPAR-γ Ligands and Amino Acid Deprivation Promote Apoptosis of Melanoma, Prostate, and Breast Cancer Cells," *Cancer Letters*, 236:133-141 (2006).
Office Action for U.S. Appl. No. 11/230,374 dated Jun. 15, 2007.
Office Action for U.S. Appl. No. 11/230,374 dated Nov. 30, 2007.
Office Action for U.S. Appl. No. 11/230,374 dated Jan. 10, 2008.
Office Action for U.S. Appl. No. 11/451,999 dated Nov. 30, 2007.
Office Action for U.S. Appl. No. 11/451,999 dated Jun. 4, 2008.
Office Action for U.S. Appl. No. 11/451,999 dated Aug. 22, 2008.
Parkinson et al., "Pegvisomant in the Treatment of Acromegaly," *Advanced Drug Delivery Reviews*, 55:1303-1314 (2003).
Pedersen et al., "Preparation of Immobilized L-Phenylalanine Ammonia-Lyase in Tubular Form for Depletion of L-Phenylalanine," *Research Communications in Chemical Pathology and Pharmacology*, 20(3):559-569 (1978).
Pettit et al., "Structure-Function Studies of Interleukin 15 Using Site-Specific Multigenesis, Polyethylene Glycol Conjugation, and Homology Modeling," *The Journal of Biological Chemistry*, 272(4):2312-2318 (1997).
Pilbak et al., "The Essential Tyrosine-Containing Loop Conformation and the Role of the C-Terminal Multi-Helix Region in Eukaryotic Phenylalanine Ammonia-Lyases," *FEBS Journal*, 273:1004-1019 (2006).
Poppe et al., "Methylidene-Imidazole: a Novel Electrophile for Substrate Activation," *Current Opinion in Chemical Biology*, 5:512-524 (2001).
Poppe et al., "Properties and Synthetic Applications of Ammonia-Lyases," *Current Organic Chemistry*, 7:1297-1315 (2003).
Poppe et al., "Fiedel-Crafts-Type Mechanism for the Enzymatic Elimination of Ammonia from Histidine and Phenylalanine," *Angewandte Chemie Int. Ed.*, 44:3668-3688 (2005).
Rao et al., "Degradation of Aromatic Amino Acids by Fungi," *Canadian Journal of Biochemistry*, 45:1863-1872 (1967).
Reddy et al., "Use of Peginterferon alfa-2a (40 KD) (Pegasys®) for the Treatment of Hepatitis C," *Advanced Drug Delivery Reviews*, 54:571-586 (2002).
Roberts et al., "In Vivo Effects of Phenylalanine Ammonia-Lyase," *Cancer Treatment Reports*, 60(3):261-263 (1976).
Rother et al., "Characterization of the Active Site of Histidine Ammonia-Lyase from *Pseudomonas putida," European Journal of Biochemistry*, 268:6011-6019 (2001).
Rother et al., "An Active Site Homology Model of Phenylalanine Ammonia-Lyase from *Petroselinum crispum," European Journal of Biochemistry*, 269:3065-3075 (2002).
Russell et al., "Recombinant Proteins for Genetic Disease," *Clin. Genet.*, 55:389-394 (1999).
Sarkissian et al., "A Different Approach to Treatment of Phenylketonuria: Phenylalanine Degradation with Recombinant Phenylalanine Ammonia Lyase," *Proceedings of the National Academy of Sciences USA*, 96:2339-2344 (1999).
Sarkissian et al., "A Heteroallelic Mutant Mouse Model: A New Orthologue for Human Hyperphenylalaninemia," *Molecular Genetics and Metabolism*, 69:188-194 (2000).

Schellekens, "Factors Influencing the Immunogenicity of Therapeutic Proteins," *Nephrology Dialysis Transplantation*, 20( Suppl. 6):vi3-vi9 (2005).
Schuster et al., "Serine-202 is the Putative Precursor of the Active Site Dehydroalanine of Phenylalanine Ammonia Lyase. Site-directed Mutagenesis Studies on the Enzyme from Parsley (*Petroselinum crispum* L.)," *Federation of European Biochemical Societies Letters*, 349:252-254 (1994).
Schuster et al., "The Mechanism of Action of Phenylalanine Ammonia-Lyase: The Role of Prosthetic Dehydroalanine," *Proceedings of the National Academy of Sciences USA*, 92:8433-8437 (1995).
Schwede et al., "Crystal Structure of Histidine Ammonia-Lyase Revealing a Novel Polypeptide Modification as the Catalytic Electrophile," *Biochemistry*, 38:5355-5361 (1999).
Shen et al., "Clearance of Phenylalanine Ammonia-Lyase from Normal and Tumor-Bearing Mice," *Cancer Research*, 37:1051-1056 (1977).
Shen et al., "Total-Body Radiation Suppression of the Clearance of Phenylalanine Ammonia-Lyase from Mouse Plasma," *Journal of the Reticuloendothelial Society*, 23(3):167-175 (1978).
Shen et al., "Biochemical Properties and Immunogenicity of L-Phenylalanine Ammonia-Lyase: Effects on Tumor-Bearing Mice," *Cancer Treatment Reports*, 63(6):1063-1068 (1979).
Sorlie et al. "Mechanistic Features and Structure of the Nitrogenase alpha-Gin-195 MoFe Protein," *Biochemistry*, 40:1540-1549 (2001).
Spaapen et al., Tetrahydrobiopterin-Responsive Phenylalanine Hydroxylase Deficiency, State of the Art, *Molecular Genetics and Metabolism*, 78:93-99 (2003).
Spencer et al., "A Strategy for Mapping and Neutralizing Conformational Immunogenic Sites on Protein Therapeutics," *Proteomics*, 2(3):271-279 (2002).
Stith et al., "Effects of Phenylalanine Ammonia-Lyase and Phenylalanine Deprivation on Murine Leukemic Lymphoblasts in Vitro," *Cancer Research*, 33:966-971 (1973).
Suchi et al., "Molecular Cloning of a cDNA Encoding Human Histidase," *Biochimica et Biophysica Acta*, 1216:293-295 (1993).
Tangri et al., "Rationally Engineered Proteins or Antibodies with Absent or Reduced Immunogenicity," *Current Medical Chemistry*, 9:2191-2199 (2002).
Taylor et al., "Cloning and Expression of Rat Histidase," *The Journal of Biological Chemistry*, 265(30):18192-18199 (1990).
Taylor et al., "Site-Directed Mutagenesis of Conserved Serines in Rat Histidase," *Journal of Biological Chemistry*, 269(44):27473-27477 (1994).
Vellard, "The Enzyme as Drug: Application of Enzymes as Pharmaceuticals," *Current Opinion in Biotechnology*, 14:1-7 (2003).
Veronese et al., "Branched and Linear Poly(Ethylene Glycol): Influence of the Polymer Structure on Enzymological, Pharmacokinetic, and Immunological Properties of Protein Conjugates," *Journal of Bioactive and Compatible Polymers*, 12:196-207 (1997).
Veronese et al., "Introduction and Overview of Peptide and Protein Pegylation," *Advanced Drug Delivery Reviews*, 54(4):453-456 (2002).
Wang et al., " New Carbohydrate-Based Materials for the Stabilization of Proteins," *Journal of the American Chemical Society*, 1992, 114:378-380 (1992).
Wang et al., "New Preparation for Oral Administration of Digestive Enzyme. Lactase Complex Microcapsules," *Biomat. Art. Cells Immob. Biotech*., 21(5):637-646 (1993).
Wang et al., "Structural and Biological Characterization of Pegylated Recombinant Interferon alpha-2b and its Therapeutic Implications," *Advanced Drug Delivery Reviews*, 54:547-570 (2002).
Wang et al., "Structure-Based Chemical Modification Strategy for Enzyme Replacement Treatment of Phenylketonuria," *Molecular Genetics and Metabolism*, 86(1-2):134-140 (2005) Academic Press, San Diego, CA.
Whittle et al., "Protein Structure-Based Drug Design," *Annual review of Biophysics and Biomolecular Structure*, 23:349-375 (1994).
Wieder et al., "Some Properties of Polyethylene Glycol: Phenylalanine Ammonia-Lyase Adducts," *The Journal of Biological Chemistry*, 254(24):12579-12587 (1979).
Wilks et al., "Design of a Specific Phenyllactate Dehydrogenase by Peptide Loop Exchange on the *Bacillus stearothermophilus* Lactate Dehydrogenase Framework," *Biochemistry*, 31:7802-7806 (1992).
Williams et al., "The Gene sltA Encodes a Phenylalanine Ammonia-Lyase that is Involved in the Production of a Stilbene Antibiotic in *Photorhabdus luminescens* TT01," *Microbiology*, 151:2543-2550 (2005).
Woolf et al., "The Dietary Treatment of Phenylketonuria," *Archives of Disease in Childhood*, 33:31-45, vol. 33 (1958).
Xiang et al., "Inactivation, Complementation, and Heterologous Expression of encP, a Novel Bacterial Phenylalanine Ammonia-Lyase Gene," *Journal of Biological Chemistry*, 277(36):32505-32509 (2002).
Xiang et al., "Biochemical Characterization of a Prokaryotic Phenylalanine Ammonia Lyase," *Journal of Bacteriology*, 187(12):4286-4289 (2005) [also includes Author's correction 188(14):5331 2006].
Yeung et al., "Elimination of an Immunodominant CD4+ T Cell Epitope in Human IFN-β Does Not Result in an In Vivo Response Directed at the Subdominant Epitope," *Journal of Immunology*, 172:6658-6665 (2004).
Yoshioka et al., "Optimal Site-Specific PEGylation of Mutant TNF-α Improves Its Antitumor Potency," *Biochemical and Biophysical Research Communications*, 315:808-814 (2004).
Zon et al., "Inhibitors of Phenylalanine Ammonia-Lyase: I-Aminobenzylphosphonic Acids Substituted in the Benzene Ring," *Phytochemistry*, 59:9-21 (2002).
Dermer (1994) "Another anniversary for the war on cancer" *Bio/Technology* 12:320.
Freshney (1983) Culture of Animal Cells: A Manual of Basic Technique (Alan R. Liss, Inc., New York, NY), pp. 3-4.
Gura (1997) "Systems for identifying new drugs are often faulty," *Science* 278:1041-1042.
Watts et al. (2006) "Discovery of Substrate Selectivity Switch in Tyrosine Ammonia-Lyase, a Member of the Aromatic Amino Acid Lyase Family," *Chemistry and Biology, Current Biology* (London, GB) vol. 13, No. 12, pp. 1317-1326.
Wang et al. (2008) Structural and biochemical characterization of the therapeutic *Anabaena variabilis* phenylalanine ammonia lyase,: *J. Mol. Biol*. 380:623-635.
International Search Report and Written Opinion for PCT/US2008/006661 (WO2008/153776) dated Nov. 12, 2008.
Notice of Allowance for U.S. Appl. No. 11/451,999 dated Aug. 22, 2008.
Notice of Allowance for U.S. Appl. No. 11/451,999 dated Mar. 10, 2009.
Notice of Allowance for U.S. Appl. No. 11/807,227 (U.S. Pub. No. 2008-0008695) dated Mar. 30, 2009.
Notice of Allowance for U.S. Appl. No. 12/107,736 (U.S. Pub. No. 2009-0047265) dated Apr. 1, 2009.

* cited by examiner

FIGURE 1A

Gene Sequence of Nostoc punctiforme PAL

| | | | | | | |
|---|---|---|---|---|---|---|
| 1 | atgaatataa | catctctaca | acagaacata | acgcgttctt | ggcaaatacc | tttcactaat |
| 61 | agttcagatt | caatcgtaac | tgtaggcgat | cgcaatctga | caatcgacga | ggttgtaaat |
| 121 | gttgctcgtc | atggaacaca | ggtgcgctta | actgataatg | cagatgtcat | tcggggtgtt |
| 181 | caagcatctt | gtgattacat | taacaatgca | gtcgaaacag | cacagccaat | ttacggggtg |
| 241 | acatctggct | ttggcggtat | ggcagatgtt | gtcatctctc | gcgaacaagc | agcggaactt |
| 301 | cagactaatt | taatttggtt | tctgaaatcc | ggcgcaggaa | acaaattatc | gttagcagac |
| 361 | gtgcgtgcag | ctatgctctt | acgtgcaaat | tcacatttgt | atggtgcgtc | tggtatacga |
| 421 | ctcgaactta | ttcagcggat | tgaaactttc | ctcaacgctg | gcgtgacacc | ccatgtctat |
| 481 | gagtttggct | ctatcggtgc | tagcggcgat | ttggtgccat | tatcctacat | tactggggca |
| 541 | ctaatcggtc | tagatcctag | ctttacagtt | gacttcgacg | gtaaagaaat | ggatgccgtt |
| 601 | acagccttgt | ctcgtttggg | tttgccaaag | ttgcaattgc | aaccgaaaga | aggtttagca |
| 661 | atgatgaatg | gcacctcagt | catgacaggt | attgcagcta | actgtgtgta | cgatgcgaaa |
| 721 | gttttgctcg | ctctgacaat | gggtgtacac | gccttagcca | tccaaggttt | atacggaacg |
| 781 | aatcaatctt | tccacccgtt | tattcatcag | tgcaagccac | atcccggtca | actatggaca |
| 841 | gcagatcaaa | tgtttctct | gctgaaagat | tcatctttag | ttcgtgaaga | gttggatggt |
| 901 | aaacacgaat | accgtggtaa | agatctgata | caggatcgtt | attctctccg | ctgtctggca |
| 961 | cagttcatag | ggccaatcgt | tgatggggta | tcagagatta | ccaagcaaat | cgaggtagaa |
| 1021 | atgaactcag | tcaccgataa | cccattgatt | gatgtcgaga | accaagttag | ttatcacggc |
| 1081 | ggcaattttc | tcggacagta | tgtgggtgtg | acaatggatc | gcctacgtta | ttacataggg |
| 1141 | ctattggcca | aacacatcga | tgtgcagatt | gcacttcttg | tctcgccaga | gtttagcaac |
| 1201 | ggcttaccac | cctctttagt | tggtaatagc | gatcgcaaag | ttaatatggg | actcaaaggt |
| 1261 | ttgcaaatca | gtggaaactc | gattatgcca | ctgttgagct | tctatggaaa | ttccctagcc |
| 1321 | gatcgctttc | ctacccacgc | cgagcaattt | aatcaaaata | ttaacagcca | aggctatatt |
| 1381 | tccgcaaatt | tgacacgtcg | ttccgtagac | atatttcaga | attatatggc | gatcgcgttg |
| 1441 | atgtttggag | ttcaagctgt | tgacctccgc | acatataaga | tgaaaggtca | ttatgatgca |
| 1501 | cgtacatgcc | tctcacccaa | tactgtgcag | ttatacacag | cagtctgcga | ggtagttgga |
| 1561 | aagccactaa | cgtctgtgcg | tccatacatt | tggaacgaca | acgagcaatg | tttagatgag |
| 1621 | catattgccc | ggatttcagc | tgatatcgct | ggtggtggtt | taattgtgca | agcagttgag |
| 1681 | catatttttt | cgagcttaaa | gtcaacgtaa | | | |

FIGURE 1B

Protein Sequence of Nostoc punctiforme PAL

MNITSLQQNITRSWQIPFTNSSDSIVTVGDRNLTIDEVVNVARH

GTQVRLTDNADVIRGVQASCDYINNAVETAQPIYGVTSGFGGMADVVISREQAAELQT

NLIWFLKSGAGNKLSLADVRAAMLLRANSHLYGASGIRLELIQRIETFLNAGVTPHVY

EFGSIGASGDLVPLSYITGALIGLDPSFTVDFDGKEMDAVTALSRLGLPKLQLQPKEG

LAMMNGTSVMTGIAANCVYDAKVLLALTMGVHALAIQGLYGTNQSFHPFIHQCKPHPG

QLWTADQMFSLLKDSSLVREELDGKHEYRGKDLIQDRYSLRCLAQFIGPIVDGVSEIT

KQIEVEMNSVTDNPLIDVENQVSYHGGNFLGQYVGVTMDRLRYYIGLLAKHIDVQIAL

LVSPEFSNGLPPSLVGNSDRKVNMGLKGLQISGNSIMPLLSFYGNSLADRFPTHAEQF

NQNINSQGYISANLTRRSVDIFQNYMAIALMFGVQAVDLRTYKMKGHYDARTCLSPNT

VQLYTAVCEVVGKPLTSVRPYIWNDNEQCLDEHIARISADIAGGGLIVQAVEHIFSSL

KST

FIGURE 2A

Gene Sequence of Anabaena variabilis PAL 1 atgaagacac tatctcaagc acaaagcaaa acctcatctc aacaattttc ttttactgga
61 aattcttctg ccaatgtaat tattggtaat cagaaactca caatcaatga tgttgcaagg
121 gtagcgcgta atggcacctt agtgtcttta accaataaca ctgatatttt gcagggtatt
181 caggcatctt gtgattacat taataatgct gttgaatctg gggaaccaat ttatggagtg
241 acatctggtt ttggcggtat ggccaatgtt gccatatccc gtgaacaagc atctgaactc
301 caaaccaact tagtttggtt cctgaaaaca ggtgcaggga acaaattacc cttggcggat
361 gtgcgcgcag ctatgctctt gcgtgcaaac tctcatatgc gcggtgcatc tggcatcaga
421 ttagaactta tcaagcgtat ggagattttc cttaacgctg gtgtcacacc atatgtgtat
481 gagtttggtt caattggtgc aagtggtgat ttagtgccac tatcctacat tactggttca
541 ctgataggct tagatcccag ttttaaggtt gacttcaacg gtaaagaaat ggatgcgcca
601 acagctctac gtcaactgaa tttgtcaccc ttgacattgt tgccgaagga aggcttggcg
661 atgatgaacg gcacttcagt catgacaggt attgcagcaa actgcgtcta cgatactcaa
721 attttaactg cgatcgctat gggcgttcac gctctagata tccaagcttt aaacggaacc
781 aatcaatcat tccatccatt tatccataat tccaaaccac atcctggtca attatgggca
841 gcagatcaga tgatttcttt gttagccaat tcccagttag ttcgtgatga gttagatggt
901 aaacacgatt atcgtgatca cgagttgatt caagatcgtt actcactccg atgccttccc
961 cagtatttgg ggccaatcgt tgatggaatt tcccagattg ccaaacaaat tgaaatcgaa
1021 atcaactcag tcaccgataa cccactaatt gatgttgata accaagctag ctatcatgga
1081 ggaaatttcc tcggacagta cgtgggtatg ggaatggatc acctgcgtta ctatattggg
1141 ttattggcta aacacctaga tgtgcagatt gccctcctcg cctcaccaga gtttagcaat
1201 ggactaccac catctttatt aggcaaccga gaacgtaaag tcaatatggg actcaaaggt
1261 ctgcaaatat gcggtaactc aattatgcca ctgttgacct tctatggaaa ttccatcgcc
1321 gatcgctttc ctacccatgc agaacaattt aatcagaaca tcaacagtca aggatacact
1381 tcagcgactc tagcccgccg ttctgtggat atcttccaga attatgtggc gatcgctctg
1441 atgtttggag tccaagctgt tgacctccgc acatataaaa agactggtca ttacgatgca
1501 cgcgcctgtc tatcacctgc aactgagcgc ttatattcag cagtccgcca cgtagttgga
1561 caaaaaccaa cttcagatcg cccatatatt tggaatgata atgagcaagg actggatgag
1621 catattgccc ggatttctgc tgatatcgct gctggtggtg tgattgtgca agcagttcaa
1681 gatatcttac cctgcttgca ttaa

FIGURE 2B

Protein Sequence of Anabaena variabilis PAL

```
1       mktlsqaqsk tssqqfsftg nssanviign qkltindvar varngtlvsl tnntdilqgi
61      qascdyinna vesgepiygv tsgfggmanv aisreqasel qtnlvwflkt gagnklplad
121     vraamllran shmrgasgir lelikrmeif lnagvtpyvy efgsigasgd lvplsyitgs
181     ligldpsfkv dfngkemdap talrqlnlsp ltllpkegla mmngtsvmtg iaancvydtq
241     iltaiamgvh aldiqalngt nqsfhpfihn skphpgqlwa adqmisllan sqlvrdeldg
301     khdyrdheli qdryslrclp qylgpivdgi sqiakqieie insvtdnpli dvdnqasyhg
361     gnflgqyvgm gmdhlryyig llakhldvqi allaspefsn glppsllgnr erkvnmglkg
421     lqicgnsimp lltfygnsia drfpthaeqf nqninsqgyt satlarrsvd ifqnyvaial
481     mfgvqavdlr tykktghyda raclspater lysavrhvvg qkptsdrpyi wndneqglde
541     hiarisadia aggvivqavq dilpclh
```

FIGURE 4

Alignment of cyanobacterial protein sequences of N. punctiforme PAL (SEQ ID NO:4) and A. variabilis (SEQ ID NO:2) with EncP PAL (SEQ ID NO:5) and P. putida HAL (SEQ ID NO:6). Active site residues which correspond to PAL or HAL activity are highlighted and underlined.

```
Avar03005300   MKTLSQAQSK TSSQQFSFTG NSSANVIIGN QKLTINDVAR VARNGTLVSL
Npun02008223   MNITSLQQNI TRSWQIPFTN SSDSIVTVGD RNLTIDEVVN VARHGTQVRL
EncP           .......... .......... ..MTFVIELD MNVTLDQLED AARQRTPVEL
PputidaHAL     .......... .......... ..MTELTLKP GTLTLAQLRA IHAAPVRLQL

Avar03005300   TNNTDILQGI QASCDYINNA VESGEPIYGV TSGFGGMANV AISREQASEL
Npun02008223   TDNADVIRGV QASCDYINNA VETAQPIYGV TSGFGGMADV VISREQAAEL
EncP           S..APVRSRV RASRDVLVKF VQDERVIYGV NTSMGGFVDH LVPVSQARQL
PputidaHAL     D..ASAAPAI DASVACVEQI IAEDRTAYGI NTGFGLLAST RIASHDLENL

Avar03005300   QTNLVWFLKT GAGNKLPLAD VRAAMLLRAN SHMRGASGIR LELIKRMEIF
Npun02008223   QTNLIWFLKS GAGNKLSLAD VRAAMLLRAN SHLYGASGIR LELIQRIETF
EncP           QENLINAVAT NVGAYLDDTT ARTIMLSRIV SLARGNSAIT PANLDKLVAV
PputidaHAL     QRSLVLSHAA GIGAPLDDDL VRLIMVLKIN SLSRGFSGIR RKVIDALIAL

Avar03005300   LNAGVTPYVY EFGSIGASGD LVPLSYITGS LIGLDPSFKV DFNGKEMDAP
Npun02008223   LNAGVTPHVY EFGSIGASGD LVPLSYITGA LIGLDPSFTV DFDGKEMDAV
EncP           LNAGIVPCIP EKGSLGTSGD LGPLAAIALV CAGQW...KA RYNGQIMPGR
PputidaHAL     VNAEVYPHIP LKGSVGASGD LAPLATMSLV LLGEG...KA RYKGQWLSAT

Avar03005300   TALRQLNLSP LTLLPKEGLA MMNGTSVMTG IAANCVYDTQ ILTAIAMGVH
Npun02008223   TALSRLGLPK LQLQPKEGLA MMNGTSVMTG IAANCVYDAK VLLALTMGVH
EncP           QALSEAGVEP MELSYKDGLA LINGTSGMVG LGTMVLQAAR RLVDRYLQVS
PputidaHAL     EALAVAGLEP LTLAAKEGLA LLNGTQASTA YALRGLFYAE DLYAAAIACG

Avar03005300   ALDIQALNGT NQSFHPFIHN SKPHPGQLWA ADQMISLLAN SQLVRDELDG
Npun02008223   ALAIQGLYGT NQSFHPFIHQ CKPHPGQLWT ADQMFSLLKD SSLVREELDG
EncP           ALSVEGLAGM TKPFDPRVHG VKPHRGQRQV ASRLWEGLAD SHLAVNELDT
PputidaHAL     GLSVEAVLGS RSPFDARIHE ARGQRGQIDT AACFRDLLGD SSEVS.....
```

FIGURE 4 (CONTINUED)

| | | | | | |
|---|---|---|---|---|---|
| Avar03005300 | .........K | HDYRDHELIQ | DRYSLRCLPQ | YLGPIVDGIS | QIAKQIEIEI |
| Npun02008223 | .........K | HEYRGKDLIQ | DRYSLRCLAQ | FIGPIVDGVS | EITKQIEVEM |
| EncP | EQTLAGEMGT | VAKAGSLAIE | DAYSIRCTPQ | ILGPVVDVLD | RIGATLQDEL |
| PputidaHAL | .......... | LSHKNCDKVQ | DPYSLRCQPQ | VMGACLTQLR | QAAEVLGIEA |
| | | | | | |
| Avar03005300 | NSVTDNPLID | VDNQASYHGG | NFLGQYVGMG | MDHLRYYIGL | LAKHLDVQIA |
| Npun02008223 | NSVTDNPLID | VENQVSYHGG | NFLGQYVGVT | MDRLRYYIGL | LAKHIDVQIA |
| EncP | NSSNDNPIVL | PEEAEVFHNG | HFHGQYVAMA | MDHLNMALAT | VTNLANRRVD |
| PputidaHAL | NAVSDNPLVF | AAEGDVISGG | NFHAEPVAMA | ADNLALAIAE | IGSLSERRIS |
| | | | | | |
| Avar03005300 | LLASPEFSNG | LPPSLLGNRE | RKVNMGLKGL | QICGNSIMPL | LTFYGNSIAD |
| Npun02008223 | LLVSPEFSNG | LPPSLVGNSD | RKVNMGLKGL | QISGNSIMPL | LSFYGNSLAD |
| EncP | RFLDKSNSNG | LPAFLCREDP | .GLRLGLMGG | QFMTASITAE | TRTLTIPMSV |
| PputidaHAL | LMMDKHMS.Q | LPPFLVENG. | .GVNSGFMIA | QVTAAALASE | NKALSHPHSV |
| | | | | | |
| Avar03005300 | RFPTHAEQFN | **Q**NINSQGYTS | ATLARRSVDI | FQNYVAIALM | FGVQAVDLRT |
| Npun02008223 | RFPTHAEQFN | **Q**NINSQGYIS | ANLTRRSVDI | FQNYMAIALM | FGVQAVDLRT |
| EncP | QSLTSTADF. | **Q**DIVSFGFVA | ARRAREVLTN | AAYVVAFELL | CACQAVDIRG |
| PputidaHAL | DSLPTSANQ. | **E**DHVSMAPAA | GKRLWEMAEN | TRGVPAIEWL | GACQGLDLRK |
| | | | | | |
| Avar03005300 | YKKTGHYDAR | ACLSPATERL | YSAVRHVVGQ | KPTSDRPYIW | NDNEQGLDEH |
| Npun02008223 | YKMKGHYDAR | TCLSPNTVQL | YTAVCEVVGK | PLTSVRPYIW | NDNEQCLDEH |
| EncP | ADKL...... | ...SSFTRPL | YERTRKIVP. | .........F | FDRDETITDY |
| PputidaHAL | GLKT...... | ...SAKLEKA | RQALRSEVA. | .........H | YDRDRFFAPD |
| | | | | | |
| Avar03005300 | IARISADIAA | GGVIVQAVQD | ILPCLH.. | | |
| Npun02008223 | IARISADIAG | GGLIVQAVEH | IFSSLKST | | |
| EncP | VEKLAADLIA | GEPVDAAVAA | H....... | | |
| PputidaHAL | IEKAVELLAK | GSLTGLLPAG | VLPSL... | | |

FIGURE 5A-5E

Protein Sequence of AvPAL Variants (Cysteine Mutants)

A. AvPAL_C64S (SEQ ID NO:7)
MKTLSQAQSKTSSQQFSFTGNSSANVIIGNQKLTINDVARVARNGTLVSLTNNTDILQGIQASSDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARACLSPATERLYSAVRHVVGQKPTSDRPYIWNDNEQGLDEHIARISADIAAGGVIVQAVQ
DILPCLH

B. AvPAL_C318S (SEQ ID NO:8)
MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRSLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARACLSPATERLYSAVRHVVGQKPTSDRPYIWNDNEQGLDEHIARISADIAAGGVIVQAVQ
DILPCLH

C. AvPAL_C503S (SEQ ID NO:9)
MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARASLSPATERLYSAVRHVVGQKPTSDRPYIWNDNEQGLDEHIARISADIAAGGVIVQAVQ
DILPCLH

D. AvPAL_C565S (SEQ ID NO:10)
MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARACLSPATERLYSAVRHVVGQKPTSDRPYIWNDNEQGLDEHIARISADIAAGGVIVQAVQ
DILPSLH

E. AvPAL_C565SC503S (SEQ ID NO:11)
MKTLSQAQSKTSSQQFSFTGNSSANVIIGNQKLTINDVARVARNGTLVSLTNNTDILQGIQASCDYINNA
VESGEPIYGVTSGFGGMANVAISREQASELQTNLVWFLKTGAGNKLPLADVRAAMLLRANSHMRGASGIR
LELIKRMEIFLNAGVTPYVYEFGSIGASGDLVPLSYITGSLIGLDPSFKVDFNGKEMDAPTALRQLNLSP
LTLLPKEGLAMMNGTSVMTGIAANCVYDTQILTAIAMGVHALDIQALNGTNQSFHPFIHNSKPHPGQLWA
ADQMISLLANSQLVRDELDGKHDYRDHELIQDRYSLRCLPQYLGPIVDGISQIAKQIEIEINSVTDNPLI
DVDNQASYHGGNFLGQYVGMGMDHLRYYIGLLAKHLDVQIALLASPEFSNGLPPSLLGNRERKVNMGLKG
LQICGNSIMPLLTFYGNSIADRFPTHAEQFNQNINSQGYTSATLARRSVDIFQNYVAIALMFGVQAVDLR
TYKKTGHYDARASLSPATERLYSAVRHVVGQKPTSDRPYIWNDNEQGLDEHIARISADIAAGGVIVQAVQ
DILPSLH 1. rAvPAL eluate
2. rAvPAL C503S eluate
3. rAvPAL C64S eluate
4. rAvPAL C565S eluate1
5. rAvPAL C565S eluate2
6. rAvPAL C565SC503S eluate
7. rAvPAL C565SC503S tail FIGURE 11
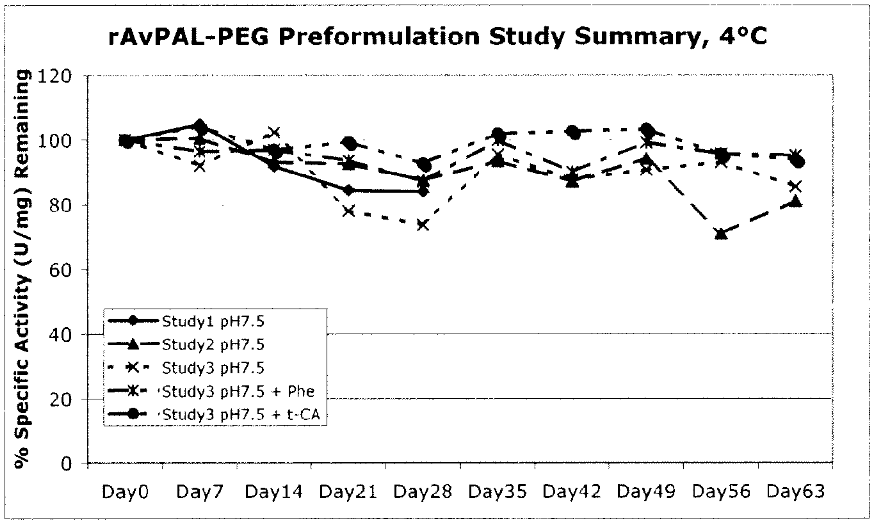
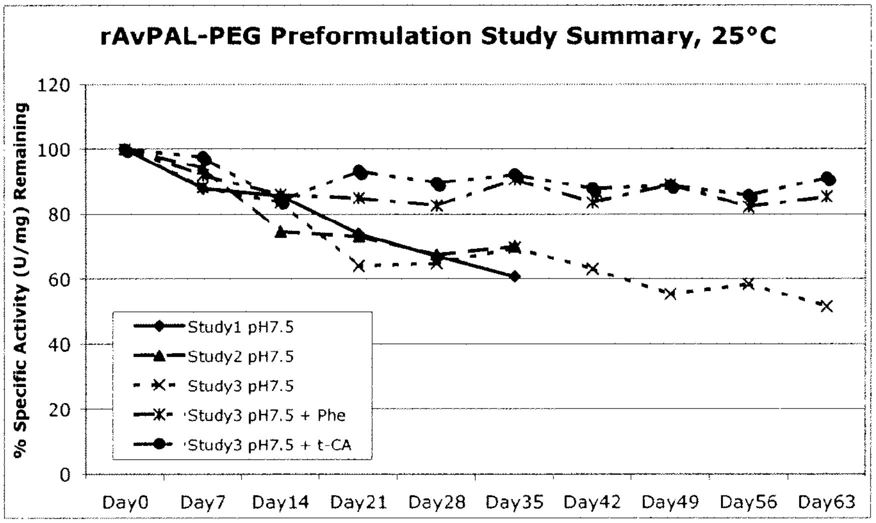
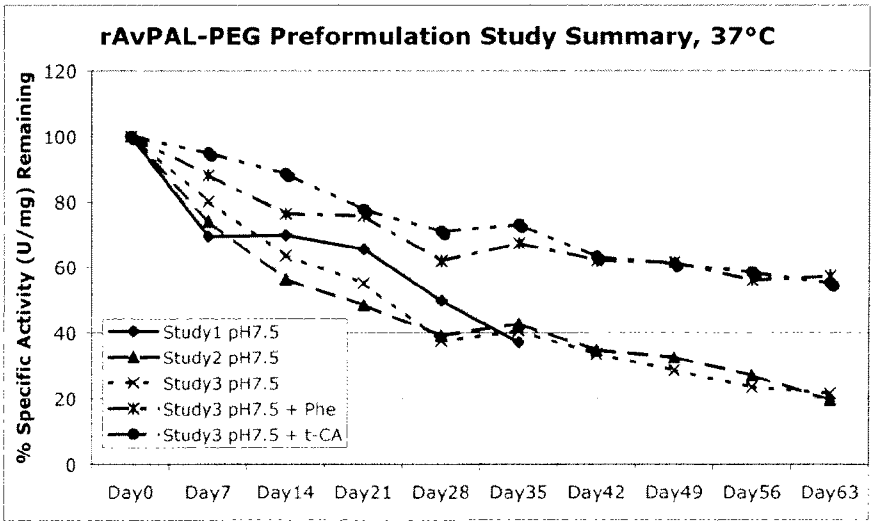

FIGURE 13A-B
A.
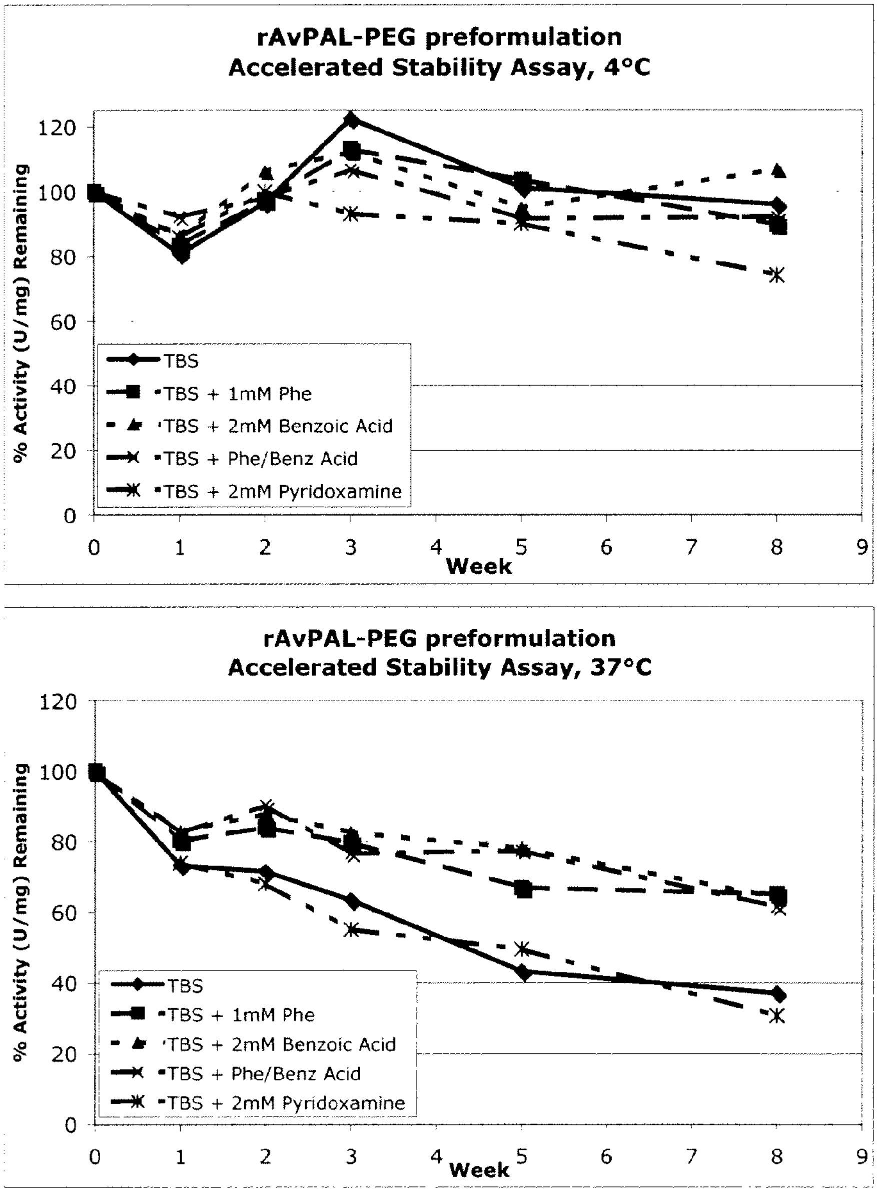
B.
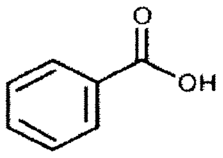
Benzoic acid
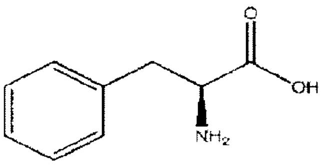
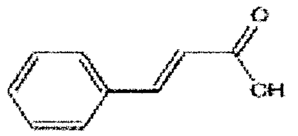
t-Cinnamic Acid FIGURE 14A-B
A. Concentration of AvPAL_C565SC503S in Plasma of Cynomolgus Monkeys After a Single Subcutaenous Injection
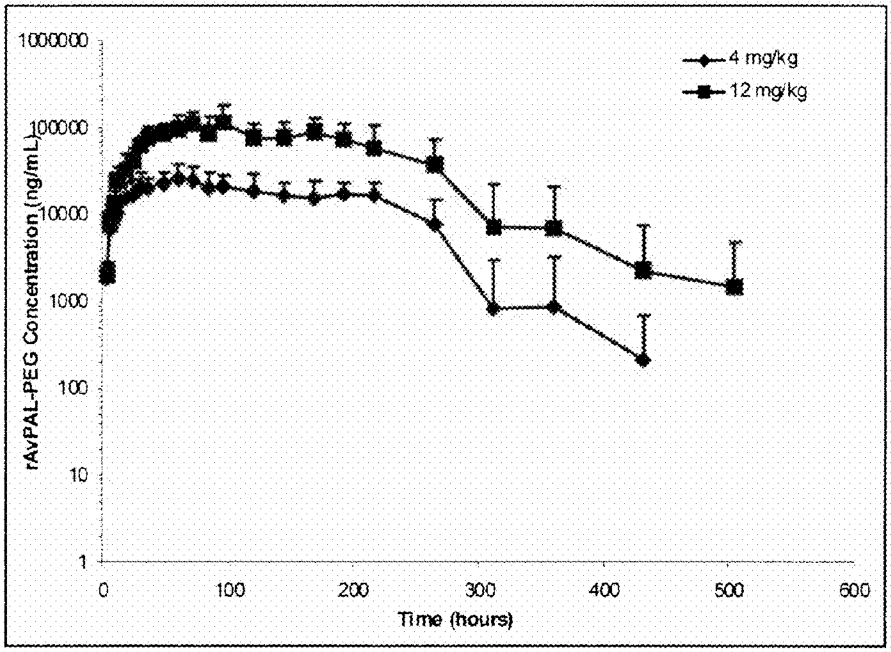
B. Concentration of Phenylalanine (Phe) and AvPAL_C565SC503S in Plasma of Cynomolgus Monkeys After a Single Subcutaneous Injection
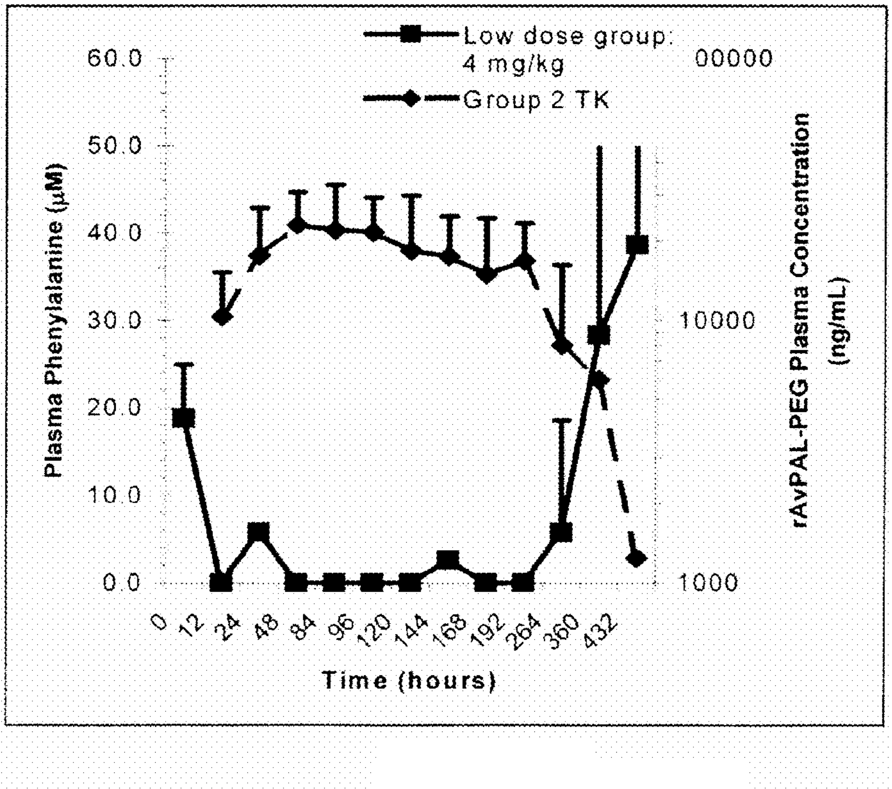

FIGURE 15A-B
A. Concentration of AvPAL_C565SC503S in Plasma of Rats After a Single Intravenous Injection
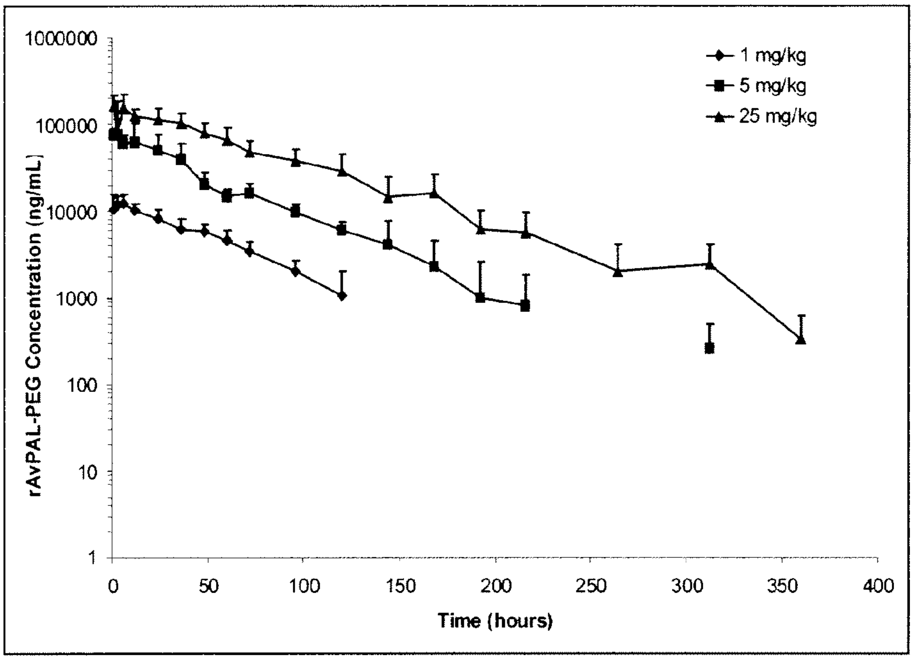
B. Concentration of AvPAL_C565SC503S in Plasma of Rats After a Single Subcutaneous Injection
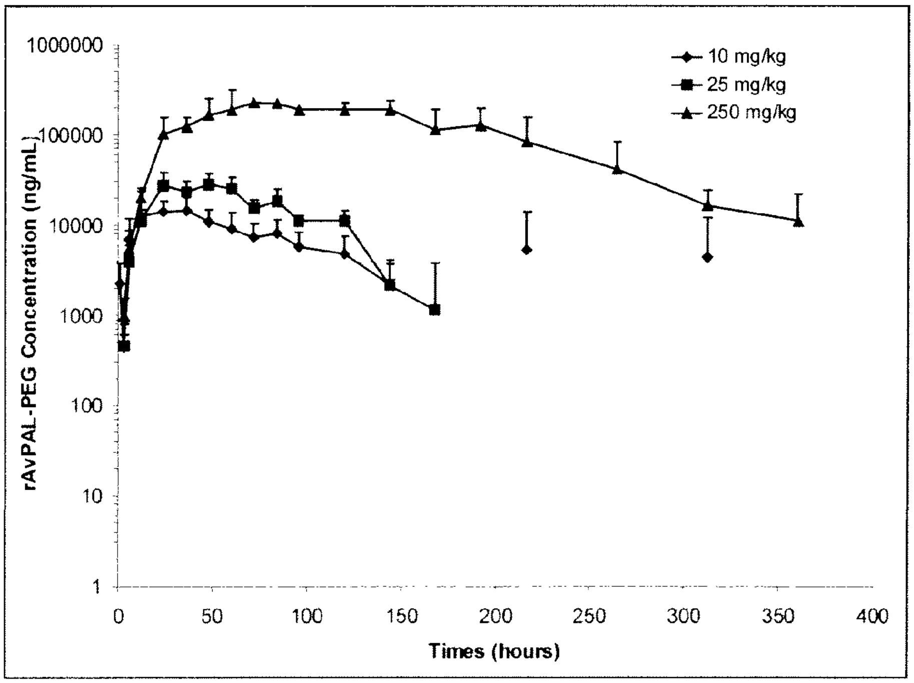

FIGURE 16A-B
A. NOMO1 Acute Myeloid Leukemia (AML) Cells
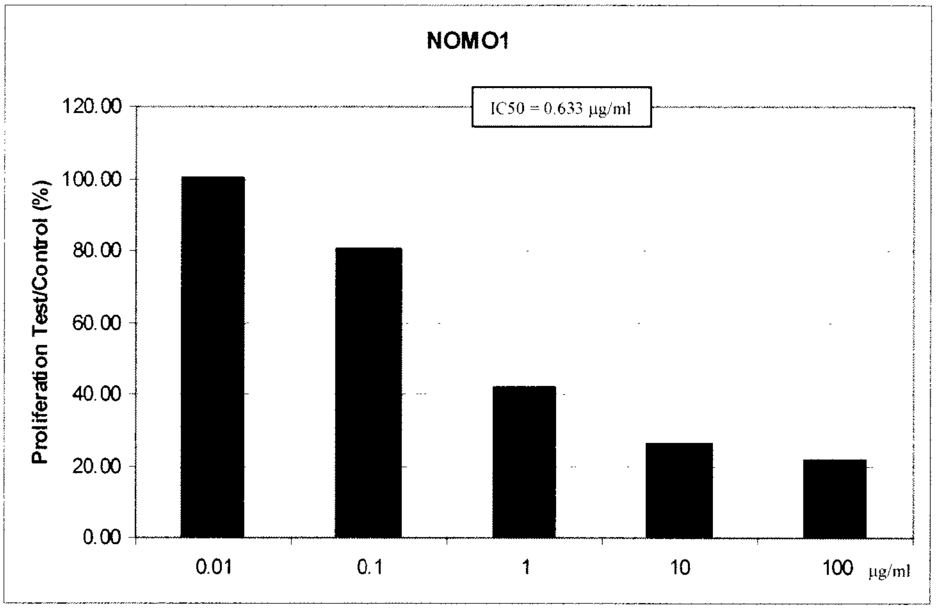
B. IM9 Myeloma Cells
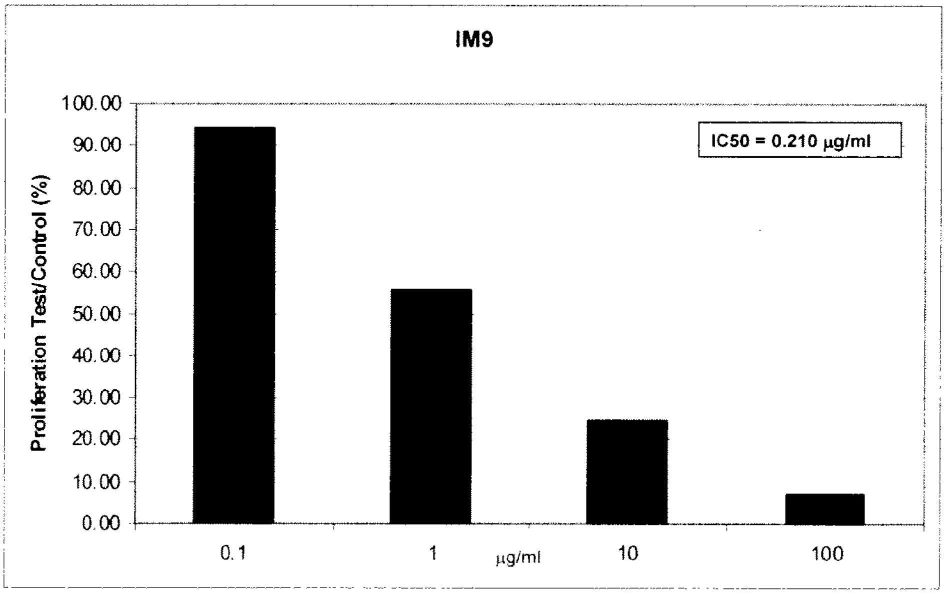

FIGURE 17A
A. Brain/CNS – SF268 (Top) and 498L (Bottom)
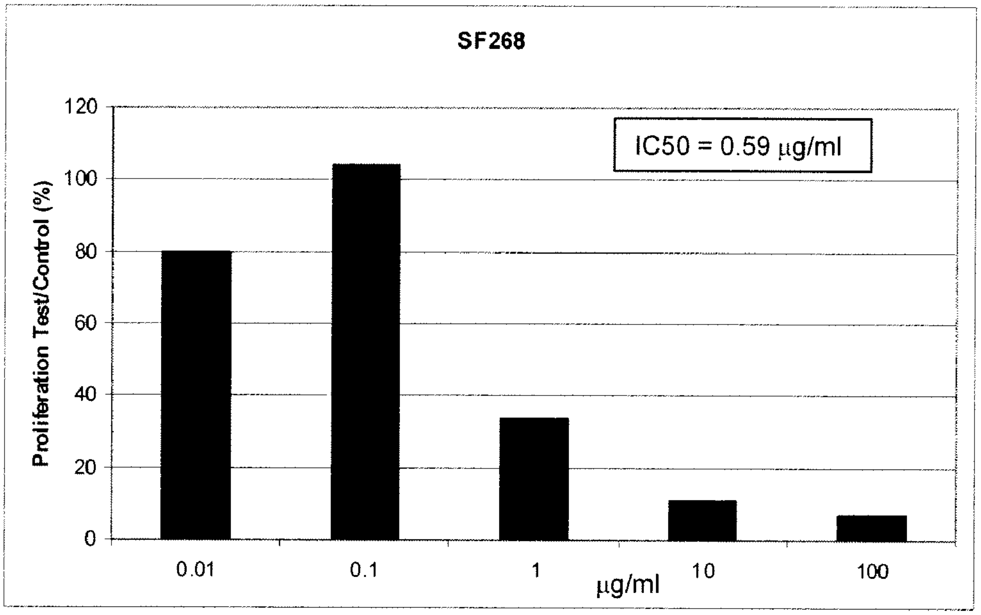
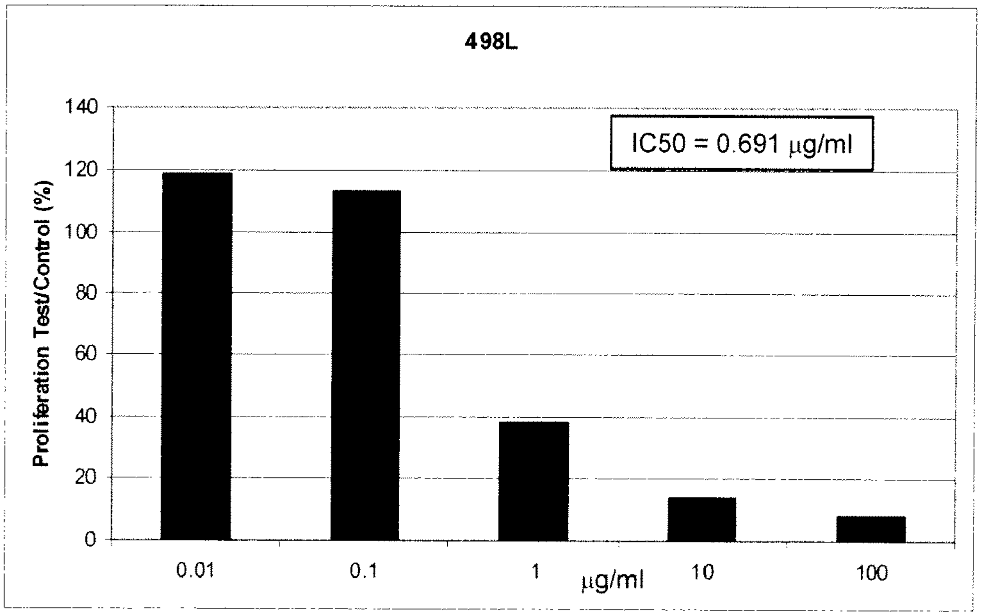

FIGURE 17B
B. Colon – HT29 (Top) and HCT116 (Bottom)
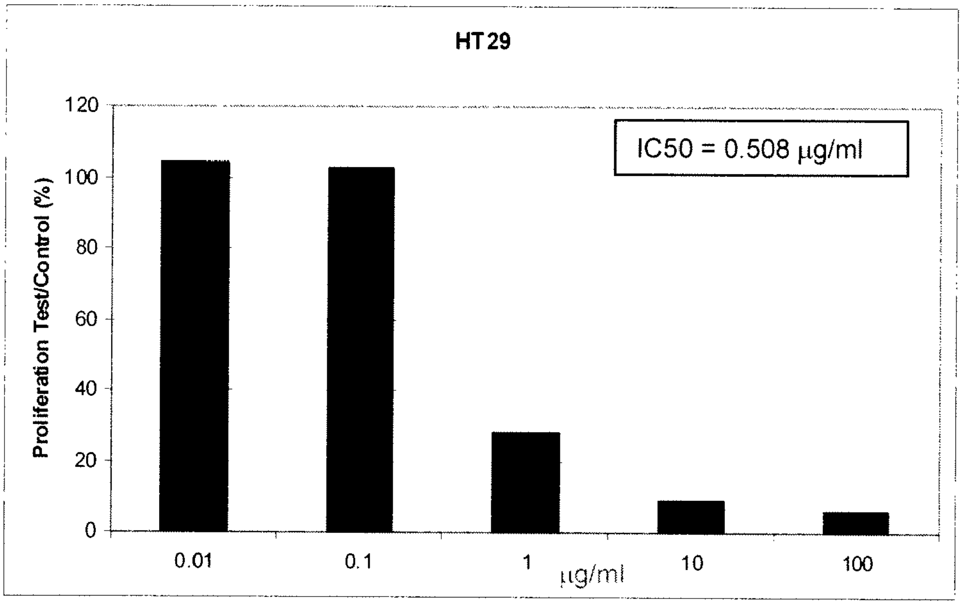
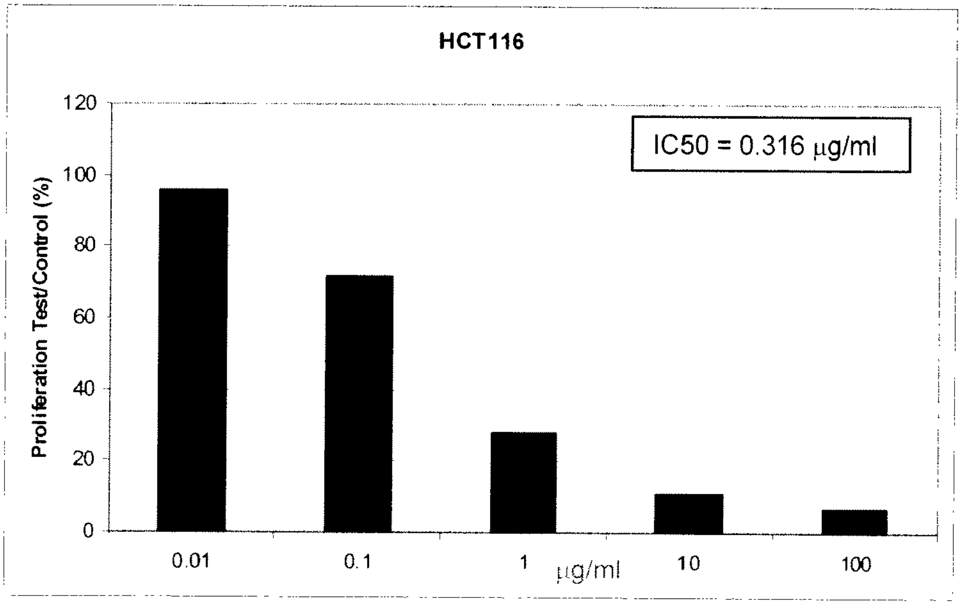

FIGURE 17C
C. Lung – H460 (Top), 529L (Middle) and 629L (Bottom)
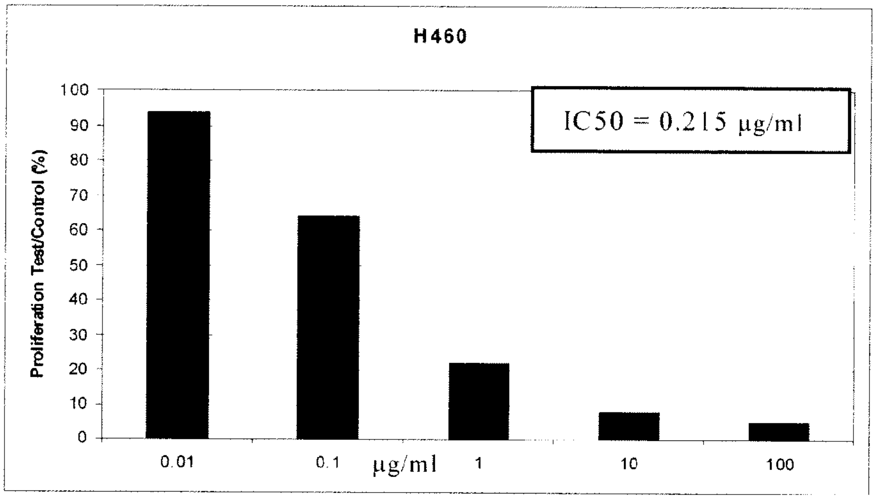
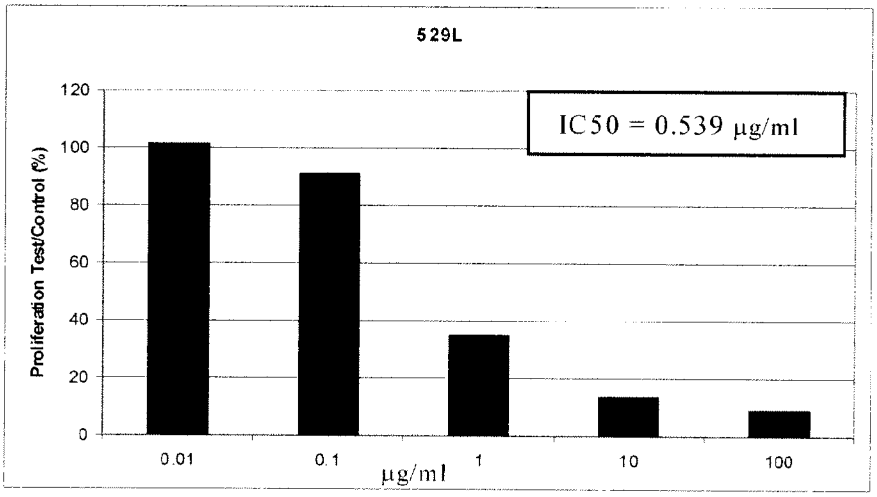
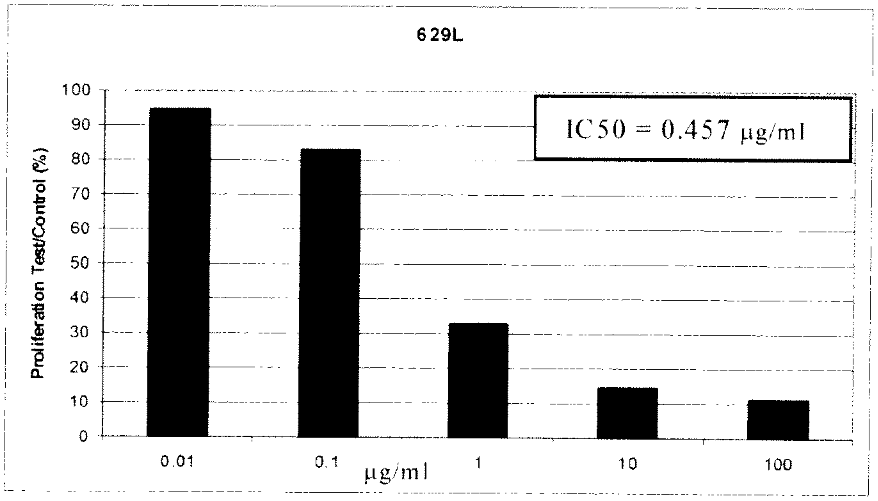

D. Prostate – LNCAP (Top), PC3M (Middle) and DU145 (Bottom)

COMPOSITIONS OF PROKARYOTIC PHENYLALANINE AMMONIA-LYASE AND METHODS OF TREATING CANCER USING COMPOSITIONS THEREOF

CROSS-REFERENCE TO RELATED APPLICATIONS

This application claims priority to U.S. Provisional Application No. 61/066,125, filed Aug. 17, 2007, the entirety of which is incorporated herein by reference.

SEQUENCE LISTING

A CRF copy of the Sequence Listing, titled 011808-0013-999_SeqListing.txt, which was saved on Apr. 22, 2008 and is 53 kbs in size is submitted herewith and is incorporated herein by reference in its entirety.

FIELD OF THE INVENTION

This invention relates to prokaryotic phenylalanine ammonia-lyase (PAL) and compositions thereof, and optimization of such compositions to enhance prokaryotic PAL catalytic activity and/or stability, while reducing immunogenicity and/or proteolytic sensitivity of prokaryotic PAL. The invention further relates to the use of such optimal compositions of prokaryotic PAL for treating cancer.

BACKGROUND OF THE INVENTION

PAL is a non-mammalian enzyme widely distributed in plants (Koukol, et al., J. Biol. Chem. 236:2692-2698 (1961); Hanson, et al., The Enzymes 7:75-166 (1972); Poppe, et al., Curr. Org. Chem. 7:1297-1315 (2003)), some fungi (Rao, et al., Can. J. Biochem. 4512:1863-1872 (1967); Abell, et al., Methods Enzymol. 142:242-253 (1987)) and bacteria (Bezanson, et al., Can. J. Microbiol. 16:147-151 (1970); Xiang, et al., J. Biol. Chem. 277:32505-32509 (2002); Hill, et al., Chem. Commun. 1358-1359 (2003)) and can be recombinantly produced in *Escherichia coli.*

A representative list of PALs includes: Q9ATN7 *Agastache rugosa*; O93967 *Amanita muscaria* (Fly agaric); P35510, P45724, P45725, Q9SS45, Q8RWP4 *Arabidopsis thaliana* (Mouse-ear cress); Q6ST23 *Bambusa oldhamii* (Giant timber bamboo); Q42609 *Bromheadia finlaysoniana* (Orchid); P45726 *Camellia sinensis* (Tea); Q9MAX1 *Catharanthus roseus* (Rosy periwinkle) (Madagascar periwinkle); Q9SMK9 *Cicer arietinum* (Chickpea); Q9XFX5, Q9XFX6 *Citrus clementina*×*Citrus reticulate*; Q42667 *Citrus limon* (Lemon); Q8H6V9, Q8H6W0 *Coffea canephora* (Robusta coffee); Q852S1 *Daucus carota* (Carrot); O23924 *Digitalis lanata* (Foxglove); O23865 *Daucus carota* (Carrot); P27991 *Glycine max* (Soybean); O04058 *Helianthus annuus* (Common sunflower); P14166, Q42858 *Ipomoea batatas* (Sweet potato); Q8GZR8, Q8W2E4 *Lactuca sativa* (Garden lettuce); O49835, O49836 *Lithospermum erythrorhizon;* P35511, P26600 *Lycopersicon esculentum* (Tomato); P35512 *Malus domestica* (Apple) (*Malus sylvestris*); Q94C45, Q94F89 *Manihot esculenta* (Cassaya) (Manioc); P27990 *Medicago sativa* (Alfalfa); P25872, P35513, P45733 *Nicotiana tabacum* (Common tobacco); Q6T1C9 *Quercus suber* (Cork oak); P14717, P53443, Q7M1Q5, Q84VE0, Q84VE0 *Oryza sativa* (Rice); P45727 *Persea americana* (Avocado); Q9AX15 *Pharbitis nil* (Violet) (Japanese morning glory); P52777 *Pinus taeda* (Loblolly pine); Q01861, Q04593 *Pisum sativum* (Garden pea); P24481, P45728, P45729 *Petroselinum crispum* (Parsley) (*Petroselinum hortense*); Q84LI2 *Phalaenopsis*×*Doritaenopsis* hybrid cultivar; P07218, P19142, P19143 *Phaseolus vulgaris* (Kidney bean) (French bean); Q7XJC3, Q7XJC4 *Pinus pinaster* (Maritime pine); Q6UD65 *Populus balsamifera* subsp. *trichocarpa*×*Populus deltoides*; P45731, Q43052, O24266 *Populus kitakamiensis* (Aspen); Q8H6V5, Q8H6V6 *Populus tremuloides* (Quaking aspen); P45730 *Populus trichocarpa* (Western balsam poplar); O64963 *Prunus avium* (Cherry); Q94EN0 *Rehmannia glutinosa*; P11544 *Rhodosporidium toruloides* (Yeast) (*Rhodotorula gracilis*); P10248 *Rhodotorula rubra* (Yeast) (*Rhodotorula mucilaginosa*); Q9M568, Q9M567 *Rubus idaeus* (Raspberry); P31425, P31426 *Solanum tuberosum* (Potato); Q6SPE8 *Stellaria longipes* (Longstalk starwort); P45732 *Stylosanthes humilis* (Townsville stylo); P45734 *Trifolium subterraneum* (Subterranean clover); Q43210, Q43664 *Triticum aestivum* (Wheat); Q96V77 *Ustilago maydis* (Smut fungus); P45735 *Vitis vinifera* (Grape); and Q8VXG7 *Zea mays* (Maize).

Numerous studies have focused on the use of the enzyme phenylalanine ammonia-lyase (PAL, EC 4.3.1.5) for enzyme substitution treatment of phenylketonuria (PKU) (Hoskins, et al., Lancet 1(8165):392-394 (1980); Gilbert, et al., Biochem. J. 199(3):715-723 (1981); Hoskins, J. A., et al., Res. Commun. Chem. Pathol. Pharmacol. 35(2):275-282 (1982); Sarkissian, et al., Proc. Natl. Acad. Sci. USA 96(5):2339-2344 (1999); Liu, et al., Artif. Cells Blood Substit. Immobil. Biotechnol. 30(4):243-257 (2002); Wieder, et al., J Biol. Chem. 254(24):12579-12587 (1979); Gamez, et al., Mol. Ther. 11(6):986-989 (2005); Ambrus, et al., J. Pharmacol. Exp. Ther. 224(3):598-602 (1983); Ambrus, et al., Science 201(4358):837-839 (1978); Kalghatgi, Res. Commun. Chem. Pathol. Pharmacol. 27(3):551-561 (1980); Ambrus, Res. Commun. Chem. Pathol. Pharmacol. 37(1):105-111 (1982); Gilbert, et al., Biochem. Biophys. Res. Commun. 131(2):557-563 (1985); Pedersen, Res. Commun. Chem. Pathol. Pharmacol. 20(3):559-569 (1978); Marconi, et al., Biochimie 62(8-9):575-580 (1980); Larue, et al., Dev. Pharmacol. Ther. 9(2):73-81 (1986); Ambrus, et al., Ann. Intern. Med. 106(4):531-537 (1987); Bourget, et al., Appl. Biochem. Biotechnol. 10:57-59 (1984); Bourget, et al., FEBS Lett. 180 (1):5-8 (1985); Bourget, et al., Biochim. Biophys. Acta 883 (3):432-438 (1986); Chang, et al., Artif. Cells Blood Substit. Immobil. Biotechnol. 23(1):1-21 (1995); Chang, et al., Mol. Biotechnol. 17(3):249-260 (2001); U.S. Pat. No. 5,753,487).

The use of PAL for cancer treatment has been suggested based on its ability to limit the nutrient supply of phenylalanine to cancer cells and thereby inhibit neoplastic growth (Fritz, et al., J. Biol. Chem. 251(15):4646-4650 (1976); Roberts, et al., Cancer Treat. Rep. 60(3):261-263 (1976); Shen, et al., Cancer Res. 37(4):1051-1056 (1977); Shen, et al., Cancer Treat. Rep. 63(6):1063-1068 (1979); Wieder, et al., J. Biol. Chem. 254(24):12579-12587 (1979)). In addition, PAL-mediated reduction in phenylalanine prevented the proliferation of murine leukemia and metastatic melanoma. However, intravenously injected pegylated PAL was cleared rapidly from circulating blood after the 13th injection (Abell, et al., Cancer Res. 33:2529-2532 (1973); Roberts, et al., (1976), ibid.; Shen, et al., (1977), ibid.; (Shen, et al., J. Reticuloendothelial Soc. 23:167-175 (1978)).

Certain neoplastic or cancer cells have a higher metabolic rate and a greater requirement than normal cells for essential amino acids such as phenylalanine. There is evidence in the literature suggesting that restriction or reduction of specific amino acids, e.g., phenylalanine, through the use of amino acid degrading enzymes, e.g., PAL, may reduce the growth of certain tumor cells in human cancer patients and in animal models. For example, certain leukemic cells lack the enzyme asparagine synthetase, which synthesizes the non-essential amino acid asparagine from glutamine, and are thus dependent upon asparagine for survival. Oncaspar (pegaspargase, Enzon Pharmaceuticals, Inc.), a pegylated L-asparaginase, has been used successfully to treat acute lymphoblastic leukemia (ALL) (Graham, Adv. Drug Del. Rev. 55:1293-1302 (2003)). Other examples of amino acids as potential targets for enzymatic depletion in cancer therapy include glutamine (glutamine deaminase, Medical Enzymes AG), arginine (arginine deiminase, Phoenix Pharmacologics, Inc.) and methionine (methioninase, Anticancer, Inc.) (See, for example, U.S. Pat. Nos. 6,312,939, 6,737,259 and 5,690, 929).

Dietary restriction of phenylalanine has been shown to inhibit growth and metastasis of highly invasive metastatic melanoma and androgen independent prostate cancer cells in animal models, promote apoptosis of tumor, but not normal, cells in culture, increase survival of tumor-bearing mice, sensitize tumor cells to chemotherapeutic agents, and augment cytotoxicity by toxins (Fu, et al., Nutr. Cancer 31:1-7 (1998); Fu, et al., Cancer Res. 59:758-765 (1999); Fu, et al., Nutr. Cancer 45:60-73 (2003); Fu, et al., J. Cell. Physiol. 209:522-534 (2006); Meadows, et al., Cancer Res. 42:3056-3063 (1982); Elstad, et al., Anticancer Res. 13:523-528 (1993); Elstad, et al., Nutr. Cancer 25:47-60 (1996); Nunez, et al., Cancer Lett. 236:133-141 (2006)).

Enzymatic depletion of phenylalanine using PAL from the yeast *Rhodosporidium toruloides* (also known as *Rhodotorula glutinis*) (RtPAL) inhibited the growth of leukemic lymphocytes in culture in vitro (Abell, et al., Cancer Res. 32:285-290 (1972); Stith, et al., Cancer Res. 33:966-971 (1973)) and in mice in vivo (Abell, et al., Cancer Res. 33:2529-2532 (1973)). However, after repeated injections into mice, the clearance of RtPAL from plasma was greatly accelerated, and the clearance rate was more rapid in tumor bearing, as compared to non-tumor bearing, mice (Fritz, et al., J. Biol. Chem. 251:4646-4650 (1976); Shen, et al., Cancer Res. 37:1051-1056 (1977)). The half-life of RtPAL was decreased to about 1 hour after multiple administration due to an increase in antibody titer, demonstrating that total body radiation may be necessary to delay clearance and enhance half-life (Shen, et al., J. Reticuloendothelial Soc. 23:167-175 (1978).

RtPAL has been pegylated in an attempt to reduce the enzyme's immunogenicity and clearance rate in vivo (Wieder, et al., J. Biol. Chem. 254:12579-12587 (1979)). After a single intravenous injection or after multiple intravenous injections into mice, the blood half-life of pegylated RtPAL was longer than unpegylated RtPAL; however, the pegylated RtPAL was still rapidly cleared from the blood after the thirteenth intravenous injection.

Although PAL potentially has various therapeutic applications, the use of PAL may be limited by reduced specific activity and proteolytic instability. Similar to other therapeutic proteins, use of PAL as an enzyme therapy is accompanied by several disadvantages such as immunogenicity and proteolytic sensitivity (see Vellard, Curr. Opin. Biotechnol. 14:1-7 (2003)). As yet, a concerted effort toward improving these parameters has not been made due to a paucity of structural and biochemical knowledge regarding this protein. Thus, there remains a need for PAL molecules with optimal kinetic characteristics, including potent catalytic activity, greater biological half-life, greater biochemical stability, and/or attenuated immunogenicity, for therapeutic use, including the treatment of cancer.

SUMMARY OF INVENTION

The invention is based on the finding that prokaryotic or bacterial PAL may serve as an effective treatment for cancer. The invention contemplates compositions of prokaryotic PAL and biologically active fragments, mutants, variants or analogs thereof, with enhanced properties, such as more potent catalytic activity, greater biochemical stability and, for therapeutic applications, attenuated immunogenicity and/or greater biological half-life. The invention provides pharmaceutical compositions and formulations comprising prokaryotic PAL and biologically active fragments, mutants, variants or analogs thereof and a pharmaceutically acceptable carrier, including stabilizers. The present invention also provides methods of production and purification of prokaryotic PAL and biologically active fragments, mutants, variants or analogs thereof, and methods of using such compositions for therapeutic purposes, including the treatment of neoplastic disease and cancer.

As used herein, "bacterial PAL" and "prokaryotic PAL" are used interchangeably to mean (1) wild-type PAL from a prokaryotic organism, including but not limited to PAL from *Streptomyces maritimus* (also known as EncP, SEQ ID NO:5, FIG. 4), *Nostoc punctiforme* (SEQ ID NO:2, FIG. 4), *Anabaena variabilis* (SEQ ID NO:4, FIG. 4), *Anacystis nidulans* (Lofflehardt, *Z. Naturforsch.* 31(11-12):693-9 (1976), *Photorabdus luminescens* TT01 (Williams, et al., Microbiology 151:2543-2550 (2005), and *Streptomyces verticillatus* (Bezanson, et al., Can. J. Microbiol. 16(3):147-51 (1970); (2) fragments, mutants, variants or analogs of such wild-type PAL enzymes that retain similar (i.e., at least 50%) catalytic activity for phenylalanine, and that preferably exhibit increased catalytic activity, greater biochemical stability, increased half-life, and/or decreased immunogenicity, and (3) chemically modified versions of such wild-type PAL enzymes or fragments, mutants, variants or analogs thereof that have been are linked to other chemical moieties that provide other advantageous effects, such as, for example and not for limitation, enhanced half-life and/or decreased immunogenicity. For example, any references to methods of making or using prokaryotic PAL, and fragments, mutants, variants, analogs or chemically modified versions thereof, and compositions of such enzyme(s), for therapeutic purposes, are meant to refer to methods of making, using or formulating all such wild-type prokaryotic PAL or fragments, mutants, variants, analogs or chemical modifications thereof.

In a first aspect, the present invention provides pharmaceutical compositions comprising bacterial PAL and biologically active fragments, mutants, variants or analogs thereof, and a pharmaceutically acceptable carrier. A preferred embodiment is a bacterial PAL from *Nostoc punctiforme* (SEQ ID NO:2) or biologically active fragment, mutant, variant or analog thereof. Another preferred embodiment is a bacterial PAL from *Anabaena variabilis* (SEQ ID NO:4) or biologically active fragment, mutant, variant or analog thereof. The invention contemplates prokaryotic PAL variants that have greater phenylalanine-converting activity and/or reduced immunogenicity as compared to a wild-type PAL.

Preferably, the prokaryotic PAL variants retain the wild-type active site residues at positions corresponding to Ser210, Ala-Ser-Gly triad (211-213), Asp214, Leu215, Asn270, Val269, Leu266, Leu134, His137, Lys468, Glu496, Gln500 in PAL from *Rhodosporidium toruloides* PAL (RtPAL) or conservative substitution(s) of these active site residue(s), of which the Ala-Ser-Gly triad at 211-213 is believed to be the binding site for phenylalanine.

Desirable prokaryotic PAL variants may include proteins in which one or more amino acid residues have been substituted by another amino acid residue to reduce protein aggregation that can be associated with decreased enzyme activity, increased immunogenicity, and/or other disadvantageous effects, such as reduced bioavailability, in vivo. The invention contemplates a pharmaceutical composition wherein one or more amino acid residues of the prokaryotic PAL variant have been substituted by another amino acid wherein the substitution increases phenylalanine-converting activity and/or reduces immunogenicity as compared to the wild-type PAL.

In some embodiments, one or more amino acid residues of the prokaryotic PAL variant have been substituted by another amino acid residue. In some embodiments, one or more cysteine residues of the prokaryotic PAL variant have been substituted by a serine residue. In preferred embodiments, the prokaryotic PAL variant is an *Anabaena variabilis* PAL (AvPAL). In more preferred embodiments, one or more cysteine residues of the AvPAL variant have been substituted by a serine residue selected from the group consisting of cysteine residues at positions 64, 318, 503 and 565. In a more preferred embodiment, the cysteine residue at position 565 of the AvPAL variant has been substituted by a serine residue. In a most preferred embodiment, the cysteine residues at positions 503 and 565 of the AvPAL variant have been substituted by serine residues.

Desirable prokaryotic PAL variants may include fusion proteins in which the PAL enzyme has been fused to another heterologous polypeptide, such as a native or modified constant region of an immunoglobulin or a fragment thereof that retains the salvage epitope, known in the art to increase half-life, or is recognized by proteins specific to particular forms of cancer.

The invention further contemplates chemically modified versions of such prokaryotic PAL polypeptides, which have been linked to a chemical moiety that provides other advantageous effects. For example, nonspecific or site-specific (e.g., N-terminal) linkage of water-soluble polymers, e.g., polyethylene glycol, to polypeptides is known in the art to improve half-life, and linkage of chemical moieties may also reduce immunogenicity and/or improve protease resistance.

In some embodiments, the prokaryotic PAL variant comprises a water-soluble polymer. In preferred embodiments, the prokaryotic PAL variant comprises polyethylene glycol. In a more preferred embodiment, the prokaryotic PAL variant is an *Anabaena variabilis* PAL (AvPAL) and the ratio of AvPAL and polyethylene glycol is about 1:3 (1:3 AvPAL:PEG). In a most preferred embodiment, the prokaryotic PAL variant is an AvPAL variant, the ratio of the AvPAL variant and polyethylene glycol is about 1:3 (1:3 AvPAL:PEG), and the cysteine residues at positions 503 and 565 of the AvPAL variant have been substituted by serine residues.

In some embodiments, one or more amino acid residues of the prokaryotic PAL variant have been substituted by a lysine residue. The pegylation of an additional lysine residue(s) in a prokaryotic PAL variant can result in an enzyme that has reduced immunogenicity, increased catalytic activity, and/or improved biochemical stability. Without being bound to a particular theory, it is hypothesized that a tyrosine residue at/near the active site of prokaryotic PAL (e.g., position 78 in AvPAL) can be a site for pegylation, which reduces enzyme activity. In a preferred embodiment, one or more amino acids at/near the active site of the prokaryotic PAL variant that is not required for enzyme activity is substituted by a lysine residue. Without being bound to a particular theory, it is hypothesized that pegylation of the substituted lysine residue at/near the active site sterically hinders a tyrosine residue (e.g., position 78 in AvPAL) from being pegylated.

Such prokaryotic PAL variants are isolated and purified in accordance with the methods of the present invention and is thereby present in amounts which enable using the prokaryotic PAL enzyme therapeutically. In some embodiments, a cDNA encoding for a complete or wild-type prokaryotic PAL is used. However, in other embodiments, a cDNA encoding for a biologically active fragment, mutant, variant or analog thereof may be used. Further, the present invention provides compositions of optimized prokaryotic PAL obtained by structure-based molecular engineering approaches and/or chemically-modified (e.g., pegylated) forms of PAL. Specific embodiments contemplate optimal compositions of prokaryotic PAL with improved specific activity, enhanced stability, reduced immunogenicity and/or proteolytic sensitivity appropriate for therapeutic use. A preferred embodiment is a pegylated form of *Nostoc punctiforme* PAL with improved specific activity, enhanced stability, reduced immunogenicity and/or proteolytic sensitivity. Another preferred embodiment is a pegylated form of *Anabaena variabilis* PAL with improved specific activity, enhanced stability, reduced immunogenicity and/or proteolytic sensitivity.

In some embodiments, the biologically active sites of wild-type prokaryotic PAL according to the invention may be modified as desired to optimize PAL kinetic characteristics. In a preferred embodiment, a modified prokaryotic PAL has sufficient activity to reduce plasma phenylalanine levels in a subject upon treatment to a range from below the level of detection to between about 20 μM to 60 μM, preferably to less than about 20 μM, and even more preferably to less than about 10 μM, using standard detection methods well known in the art. In other preferred embodiments, the biologically active modified prokaryotic PAL has a kcat of at least about 0.1 s−1, preferably greater than about 0.5 $s^{-1}$, and even more preferably greater than about 1.0 s−1. In more preferred embodiments, the biologically active modified prokaryotic PAL has a kcat of at least about 0.4 s−1, preferably greater than about 2.0 s−1, and even more preferably greater than about 4.0 s−1. In other preferred embodiments, the biologically active modified prokaryotic PAL has a Km of between about 10 μM to about 2000 μM. In more preferred embodiments, the biologically active modified prokaryotic PAL has a Km of between about 10 μM to about 1000 μM. In even more preferred embodiments, the biologically active modified prokaryotic PAL has a Km of between about 10 μM to about 500 μM. In other preferred embodiments, the biologically active modified prokaryotic PAL exhibits enzymatic activity from about at least 50% of to about 10-fold greater than the wild-type PAL. In other preferred embodiments, the biologically active modified prokaryotic PAL exhibits enzymatic activity from about at least 50% of to about 100% higher than the wild-type PAL. Such biological active modified prokaryotic PAL proteins may be formed using methods well known in the art, such as by site-directed mutagenesis.

In further embodiments, the invention contemplates use of prokaryotic PAL or a biologically active fragment, mutant, variant or analog thereof that metabolizes phenylalanine (i.e., converts phenylalanine to another substance) in preparation of a medicament for preventing or treating cancer in a subject, preferably in a human subject, as well as a pharmaceutical composition containing prokaryotic PAL or a biologically active fragment, mutant, variant or analog thereof for use in preventing or treating cancer in a subject, preferably in a human subject. In some embodiments, the medicament is for preventing cancer in a human subject. In other embodiments, the medicament is for treating cancer in a human subject. In a preferred embodiment, the pharmaceutical composition comprises highly purified PAL derived from bacteria, or biologically active fragment, mutant, variant or analog thereof, and a pharmaceutically acceptable carrier. Preferred preparations contain prokaryotic PAL or biologically active fragment, mutant, variant or analog thereof with a purity of greater than 90%, 95%, 96%, 97%, 98%, 99%, 99.2%, 99.5%, 99.6%, 99.7%, 99.8%, or 99.9%. The relative specific activity of the prokaryotic PAL, or biologically active fragment, mutant, variant or analog thereof, according to the present invention is preferably at least about 50%, and more preferably greater than about 110%, of the specific activity of wild-type prokaryotic PAL.

In a second aspect, the present invention features novel methods of using prokaryotic PAL variant compositions for therapeutic purposes. The invention contemplates methods of treating various forms of cancer.

In one embodiment, the invention contemplates methods for treating cancer by administering to a subject in need of such treatment a therapeutically effective amount of a pharmaceutical composition comprising a prokaryotic PAL variant and a pharmaceutically acceptable carrier, wherein the prokaryotic PAL variant has a greater phenylalanine-converting activity and/or a reduced immunogenicity as compared to a wild-type PAL and is effective in reducing the phenylalanine concentration in the blood, serum or plasma, preferably in the plasma, of the subject to a range from below the level of detection to between about 20 μM to 60 μM, preferably to less than about 20 μM, and even more preferably to less than about 10 μM. In some embodiments, one or more amino acid residues of the prokaryotic PAL variant have been substituted by another amino acid residue wherein the substitution increases phenylalanine-converting activity and/or reduces immunogenicity as compared to the wild-type PAL. In some embodiments, one or more cysteine residues of the prokaryotic PAL variant have been substituted by another amino acid residue. In some embodiments, one or more cysteine residues of the prokaryotic PAL variant have been substituted by a serine residue. In a preferred embodiment, the prokaryotic PAL variant is an *Anabaena variabilis* PAL (AvPAL) variant. In a particularly preferred embodiment, one or more cysteine residues of the AvPAL variant have been substituted by a serine residue that is selected from the group consisting of cysteine residues at positions 64, 318, 503 and 565, by a serine residue at position 565, or by serine residues at positions 503 and 565. In some embodiments, the prokaryotic PAL variant comprises a water-soluble polymer. In some embodiments, the water-soluble polymer is polyethylene glycol. In a preferred embodiment, the prokaryotic PAL variant is an *Anabaena variabilis* PAL (AvPAL) variant, and the ratio of the AvPAL variant and the polyethylene glycol is about 1:3 (1:3 AvPAL:PEG). In a more preferred embodiment, the prokaryotic PAL variant is an *Anabaena variabilis* PAL (AvPAL) variant the ratio of the AvPAL variant and the polyethylene glycol is about 1:3 (1:3 AvPAL:PEG), and the cysteine residues at positions 503 and 565 of the AvPAL variant have been substituted by serine residues.

In a more particularly preferred embodiment, the invention provides a method for treating cancer comprising administering to a subject in need of such treatment a therapeutically effective amount of a pharmaceutical composition comprising an AvPAL variant and a pharmaceutically acceptable carrier, wherein the cysteine residues at positions 503 and 565 of the AvPAL variant have been substituted by serine residues, the AvPAL variant further comprises a water-soluble polymer of polyethylene glycol, wherein the ratio of AvPAL variant and the polyethylene glycol is about 1:3, and the AvPAL variant is effective in reducing the phenylalanine concentration in the blood, serum or plasma, preferably in the plasma, of the subject to a range from below the level of detection to between about 20 μM to 60 μM, preferably to less than about 20 μM, and even more preferably to less than about 10 μM.

In a broad embodiment, the cancer is a cancer wherein the proliferation and/or survival of cells derived from the cancer is sensitive to phenylalanine restriction or depletion. In preferred embodiments, the cancer is lung cancer, brain or central nervous system cancer, colon cancer, prostate cancer, renal cancer or metastatic melanoma. In other preferred embodiments, the cancer is head and neck cancer, ovarian cancer, uterine cancer, leukemia (e.g., acute myeloid leukemia or acute lymphoblastoid leukemia) or myeloma. In other preferred embodiments, the cancer is pediatric cancer or a resistant cancer (i.e., a cancer that has been shown to be resistant to cancer therapeutic agents or targeted cancer therapeutic agents).

The invention describes methods of treating cancer in a subject comprising administering to the subject a prokaryotic PAL or a biologically active fragment, mutant, variant or analog thereof wherein the administration of prokaryotic PAL is effective to lower the phenylalanine (Phe) concentration in the blood, serum or plasma, preferably in the plasma, of the subject as compared to the concentration in the absence of prokaryotic PAL administration. A subject selected for treatment according to the methods of the invention can have any plasma Phe concentration, e.g., from about 40 μM to about 2000 μM, or a normal range of plasma Phe concentration, such a concentration may be in the range from about 40 μM to about 80 μM, more typically in the range from about 50 μM to about 70 μM, with the range in most human individuals between about 55 μM to about 65 μM. The plasma Phe concentration of the subject upon treatment is reduced in the range from below the level of detection to between about 20 μM to 60 μM, preferably to less than about 20 μM, and even more preferably to less than about 10 μM, using standard detection methods well known in the art.

The invention also contemplates methods of treating cancer by administering to a subject in need of such treatment a therapeutically effective amount of a pharmaceutical composition comprising a prokaryotic PAL variant and a pharmaceutically acceptable carrier, in combination with a protein-restricted (i.e., phenylalanine-free) diet, wherein the treatment is effective to produce a decrease in the plasma Phe concentration of the subject in the absence of the combined administration. The plasma Phe concentration of the subject upon treatment is reduced in the range from below the level of detection to between about 20 μM to 60 μM, preferably to less than about 20 μM, and even more preferably to less than about 10 μM, using standard detection methods well known in the art.

In another embodiment, prokaryotic PAL or a biologically active fragment, mutant, variant or analog thereof may also be administered in combination with a protein-restricted diet. The protein-restricted diet administered in the methods herein is one that is a phenylalanine-restricted diet wherein the total Phe intake of the subject is restricted to less than 600 mg per day. In other embodiments, the protein-restricted diet is a phenylalanine-restricted diet wherein the total Phe is restricted to less than 300 mg per day. In still other embodiments, the protein-restricted diet is one supplemented with one or more amino acids, such as, for example and not for limitation, tyrosine, valine, isoleucine and/or leucine.

Also contemplated is a pharmaceutical composition comprising prokaryotic PAL or a biologically active fragment, mutant, variant or analog thereof and a pharmaceutically acceptable carrier, diluent or excipient. The pharmaceutical composition may further comprise a medical protein supplement. In still other embodiments, the protein supplement is phenylalanine-free. The protein supplement preferably is fortified with L-tyrosine, L-glutamine, L-carnitine at a concentration of 20 mg/100 g supplement, L-taurine at a concentration of 40 mg/100 g supplement and selenium. It may further comprise the recommended daily doses of minerals, e.g., calcium, phosphorus and magnesium. The supplement further may comprise the recommended daily dose of one or more amino acids selected from the group consisting of L-leucine, L-proline, L-lysine acetate, L-valine, L-isoleucine, L-arginine, L-alanine, glycine, L-asparagine monohydrate, L-tryptophan, L-serine, L-threonine, L-histidine, L-methionine, L-glutamic acid, and L-aspartic acid. In addition, the supplement may be fortified with the recommended daily dosage of vitamins A, D and E. The supplement preferably comprises a fat content that provides at least 40% of the energy of the supplement. Such a supplement may be provided in the form of a powder supplement or in the form of a protein bar.

The invention also contemplates methods of treating cancer by administering to a subject in need of such treatment a therapeutically effective amount of a pharmaceutical composition comprising a prokaryotic PAL variant and a pharmaceutically acceptable carrier, in combination with a cancer therapeutic agent or a targeted cancer therapeutic agent, wherein the treatment is effective to produce a decrease in the plasma phenylalanine concentration of the subject in the absence of the combined administration. The plasma Phe concentration of the subject upon treatment is reduced in the range from below the level of detection to between about 20 μM to 60 μM, preferably to less than about 20 μM, and even more preferably to less than about 10 μM, using standard detection methods well known in the art.

Preferred embodiments include optimizing the dosage to the needs of the organism to be treated, preferably mammals or humans, to effectively prevent or ameliorate the disease symptoms. Prokaryotic PAL may be administered in a single daily dose, multiple doses on a daily basis, in a single weekly dose, multiple doses on a weekly basis, in a single monthly dose or multiple doses on a monthly basis. In some embodiments, the PAL therapy is not continuous, but rather PAL is administered on a daily basis until the plasma Phe concentration of the subject is decreased to a range from below the level of detection to between about 20 μM to 60 μM, preferably less than about 20 μM, and even more preferably less than about 10 μM, using standard detection methods well known in the art. Preferably, wherein the plasma Phe concentration of the subject is monitored on a daily basis and the PAL is administered when a 10%-20% increase in plasma Phe concentration is observed. In yet other preferred embodiments, doses are delivered once weekly. The invention contemplates doses of at least 0.001 mg/kg, 0.005 mg/kg, 0.01 mg/kg, 0.05 mg/kg, and may range up to 0.1 mg/kg, 0.5 mg/kg, 1.0 mg/kg, 5.0 mg/kg, 12 mg/kg or higher per week. A preferred dose is 1 mg/kg/week, a more preferred dose is 0.1 mg/kg/week, and even more preferred dose is 0.01 mg/kg/week.

A variety of parenteral or nonparenteral routes of administration, including oral, transdermal, transmucosal, intrapulmonary (including aerosolized), intramuscular, subcutaneous, or intravenous, which deliver equivalent dosages are contemplated. Administration by bolus injection or infusion directly into the joints or CSF is also specifically contemplated, such as intrathecal, intracerebral, intraventricular, via lumbar puncture, or via the cisterna magna. Preferably the doses are delivered subcutaneously or orally.

Other means of increasing prokaryotic PAL activity in the human subjects are also contemplated, including gene therapy. Transfer of a prokaryotic PAL gene is possible through a variety of means known in the art, including viral vectors, homologous recombination, or direct DNA injection. Within the scope of this aspect are embodiments featuring nucleic acid sequences encoding all or a part of prokaryotic PAL or a biologically active fragment, mutant, variant or analog thereof, which may be administered in vivo into cells that are, for example and not for limitation, affected with the cancer, located nearby or adjacent to the cancer, hematopoietic cells that circulate in the bloodstream and/or migrate to the site of the cancer.

In a third aspect, the present invention provides pharmaceutical compositions or formulations of prokaryotic PAL variants, comprising bacterial PAL and biologically active fragments, mutants, variants or analogs thereof, and a pharmaceutically acceptable carrier, wherein the pharmaceutically acceptable carrier comprises a stabilizer. In some embodiments, the stabilizer is L-phenylalanine or structural analog thereof. In some embodiments, the stabilizer is selected from the group consisting of L-phenylalanine, trans-cinnamic acid and benzoic acid. In some embodiments, the stabilizer is L-phenylalanine. In some embodiments the stabilizer is trans-cinnamic acid. In some embodiments, the stabilizer is benzoic acid. In a preferred embodiment, the invention provides methods of treating cancer using such pharmaceutical compositions or formulations.

In a particularly preferred embodiment, the pharmaceutical composition or formulation comprises a prokaryotic PAL variant and a pharmaceutically acceptable carrier, wherein the prokaryotic PAL variant is an AvPAL variant, the ratio of the AvPAL variant and polyethylene glycol is about 1:3 (1:3 AvPAL:PEG), and the cysteine residues at positions 503 and 565 of the AvPAL variant have been substituted by serine residues, and the pharmaceutically acceptable carrier comprises a stabilizer. In some embodiments, the stabilizer is L-phenylalanine or structural analog thereof. In some embodiments, the stabilizer is selected from the group consisting of L-phenylalanine, trans-cinnamic acid and benzoic acid. In some embodiments, the stabilizer is L-phenylalanine. In some embodiments the stabilizer is trans-cinnamic acid. In a particularly preferred embodiment, the invention provides methods of treating cancer using such pharmaceutical compositions or formulations.

In a fourth aspect, the present invention features a method to produce recombinant prokaryotic PAL or a biologically active fragment, mutant, variant or analog thereof in amounts which enable using the enzyme therapeutically. The present invention contemplates PAL derived from bacteria including, but not limited to, *Streptomyces, Sorangium, Pseudomonas*, and cyanobacteria such as *Nostoc* and *Anabaena*. In some embodiments, PAL is derived from the bacterial species *Streptomyces maritimus, S. verticillatus, Soragium cellulosum, Nostoc punctiforme, Nostoc tobacum, Anabaena variabilis*, or *Pseudomonas putida*. In preferred embodiments, PAL is derived from cyanobacteria species *Nostoc punctiforme* or *Anabaena variabilis*. In a particularly preferred embodiment, PAL is derived from *Anabaena variabilis*. In another embodiment, prokaryotic PAL enzyme activity is generated using cDNA or DNA sequences that are derived from sequences sometimes described as coding for HAL activity or featuring a PAL-HAL motif, but possessing key PAL residues that differ from HAL.

In a broad embodiment, the method comprises the step of transforming a cDNA or DNA encoding for all or a part of a prokaryotic PAL or a biologically active fragment, mutant, variant or analog thereof into a cell suitable for the expression thereof. In preferred embodiments, an expression vector is used to transfer the DNA into a suitable cell or cell line for expression thereof. In one particularly preferred embodiment, the cDNA or DNA is transformed into *E. coli* and recombinant bacterial PAL is overexpressed, optionally as a fusion protein. In a further embodiment, the method of producing prokaryotic PAL comprises the steps of: (a) growing cells transformed with a cDNA or DNA encoding all or a biologically active fragment, mutant, variant or analog thereof of prokaryotic PAL in a suitable growth medium to an appropriate density to produce a seed culture, (b) introducing the transformed cells into a bioreactor, (c) supplying a suitable growth medium to the bioreactor, and (d) separating the transfected cells from the media containing the enzyme.

In a preferred embodiment, recombinant prokaryotic PAL or a biologically active fragment, mutant, variant or analog thereof is over-expressed, with or without an N-terminal tag (e.g., octahistidyl-tag), in a vector, preferably pIBX1 (Su, et al., Appl. Environ. Microbiol. 62:2723-2734 (1996)) or pET28a (Invitrogen) with an inducible promoter such as with IPTG (isopropyl-beta-D-thiogalactopyranoside), in *E. coli* BLR(DE3)/pLysS (Novagen) or *E. coli* BL21 (DE3)/pLysS (Invitrogen) cells. In a particularly preferred embodiment, the method of producing prokaryotic PAL comprises the steps of: (1) growing a seed culture for a bioreactor/fermenter from a glycerol stock in shake flasks; (2) introducing such seed culture into a controlled bioreactor in fed-batch mode; (3) growing said culture in glucose-supplemented media, pH (7.8), >20% dissolved oxygen, agitation up to 1200 rpm, 30° C. until reaching a cell density of OD600 of 70-100 (~22-25 hrs); (4) inducing said culture with 0.4 mM IPTG; (5) growing said culture at a reduced temperature of 22 to 26° C. until activity change is <0.1 IU/mL (approximately 40-48 hrs and an OD600 typically of 200); and (5) harvesting bacteria by continuous centrifugation. In a preferred embodiment, the cell culture media is typically defined and composed of yeast extract protein, peptone-tryptone, glucose, glycerol, casamino acids, trace salts and phosphate buffering salts.

In a fifth aspect, the present invention features a method to purify prokaryotic PAL or a biologically active fragment, mutant, variant or analog thereof. According to a first embodiment, a transformed cell mass is grown and ruptured leaving crude recombinant enzyme. Exogenous materials are normally separated from the crude bulk to prevent fouling of the columns. Chromatographic purification is conducted using one or several chromatographic resins. Subsequently, the purified protein is formulated into a buffer designed to provide stable activity over an extended period of time. In another preferred embodiment, the method to purify the prokaryotic PAL comprises the steps of: (a) lysis of the bacteria containing recombinant PAL; (b) treatment of lysate with heat to inactivate viruses; (c) clarification of this lysate using a second continuous centrifugation step and/or depth filtration; (d) passage of clarified lysate through a charcoal filtration step; (e) passage of filtrate in (d) through a final filtration step (as with a Sartorious Sartopore 0.2 μm filter); (f) passage of final filtrate over a hydrophobic interaction chromatography resin, such as a butyl hydrophobic interaction chromatography; (g) passage of eluate in (f) over an anionic chromatography resin, such as a Q ion exchange column; (h) recovery of final product by buffer exchange with tangential flow filtration; and (i) sterilization of the final product. Those skilled in the art readily appreciate that one or more of the chromatography steps may be omitted or substituted, or that the order of the chromatography steps may be changed within the scope of the present invention. Finally, appropriate sterilizing steps may be performed as desired.

In a sixth aspect, the present invention contemplates screening assays for identifying prokaryotic PAL or a biologically active fragment, mutant, variant or analog thereof that can prevent, ameliorate, or treat cancer by contacting a tumor cell in culture with the prokaryotic PAL and determining whether the prokaryotic PAL reduces the proliferation and/or survival of the tumor cells. Such screening assays may also include the steps of creating variants that include conservative or non-conservative substitutions in the active sites, e.g. Gly142, Thr-Ser-Gly triad (143-145), Asp146, Leu147, Asn196, Ile195, Leu192, Leu76, Asn79, Met400, Thr428, Gln432 in EncP from *Streptomyces maritimus*, or their equivalents in other prokaryotic PAL, such as *Nostoc punctiforme* or *Anabaena variabilis*, which are equivalent to residues Ser210, Ala-Ser-Gly triad (211-213), Asp214, Leu215, Asn270, Val269, Leu266, Leu134, His137, Lys468, Glu496, Gln500 in PAL from *Rhodosporidium toruloides* (RtPAL), in regions adjacent to the active sites, or throughout the polypeptide sequence, followed by testing the variants for in vitro phenylalanine converting activity. In certain embodiments, the method is a high throughput assay. In a preferred embodiment, complete genomes of the bacterial species are sequenced and screened for the presence of prokaryotic PAL homologs using a bioinformatics approach. In yet another preferred embodiment, PAL catalytic activity of the protein product of such homologs is confirmed, such as by testing ability to convert phenylalanine to trans-cinnamate in vitro.

In a seventh aspect, the invention provides methods of using prokaryotic PAL compositions for the diagnosis of diseases, including but not limited to cancer. In one embodiment, prokaryotic PAL is used to measure levels of Phe in blood, plasma or serum samples. In a further embodiment, the invention contemplates a diagnostic kit comprising prokaryotic PAL for use in monitoring blood, plasma or serum samples of subjects for levels of Phe.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

DETAILED DESCRIPTION OF THE FIGURES

FIG. 1. FIG. 1A: Gene sequence of *Nostoc punctiforme* PAL (SEQ ID NO:1); FIG. 1B: Protein sequence of *Nostoc punctiforme* PAL (SEQ ID NO:2).

FIG. 2. FIG. 2A: Gene sequence of *Anabaena variabilis* PAL (SEQ ID NO:3); FIG. 2B: Protein sequence of *Anabaena variabilis* PAL (SEQ ID NO:4).

FIG. 3. Relatedness tree of aromatic amino acid ammonia-lyases from prokaryotes and eukaryotes. Sequences were retrieved from GenBank (accession numbers are given in parentheses) and aligned with ClustalX (1.83) using the Neighbor Joining Method.

FIG. 4. Alignment of cyanobacterial protein sequences of *N. punctiforme* PAL (SEQ ID NO:2) and *A. variabilis* PAL (SEQ ID NO:4) with EncP PAL (SEQ ID. No. 5) and *P. putida* HAL (SEQ ID NO:6). Active site residues, which correspond to PAL or HAL activity, are highlighted and underlined.

FIG. 5. FIG. 5A: Protein sequence of *Anabaena variabilis* phenylalanine ammonia-lyase (PAL) with a cysteine to serine substitution at position 64 (AvPAL_C64S, SEQ ID NO:7); FIG. 5B: Protein sequence of *Anabaena variabilis* PAL with a cysteine to serine substitution at position 318 (AvPAL_C318S, SEQ ID NO:8); FIG. 5C: Protein sequence of *Anabaena variabilis* PAL with a cysteine to serine substitution at position 503 (AvPAL_C503S, SEQ ID NO:9); FIG. 5D: Protein sequence of *Anabaena variabilis* PAL with a cysteine to serine substitution at position 565 (AvPAL_C565S, SEQ ID NO:10); FIG. 5E: Protein sequence of *Anabaena variabilis* PAL with cysteine to serine substitutions at positions 503 and 565 (AvPAL_C565SC503S, SEQ ID NO:11). Cysteine to serine substitutions are underlined in bold.

FIG. 6. FIG. 6A: Effect of cysteine to serine substitutions at position 565 or both positions 565 and 503 of unpegylated AvPAL on in vitro PAL specific enzyme activity after incubation for various lengths of time at 37° C. FIG. 6B: Effect of cysteine to serine substitutions at position 565 or both positions 565 and 503 of pegylated AvPAL on in vitro PAL specific enzyme activity after incubation for various lengths of time at 37° C.

FIG. 7. FIG. 7A: Effect of cysteine to serine substitutions in AvPAL on formation of protein aggregates in solution as analyzed by gel electrophoresis under denaturing conditions (left panel) or native conditions (right panel). FIG. 7B: Effect of cysteine to serine substitutions in AvPAL on formation of protein aggregates in solution as analyzed by SEC-HPLC.

FIG. 8. Effect of cysteine to serine substitutions at positions 565 and 503 (dbl Mutant) in AvPAL on site-specific pegylation at various PEG concentrations.

FIG. 9. Effect of treatment of AvPAL with 0.05% Tween80 or 10 mM EDTA on formation of protein aggregates in solution as analyzed by SEC-HPLC.

FIG. 10. FIG. 10A: Effect of treatment of AvPAL by dithiotreitol (DTT) on formation of protein aggregates in solution as analyzed by SEC-HPLC. FIG. 10B: Effect of treatment of AvPAL by DTT and N-ethylmaleimide (NEM) on formation of protein aggregates in solution as analyzed by SEC-HPLC.

FIG. 11. Effect of phenylalanine (Phe) and trans-cinnamic acid (t-CA) as indicated on the enzyme activity of a pegylated AvPAL with cysteine to serine substitutions at positions 565 and 503 (AvPAL_C565SC503S) (rAV-PAL-PEG) stored for various times (days) at 4° C. (top panel), at 25° C. (middle panel) and at 37° C. (bottom panel).

FIG. 12. Effect of tyrosine (Tyr) at 1 and 5 mM as indicated on the enzyme activity of a pegylated AvPAL with cysteine to serine substitutions at positions 565 and 503 (AvPAL_C565SC503S) (rAV-PAL-PEG) stored for various times (days) at 4° C. (top panel), at 25° C. (middle panel) and at 37° C. (bottom panel).

FIG. 13. FIG. 13A: Effect of phenylalanine (Phe), benzoic acid and pyridoxamine, alone or in combination as indicated, on the enzyme activity of a pegylated AvPAL with cysteine to serine substitutions at positions 565 and 503 (AvPAL_C565SC503S) (rAV-PAL-PEG) stored for various times (weeks) at 4° C. (top panel) and at 37° C. (bottom panel). FIG. 13B: The chemical structures of benzoic acid (left), phenylalanine (middle) and trans-cinnamic acid (right) are depicted.

FIG. 14. FIG. 14A: Effect of a single subcutaneous injection of a pegylated AvPAL with cysteine to serine substitutions at positions 565 and 503 (AvPAL_C565SC503S) at 4 mg/kg (diamonds) and at 12 mg/kg (squares) into Cynomolgus monkeys on the plasma AvPAL_C565SC503S levels over time (hours). FIG. 14B: Effect of a single subcutaneous injection of AvPAL_C565SC503S at 4 mg/kg into Cynomolgus monkeys on the plasma AvPAL_C565SC503S (diamonds) and phenylalanine (squares) levels over time (hours).

FIG. 15. FIG. 15A: Effect of a single intravenous injection of a pegylated AvPAL with cysteine to serine substitutions at positions 565 and 503 (AvPAL_C565SC503S) at 1 mg/kg (diamonds), at 5 mg/kg (squares) and at 25 mg/kg (triangles) into rats on the plasma AvPAL_C565SC503S levels over time (hours). FIG. 15B: Effect of a single subcutaneous injection of AvPAL_C565SC503S at 10 mg/kg (diamonds), at 25 mg/kg (squares) and at 250 mg/kg (triangles) into rats on the plasma AvPAL_C565SC503S levels over time (hours)

FIG. 16. FIG. 16A: Effect of a pegylated AvPAL with cysteine to serine substitutions at positions 565 and 503 (AvPAL_C565SC503S) at 0.01, 0.1, 1, 10 and 100 μg/mL as indicated on proliferation (as measured by propidium iodide staining) of NOMO1 acute myeloid leukemia (AML) cells in vitro. FIG. 16B: Effect of AvPAL_C565SC503S at 0.1, 1, 10 and 100 μg/mL as indicated on proliferation of IM9 myeloma cells in vitro.

FIG. 17. FIG. 17A: Effect of a pegylated AvPAL with cysteine to serine substitutions at positions 565 and 503 (AvPAL_C565SC503S) at 0.01, 0.1, 1, 10 and 100 μg/mL as indicated on proliferation (as measured by propidium iodide staining) of SF268 (top) and 498L (bottom) brain/CNS tumor cells in vitro. FIG. 17B: Effect of AvPAL_C565SC503S at 0.01, 0.1, 1, 10 and 100 μg/mL as indicated on proliferation of HT29 (top) and HCT116 (bottom) colon tumor cells in vitro. FIG. 17C: Effect of AvPAL_C565SC503S at 0.01, 0.1, 1, 10 and 100 μg/mL as indicated on proliferation of H460 (top), 529L (middle) and 629L (bottom) lung tumor cells in vitro. FIG. 17D: Effect of AvPAL_C565SC503S at 0.01, 0.1, 1, 10 and 100 μg/mL as indicated on proliferation of LNCAP (top), PC3M (middle) and DU145 (bottom) prostate tumor cells in vitro.

DETAILED DESCRIPTION OF THE INVENTION

Several bacterial PAL have been already identified as part of the HAL/PAL family, including but not limited to PAL from *Streptomyces maritimus* (also known as EncP, SEQ ID NO:5, FIG. 4), PAL/HAL from *Nostoc punctiforme* (Accession ZP__00105927 from *Nostoc punctiforme* ATCC 29133, submitted Oct. 1, 2004, NCBI Microbial Genomes Annotation Project) (SEQ ID NO:2, FIG. 4), PAL/HAL from *Anabaena variabilis* (Gene ID 3679622, Ava__3988 phenylalanine/histidine ammonia-lyase, *Anabaena variabilis* ATCC 29413, Mar. 31, 2006) (SEQ ID NO:4, FIG. 4), the photosynthetic prokaryote *Anacystis nidulans* (Lofflehardt, Z. Naturforsch. 31(11-12):693-9 (1976)), the gram-negative bacteria from the family Enterobacteriaceae, *Photorabdus luminescens* TT01 (Williams, et al., Microbiology 151:2543-2550 (2005)), and *Streptomyces verticillatus* (Bezanson, et al., Can. J. Microbiol. 16(3):147-51 (1970)). Further, PAL activity has been evaluated in *Streptomyces maritimus* (Xiang, et al., J. Biol. Chem. 277:32505-32509 (2002)). Cyanobacteria, such as *Anabaena* and *Nostoc* have been studied with respect to their production of bioactive natural products that are generated via mixed polyketide-peptide biosynthetic pathways (Moore, Nat. Prod. Rep. 22(5):580-593 (2005); Becker, et al., Gene 325:35-42 (2004); Hoffman, et al., Gene 311:171-180 (2003)).

Although PAL is a ubiquitous higher plant enzyme that catalyzes the nonoxidative deamination of phenylalanine to cinnamic acid in the committed step to phenylpropanoid metabolites (Hahlbrock, et al., Annu. Rev. Plant Phys. Plant Mol. Biol. 40:347-369 (1989)), PAL has only been encountered in a few bacteria where it is involved in benzoyl-CoA biosynthesis in "*S. maritimus*" (Xiang, et al., J. Biol. Chem. 277:32505-32509 (2002)) and *Sorangium cellulosum* (Hill, et al., Chem. Commun. 1358-1359 (2003)) and in the biosynthesis of cinnamamide in *Streptomyces verticillatus* (Bezanson, et al., Can. J. Microbiol. 16:147-151 (1970)). The bacteriostatic agent enterocin is a natural product of the marine bacterium "*Streptomyces maritimus*" whose biosynthesis involves a number of unusual features (Hertweck, et al., Chem. Biol. 11:461-468 (2004); Piel, et al., Chem. Biol. 7:943-955 (2000); Piel, et al., J. Am. Chem. Soc. 122:5415-5416 (2000); Xiang, et al., Proc. Natl. Acad. Sci. USA 101: 15609-15614 (2004)). Among these is the formation of the rare polyketide synthase (PKS) starter unit benzoyl-coenzyme A (CoA) (Moore, et al., Nat. Prod. Rep. 19:70-99 (2002)). The initial biochemical reaction involves the conversion of the amino acid L-phenylalanine to trans-cinnamic acid by the novel bacterial phenylalanine ammonia-lyase (PAL, EC 4.3.1.5) EncP (Xiang, et al., J. Biol. Chem. 277: 32505-32509 (2002)). Activation of cinnamic acid to its CoA thioester followed by a single round of beta-oxidation yields benzoyl-CoA (Hertweck, et al., Chem. Bio. Chem. 2:784-786 (2001); Hertweck, et al., Tetrahedron 56:9115-9120 (2000); Xiang, et al., J. Bacteriol. 185:399-404 (2003)), which primes the enterocin type II PKS for chain extension with seven molecules of malonyl-CoA.

The first prokaryotic PAL-encoding gene (encP) (SEQ ID NO:5) was characterized and its role in de novo cinnamic acid and enterocin synthesis in "*S. maritimus*" was identified (Kalaitzis, et al., J. Am. Chem. Soc. 125:9290-9291 (2003); Xiang, et al., J. Biol. Chem. 277:32505-32509 (2002)). The encP gene encodes a 522 amino acid protein that is considerably smaller than eukaryotic PALs by nearly 200 amino acid residues. Although sequence homologous to plant PALs such as from *Petroselinum crispum* (Röther, et al., Eur. J. Biochem. 269:3065-3075 (2002)) (CAA57056, 30% identical and 48% similar), it rather shares greater homology to bacterial histidine ammonia-lyases (HALs, EC 4.3.1.3) such as from *Pseudomonas putida* (Schwede, et al., Biochemistry 27:5355-5361 (1999)) (A35251, 36% identical and 54% similar, SEQ ID NO:6, FIG. 4) and to tyrosine ammonia-lyase (TAL) from *Rhodobacter capsulatus* (Kyndt, et al., FEBS Lett. 512:240-244 (2002)) (FIG. 3). The homology includes the conserved active site serine residue at position 143 of the phenylalanine/histidine/tyrosine family of ammonia-lyases that is the probable precursor of the modified dehydroalanine residue in the 4-methylideneimidazole-5-one (MIO) prosthetic group (anger, et al., Adv. Prot. Chem. 58:175-188 (2001); Poppe, Curr. Opin. Chem. Biol. 5:512-524 (2001); Schwede, et al., Biochemistry 27:5355-5361 (1999)). EncP shares greatest sequence homology to AdmH (AA039102, 63% identical and 76% similar), a putative phenylalanine aminomutase involved in andrimid biosynthesis in *Pantoea agglomerans* that is related to the tyrosine aminomutase Sgc4 from *Streptomyces globisporus* (Christenson, et al., J. Am. Chem. Soc. 125:6062-6063 (2003); Christenson, et al., Biochemistry 42:12708-12718 (2003)).

HAL and PAL were shown to share in common a mechanism for the chemically difficult elimination of ammonia from histidine and phenylalanine, respectively. With both enzymes, a superelectrophilic prosthetic group 5 methylene-3,5-dihydroimidazol-4-one (MIO) activates the non-acidic beta hydrogen atoms of their respective substrates by a Friedel-Crafts-type attack at the aromatic ring. The sigma complex that is generated prevents the extraction of protons from the ring by excluding any bases from access to the binding pocket of the enzyme. The formation of an exocyclic double bond is key in the elimination of ammonia, rearomatization, and fragmentation. The prosthetic MIO group is regenerated and the product urocanate or cinnamate is formed (Poppe, et al., Angew. Chem. Int. Ed. 44:3668-3688 (2005)).

Because of the high homology between HAL and PAL, the conserved regions of HAL and PAL are referred to HAL/PAL conserved region. This high homology can create some ambiguities in databases like NCBI on the potential enzyme activity of a "PAL-HAL" protein conducting to mislabeling, such as with protein sequences listed in the NCBI database for *Nostoc punctiforme* and *Anabaena variabilis*. Therefore some PAL enzymes can be mislabeled HAL enzymes. Although the active sites of PALs and HALs are very similar, they are predicted to differ in some key residues (Calabrese et al., Biochemistry 43(36):11403-11416 (2004); Xiang et al., (2002) ibid.; Williams et al., (2005) ibid.). Particularly in HAL, the methionine 383 and glutamic acid 415 from *Pseudomonas putida* (SEQ ID NO:6) are highly conserved in all HALs but are always replaced in all the PALs described so far (eukaryotic or prokaryotic) by lysine and glutamine respectively (FIG. 4). So it can be said that all proteins with a "PAL-HAL"' region and having the homologues of lysine 383 and glutamic acid 415 have the sequence signature of a protein with PAL activity. This relatively newly described PAL signature (Williams et al., (2005), ibid.) allows to label properly some enzymes from HAL to PAL and could be used to identify some new PAL enzymes from already published genes and proteins database.

The present invention relates to compositions of such prokaryotic PAL and biologically active fragments, mutants, variants or analogs thereof and their use for therapeutic purposes, including the treatment of cancer.

A. Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. Definition of standard chemistry terms may be found in reference works, including Carey and Sundberg, Advanced Organic Chemistry, 3$^{rd}$ Edition, Vols. A and B (Plenum Press, New York 1992). The practice of the present invention will employ, unless otherwise indicated, conventional methods of synthetic organic chemistry, mass spectroscopy, preparative and analytical methods of chromatography, protein chemistry, biochemistry, recombinant DNA techniques and pharmacology, within the skill of the art. See, e.g., T. E. Creighton, Proteins: Structures and Molecular Properties (W.H. Freeman and Company, 1993); A. L. Lehninger, Biochemistry (Worth Publishers, Inc., 4$^{th}$ Edition, 2004); Sambrook, et al., Molecular Cloning: A Laboratory Manual (2$^{nd}$ Edition, 1989); Methods In Enzymology (S. Colowick and N. Kaplan eds., Academic Press, Inc.); Remington's Pharmaceutical Sciences, 18$^{th}$ Edition (Easton, Pa.: Mack Publishing Company, 1990).

All publications, patents and patent applications cited herein, whether supra or infra, are hereby incorporated by reference in their entirety.

The following amino acid abbreviations are used throughout the text:

Alanine: Ala (A)

Asparagine: Asn (N)

Cysteine: Cys (C)

Glutamic acid: Glu (E)

Histidine: His (H)

Leucine: Leu (L)
Methionine: Met (M)
Proline: Pro (P)
Threonine: Thr (T)
Tyrosine: Tyr (Y)
Arginine: Arg (R)
Aspartic acid: Asp (D)
Glutamine: Gln (Q)
Glycine: Gly (G)
Isoleucine: Ile (I)
Lysine: Lys (K)
Phenylalanine: Phe (F
Serine: Ser (S)
Tryptophan: Trp (W)
Valine: Val (V)

"Polynucleotide" refers to a polymer composed of nucleotide units. Polynucleotides include naturally occurring nucleic acids, such as deoxyribonucleic acid ("DNA") and ribonucleic acid ("RNA") as well as nucleic acid analogs. Nucleic acid analogs include those which include non-naturally occurring bases, nucleotides that engage in linkages with other nucleotides other than the naturally occurring phosphodiester bond or which include bases attached through linkages other than phosphodiester bonds. Thus, nucleotide analogs include, for example and without limitation, phosphorothioates, phosphorodithioates, phosphorotriesters, phosphoramidates, boranophosphates, methylphosphonates, chiral-methyl phosphonates, 2-O-methyl ribonucleotides, peptide-nucleic acids (PNAs), and the like. Such polynucleotides can be synthesized, for example, using an automated DNA synthesizer. The term "nucleic acid" typically refers to large polynucleotides. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

"cDNA" refers to a DNA that is complementary or identical to an mRNA, in either single stranded or double stranded form.

Conventional notation is used herein to describe polynucleotide sequences: the left-hand end of a single-stranded polynucleotide sequence is the 5'-end; the left-hand direction of a double-stranded polynucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand"; sequences on the DNA strand having the same sequence as an mRNA transcribed from that DNA and which are located 5' to the 5'-end of the RNA transcript are referred to as "upstream sequences"; sequences on the DNA strand having the same sequence as the RNA and which are 3' to the 3' end of the coding RNA transcript are referred to as "downstream sequences."

"Complementary" refers to the topological compatibility or matching together of interacting surfaces of two polynucleotides. Thus, the two molecules can be described as complementary, and furthermore, the contact surface characteristics are complementary to each other. A first polynucleotide is complementary to a second polynucleotide if the nucleotide sequence of the first polynucleotide is identical to the nucleotide sequence of the polynucleotide-binding partner of the second polynucleotide. Thus, the polynucleotide whose sequence 5'-TATAC-3' is complementary to a polynucleotide whose sequence is 5'-GTATA-3'.

A nucleotide sequence is "substantially complementary" to a reference nucleotide sequence if the sequence complementary to the subject nucleotide sequence is substantially identical to the reference nucleotide sequence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant polynucleotide" refers to a polynucleotide having sequences that are not naturally joined together. An amplified or assembled recombinant polynucleotide may be included in a suitable vector, and the vector can be used to transform a suitable host cell. A host cell that comprises the recombinant polynucleotide is referred to as a "recombinant host cell." The gene is then expressed in the recombinant host cell to produce, e.g., a "recombinant polypeptide." A recombinant polynucleotide may serve a non-coding function (e.g., promoter, origin of replication, ribosome-binding site, etc.) as well.

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. Primers can be labeled with, e.g., chromogenic, radioactive, or fluorescent moieties and used as detectable moieties.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer. The term "protein" typically refers to large polypeptides. The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

"Conservative substitution" refers to the substitution in a polypeptide of an amino acid with a functionally similar amino acid. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Amino acids may also be grouped as follows:

(1) hydrophobic: Met, Ala, Val, Leu, Ile;
(2) neutral hydrophilic: Cys, Ser, Thr;
(3) acidic: Asp, Glu;
(4) basic: Asn, Gln, His, Lys, Arg;
(5) residues that influence chain orientation: Gly, Pro; and
(6) aromatic: Trp, Tyr, Phe.

The terms "identical" or percent "identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using a sequence comparison algorithm described in prior co-pending U.S. patent application Ser. No. 11/230,374 filed on Sep. 19, 2005, which is herein incorporated by reference in its entirety, or by visual inspection.

The phrase "substantially homologous" or "substantially identical" in the context of two nucleic acids or polypeptides, generally refers to two or more sequences or subsequences that have at least 40%, 60%, 80%, 90%, 95%, 98% nucleotide or amino acid residue identity, when compared and aligned for maximum correspondence, as measured using one of the following sequence comparison algorithms or by visual inspection. Preferably, the substantial identity exists over a region of the sequences that is at least about 50 residues in length, more preferably over a region of at least about 100 residues, and most preferably the sequences are substantially identical over at least about 150 residues. In a most preferred embodiment, the sequences are substantially identical over the entire length of either or both comparison biopolymers.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the prokaryotic PAL variant compositions of the invention are substantially pure or isolated. In some embodiments, the prokaryotic PAL variant compositions of the invention are substantially pure or isolated with respect to the macromolecular starting materials used in their synthesis. In some embodiments, the pharmaceutical compositions of the invention comprise a substantially purified or isolated prokaryotic PAL variant admixed with one or more pharmaceutically acceptable excipient.

"Naturally occurring" as applied to an object refers to the fact that the object can be found in nature. For example, a polypeptide or polynucleotide sequence that is present in an organism (including viruses) that can be isolated from a source in nature and which has not been intentionally modified by man in the laboratory is naturally occurring.

"Wild-type" (wt) is a term referring to the natural genetic form of an organism. A wild-type is distinguished from a mutant form (an organism with a genetic mutation).

The terms "polypeptide" and "protein" refer to a polymer of amino acid residues and are not limited to a minimum length of the product. Thus, peptides, oligopeptides, dimers, multimers, and the like, are included within the definition. Both full-length proteins and fragments thereof are encompassed by the definition. The terms also include postexpression modifications of the polypeptide, for example, glycosylation, acetylation, phosphorylation and the like. Furthermore, for purposes of the present invention, a "polypeptide" refers to a protein, which includes modifications, such as deletions, additions and substitutions (generally conservative in nature), to the native sequence, so long as the protein maintains the desired activity. Such polypeptides may be referred to as "mutants" herein. These modifications may be deliberate, as through site-directed mutagenesis, or may be accidental, such as through mutations arising with hosts that produce the proteins or errors due to PCR amplification.

As used herein, "variant," "analog," or "derivative" is a compound, e.g., a peptide, having more than about 70% sequence but less than 100% sequence similarity with a given compound, e.g., a peptide. Such variants, analogs or derivatives may be comprised of non-naturally occurring amino acid residues, including by way of example and not limitation, homoarginine, ornithine, penicillamine, and norvaline, as well as naturally occurring amino acid residues. Such variants, analogs or derivatives may also be composed of one or a plurality of D-amino acid residues, and may contain non-peptide interlinkages between two or more amino acid residues.

As used herein, the "ratio" of a PAL polypeptide (e.g., AvPAL) and a water-soluble polymer (e.g., polyethylene glycol or PEG) refers to the reaction condition molar ratio between the PAL polypeptide and the water-soluble polymer. For example, a ratio of about 1:3 for AvPAL and polyethylene glycol (1:3 AvPAL:PEG) means that the chemically modified PAL was produced in a reaction condition with about 1 mol AvPAL per 3 mol of polyethylene glycol. Under the reaction conditions described in EXAMPLE 6, infra, a ratio of about 1:3 AvPAL:PEG results in about 10-12 mol PEG per mol AvPAL monomer.

"Treatment" or "treating" as used herein refers to prophylactic treatment or therapeutic treatment or diagnostic treatment.

A "prophylactic" treatment is a treatment administered to a subject who does not exhibit signs of disease or pathology, i.e., a cancer, or exhibits only early signs for the purpose of decreasing the risk of developing pathology. The prokaryotic PAL compositions of the invention may be given as a prophylactic treatment to reduce the likelihood of developing pathology, i.e., a cancer, or to minimize the severity of the pathology, if developed.

A "therapeutic" treatment is a treatment administered to a subject who exhibits signs or symptoms of pathology, i.e., a cancer, for the purpose of diminishing or eliminating those signs or symptoms. The signs or symptoms may be biochemical, cellular, histological, functional, subjective or objective. The prokaryotic PAL compositions of the invention may be given as a therapeutic treatment or for diagnosis.

"Diagnostic" means identifying the presence or nature of a pathologic condition, i.e., a cancer. Diagnostic methods differ in their specificity and selectivity. While a particular diagnostic method may not provide a definitive diagnosis of a condition, it suffices if the method provides a positive indication that aids in diagnosis.

"Pharmaceutical composition" refers to a composition suitable for pharmaceutical use in subject animal, including humans and mammals. A pharmaceutical composition comprises a pharmacologically effective amount of a prokaryotic PAL polypeptide and also comprises a pharmaceutically acceptable carrier. A pharmaceutical composition encompasses a composition comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a prokaryotic PAL polypeptide of the present invention and a pharmaceutically acceptable carrier.

"Pharmaceutically acceptable carrier" refers to any of the standard pharmaceutical excipients, vehicles, diluents, stabilizers, preservatives, solubilizers, emulsifiers, adjuvants and/or carriers, such as, for example and not for limitation, a phosphate buffered saline solution, 5% aqueous solution of dextrose, and emulsions, such as an oil/water or water/oil emulsion, and various types of wetting agents and/or adjuvants. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous or intraperitoneal injection; or topical, transdermal, or transmucosal administration). A "pharmaceutically acceptable salt" is a salt that can be formulated into a prokaryotic PAL variant composition for pharmaceutical use including, e.g., metal salts (sodium, potassium, magnesium, calcium, etc.) and salts of ammonia or organic amines.

By "pharmaceutically acceptable" or "pharmacologically acceptable" is meant a material which is not biologically or otherwise undesirable, i.e., the material may be administered to an individual without causing any undesirable biological effects or interacting in a deleterious manner with any of the components of the composition in which it is contained.

The term "unit dosage form," as used herein, refers to physically discrete units suitable as unitary dosages for human and animal subjects, each unit containing a predetermined quantity of prokaryotic PAL variant of the present invention calculated in an amount sufficient to produce the desired effect in association with a pharmaceutically acceptable diluent, carrier or vehicle. The specifications for the novel unit dosage forms of the present invention depend on the particular prokaryotic PAL variant employed and the effect to be achieved, and the pharmacodynamics associated with each prokaryotic PAL variant in the host.

By "physiological pH" or a "pH in the physiological range" is meant a pH in the range of approximately 7.2 to 8.0 inclusive, more typically in the range of approximately 7.2 to 7.6 inclusive.

As used herein, the term "subject" encompasses mammals and non-mammals. Examples of mammals include, but are not limited to, any member of the mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish, and the like. The term does not denote a particular age or gender.

B. Prokaryotic PAL Variants

The elucidation of a reliable three-dimensional structure or structural model for a specific macromolecule permits rational design to become a productive method for optimization of specific structure and/or function of said macromolecule. Methods of using a three-dimensional structure or structural model for optimizing PAL enzymes are described in prior co-pending U.S. patent application Ser. No. 11/230,374 filed on Sep. 19, 2005, which is herein incorporated by reference in its entirety. A high-resolution three-dimensional protein crystal structure of a prokaryotic PAL may be used in methods involving protein engineering to improve the biochemical and biophysical properties of a prokaryotic PAL, and to increase the in vivo therapeutic effectiveness of a prokaryotic PAL. The invention contemplates prokaryotic PAL variants with greater phenylalanine-converting activity and/or reduced immunogenicity as compared to a wild-type prokaryotic PAL. The invention also contemplates prokaryotic PAL variants with greater biochemical stability and/or biochemical half-life as compared to a wild-type prokaryotic PAL.

Prokaryotic PAL Variants with Enhanced Catalytic Activity

The biologically active sites of a wild-type prokaryotic PAL according to the invention may be modified as desired to optimize PAL kinetic characteristics. Km, the concentration of substrate that gives half-maximal activity, is intimately associated with the therapeutic efficacy of PAL in maintaining Phe levels within an acceptable range, i.e., from below the level of detection to between about 20 μM to 60 μM, preferably to less than about 20 μM, and even more preferably to less than about 10 μM, using standard detection methods well known in the art. Km is the affinity of the enzyme for the substrate. By controlling affinity, one can limit or control the efficacy of any enzyme against substrate at different concentrations. For example, if Km is 1000 μM (e.g., PAL from *Rhodosporidium toruloides*), the activity of the enzyme will be reduced to about 12.5% at blood Phe levels of 240 μM and to about 3% at blood Phe levels of 60 μM. If Km is 240 μM, the activity of the enzyme will be reduced to about 50% at blood Phe levels of 240 μM and to about 12% at blood Phe levels of 60 μM. A preferred therapeutic objective would be to have a prokaryotic PAL enzyme with sufficient activity to reduce but also maintain Phe levels upon treatment within the range from below the level of detection to between about 20 μM to 60 μM, preferably to less than about 20 μM, and even more preferably to less than about 10 μM, using standard detection methods well known in the art. An enzyme with a Km of about 1000 μM will lose activity rapidly as Phe levels drop to within normal range (approximately 55-60 μM, see Kaufmann, Proc. Natl. Acad. Sci USA 96:3160-3164 (1999)) and will also require the impractical administration of highly concentrated or large volumes of doses. An enzyme with a lower Km may rapidly deplete Phe and maintain Phe levels upon treatment within a range from below the level of detection to between about 20 μM to 60 μM, preferably to less than about 20 μM, and even more preferably to less than about 10 μM, which may be useful in the management of cancer.

In preferred embodiments, the biologically active prokaryotic PAL variant has a kcat of at least about 0.1 $s^{-1}$, preferably greater than about 0.5 $s^{-1}$, and even more preferably greater than about 1.0 $s^{-1}$. In most preferred embodiments, the biologically active prokaryotic PAL variant has a kcat of at least about 0.4 $s^{-1}$, preferably greater than about 2.0 $s^{-1}$, and even more preferably greater than about 4.0 $s^{-1}$. In other preferred embodiments, the biologically active prokaryotic PAL variant has a Km of between about 10 μM to about 2000 μM. In more preferred embodiments, the biologically active prokaryotic PAL variant has a Km of between about 10 μM to about 1000 μM. In even more preferred embodiments, the biologically active prokaryotic PAL variant has a Km of between about 10 μM to about 500 μM. In other preferred embodiments, the biologically active prokaryotic PAL variant exhibits enzymatic activity from about 50% of to about 10-fold times greater than the wild-type PAL. In other preferred embodiments, the biologically active prokaryotic PAL variant exhibits enzymatic activity from about 50% of to about 100% higher than the wild-type PAL. Such biological active prokaryotic PAL variants may be formed using methods well known in the art, such as by site-directed mutagenesis.

Prokaryotic PAL Variants Having Reduced Immunogenicity

A number of strategies are currently used to reduce protein immunogenicity. Preferably, modifications that are introduced to minimize the immune response do not destroy the structure, function, or stability of the macromolecule. Effective strategies used include increasing human sequence content (chimeras and/or other 'humanization' approaches), improving solution properties, removing antibody epitopes, introducing chemical derivatization (such as pegylation), and/or identifying and removing MHC agretopes. For an injected therapeutic, in vivo immunoreactivity can be addressed by performing epitope mapping followed by rational mutagenesis to modify and/or otherwise mutate these sites of immunogenicity, alone and in combination with site-specific pegylation (Hershfield, et al., Proc. Natl. Acad. Sci. USA 88:7185-7189 (1991); Leong, et al., Cytokine 16(3): 106-119 (2001); Lee, et al., Pharm. Res. 20(5):818-825 (2003)) or other chemical derivatization methods to reduce protein immunoreactivity to an acceptable level. Modification of antigenic surface protein regions reduces immunogenicity (Chirino, et al., Drug Discov. Today 9(2):82-90 (2004)). One method of improvement involves the construction of smaller sized proteins that retain catalytic activity (e.g., an absorbance assay is used for activity measurement). Protein engineering coupled to ELISA screening, can also be used to identify mutants with reduced immunoreactivity. Another method introduces point mutations for additional surface Lys sites for pegylation derivatization, a method shown to reduce immunogenicity with the test enzyme purine nucleoside phosphorylase (Hershfield, et al. (1991), ibid.). An alternative pathway uses mutation of residues located in protein epitope regions to remove immunogenic sites (Yeung, et al., J. Immunol. 172(11):6658-6665 (2004)). In an approach that is analogous to antibody humanization, homologous loop regions and/or residues from human antibodies are substituted into the corresponding loop regions of a homologous protein.

Improving solution properties of proteins may increase specific enzyme activity and/or reduce immunogenicity. One solution property typical of bacterially expressed recombinant proteins is the formation of protein aggregates due, for example, to inter-chain disulfide bind formation, hydrophobic interactions and/or divalent cations (Chi, et al., Pharm. Res. 20(9):1325-1336 (2003)). Aggregation of recombinantly expressed proteins can enhance the immune response (Hermeling, et al., Pharm. Res. 21(6):897-903 (2994); Schellekens, Nephrol. Dial. Transplant. 20(suppl 6):vi3-9 (2005)). One method of improvement involves substituting surface cysteine residues with other amino acid residues (e.g., serine) to minimize the possibility of formation of inter-chain disulfide bonds. For example, substitution of two surface cysteine residues with serine residues reduced the aggregation of chorismate lyase with minor effects on enzyme activity (Holden, et al., Biochim. Biophys. Acta 1594(1):160-167 (2002)). The invention contemplates prokaryotic PAL variants having one or more cysteine residues substituted by another amino acid residue, preferably a serine residue. In some embodiments, one or more cysteine residues of the prokaryotic PAL are substituted by another amino acid residue. In preferred embodiments, the prokaryotic PAL is AvPAL. In more preferred embodiments, one or more cysteine residues of AvPAL are substituted by a cysteine residue.

C. Chemically Modified Prokaryotic PAL Variants

Macromolecule chemical modification can be performed in a non-specific fashion (leading to mixtures of derivatized species) or in a site-specific fashion (based on wild-type macromolecule reactivity-directed derivatization and/or site-selective modification using a combination of site-directed mutagenesis and chemical modification) or, alternatively, using expressed protein ligation methods (Hofmann, et al., Curr. Opin. Biotechnol. 13(4):297-303 (2002)). Preferably, chemical modification is used to reduce immunogenicity. Pegylation is a demonstrated method to reduce immunogenicity of proteins (Bhadra, et al., Pharmazie 57(1):5-29 (2002)), but glycosylation and other chemical derivatization procedures, using modification with phosphorylation, amidation, carboxylation, acetylation, methylation, creation of acid-addition salts, amides, esters, and N-acyl derivatives are also possible (Davis, Science 303:480-482 (2004)). Methods for pegylating PAL proteins and for determining the optimal degree of pegylation are described in prior co-pending U.S. patent application Ser. No. 11/230,374 filed on Sep. 19, 2005, which is herein incorporated by reference in its entirety. The invention contemplates prokaryotic PAL variants comprising a water-soluble polymer (i.e., polyethylene glycol or PEG).

The invention contemplates introducing one or more lysine residues at/near the active site of a prokaryotic PAL variant to enhance catalytic activity, reduce immunogenicity and/or improve biochemical stability, in part by blocking potential pegylation of other amino acid residues (e.g., tyrosine) at/near the active site of the enzyme or by blocking potential pegylation of a lysine residue important for enzyme activity. Without being bound to a particular theory, it is hypothesized that a tyrosine residue at/near the active site of a prokaryotic PAL (i.e., position 78 or 314 in AvPAL) can be a site for pegylation, which reduces enzyme activity. In some embodiments, one or more amino acid residues at/near the active site of the prokaryotic PAL, which are not required for enzyme activity, are substituted by a lysine residue. In a preferred embodiment, the prokaryotic PAL is AvPAL. In a more preferred embodiment, the AvPAL tyrosine residue at position 78 or 314 is not accessible for pegylation. Again without being bound to a particular theory, it is hypothesized that a lysine residue of a prokaryotic PAL (i.e., position 419 in AvPAL), which is normally blocked from pegylation due to pegylation of a neighboring lysine residue PAL (i.e., position 413 in AvPAL), can be a site for pegylation, which reduces substrate binding and/or catalytic activity. In some embodiments, one or more amino acid residues of the prokaryotic PAL are substituted by a lysine residue residue, such that a lysine residue important for the enzyme's substrate binding and/or catalytic activity is not accessible for pegylation. In a preferred embodiment, the prokaryotic PAL is AvPAL. In a more preferred embodiment, the AvPAL lysine residue at position 419 is not accessible for pegylation.

Pegylated Prokaryotic PAL Variants

Examples 7 through 9 of prior co-pending U.S. patent application Ser. No. 11/451,999 filed on Jun. 12, 2006, which is herein incorporated by reference in its entirety, describe the effects of pegylated and nonpegylated forms of lysine mutant R91K PAL from *Rhodosporidium toruloides* (RtPAL), PAL produced by the cyanobacterium *Nostoc punctiforme* (NpPAL), and PAL produced by the cyanobacterium *Anabaena variabilis* (AvPAL) on phenylalanine (Phe) levels in the ENU2 or $BTBR^{enu2}$ mouse. This animal model is a homozygous mutant at the phenylalanine hydroxylase gene (PAH) locus resulting in an animal with severe hyperphenylalanemia. The high plasma Phe levels make this animal the appropriate model for evaluating the ability of PAL to reduce plasma Phe. Administration of pegylated forms of NpPAL and AvPAL resulted in greater reduction in Phe in the ENU2 mice as compared to unpegylated NpPAL and AvPAL, respectively. Such effects were maintained for NpPAL upon weekly injections over a ten-week period. These results show that pegylation of PAL from the cyanobacteria, *Nostoc punctiforme* and *Anabaena variabilis*, is essential in reducing Phe levels in PKU affected mice.

Example 14 of prior co-pending U.S. patent application Ser. No. 11/451,999 filed on Jun. 12, 2006, which is herein incorporated by reference in its entirety, describe the effect of serine substitution of the cysteine residues (e.g., at positions 503 and 565) in the AvPAL polypeptide on Phe levels in ENU2 mice. The administration of the pegylated AvPAL double cysteine mutant AvPAL_C565SC503S resulted in a reduction in plasma Phe that was comparable to that achieved with pegylated wild-type AvPAL. In addition, the anti-PAL antibody titers were lower in animals injected with pegylated AvPAL variant as compared to pegylated wild-type AvPAL. These results show that a pegylated AvPAL variant has (1) in vivo PAL enzyme activity that is comparable to the pegylated wild-type AvPAL, and (2) has reduced immunogenicity compared to the pegylated wild-type AvPAL.

D. Therapeutic Uses and Administration of Prokaryotic PAL Variants

1. Various Forms of Cancer

The present invention is directed to the treatment of cancer with methods that comprise the use of prokaryotic PAL compositions, either alone or in combination with other therapeutic regimens, for example and not for limitation, cancer therapeutic agents or targeted cancer therapeutic agents. In particular, it is contemplated that prokaryotic PAL compositions may be used to treat that patient population with blood, serum or plasma, phenylalanine (Phe) concentrations at any level (e.g., from about 40 μM to and 2000 μM), where the normal range in human plasma is between about 55 μM and 60 μM (Kaufman, Proc. Natl. Acad. Sci. USA 96:3160-3164 (1999)).

A "cancer therapeutic agent" as used herein refers to any compound, e.g., small molecule or peptide/polypeptide, which has been shown to exert a therapeutic effect (i.e., inhibition of proliferation and/or survival) on cancer cells. Typically, the cancer therapeutic agent is a cytotoxic agent or a cytostatic agent.

A "targeted cancer therapeutic agent" as used herein refers to any compound, e.g., small molecule or peptide/polypeptide, or polypeptide or conjugated polypeptide that has been shown to exert a therapeutic effect (i.e., inhibition of proliferation and/or survival) on specific cancer cells or tissues. Typically, the targeted cancer therapeutic agent is an antibody, a polypeptide having an antibody-like domain, or other polypeptide, e.g., enzyme, hormone, growth factor, cytokine, etc., which selectively binds to the surface of a target cell. The antibody, polypeptide having an antibody-like domain, or other polypeptide may be unconjugated or may be conjugated to a cancer therapeutic agent. The targeted cancer therapeutic agent can be a compound that exerts a therapeutic effect on specific cancer cells or tissues.

The prokaryotic PAL compositions of the present invention are useful for treating any cancer for which Phe restriction or depletion inhibits its proliferation and/or survival. The identification of cancers for which treatment with the prokaryotic PAL compositions of the present invention may be useful can be made on the basis of in vitro culture experiments (see EXAMPLE 14) or in vivo human tumor xenograft studies in mice (see EXAMPLE 15) using, for example, a tumor biopsy specimen, or by comparison with tumor types with known or demonstrated sensitivity to Phe restriction or depletion in animal models of human cancer. In preferred embodiments, the cancer is lung cancer, brain or central nervous system cancer, colon cancer, prostate cancer, renal cancer or metastatic melanoma. In other preferred embodiments, the cancer is head and neck cancer, uterine cancer, leukemia (e.g., acute myeloid leukemia or acute lymphoblastic leukemia) or myeloma. In other preferred embodiments, the cancer is pediatric cancer or a resistant cancer (i.e., a cancer that has been shown to be resistant to cancer therapeutic agents or targeted cancer therapeutic agents).

Certain embodiments of the present invention are directed to treating cancer by administering to the subject a composition comprising prokaryotic PAL or a biologically active fragment, mutant, variant or analog thereof in combination with a protein-restricted (i.e., phenylalanine-free) diet, wherein the combined administration of the prokaryotic PAL and the protein-restricted diet is effective to lower the Phe concentration in the blood, plasma or serum of said subject as compared to the concentration in the absence of said combined administration.

It is contemplated that the methods of the invention will entail monitoring the plasma Phe concentration of the individual to be treated by prokaryotic PAL compositions. The patient is then treated by administering prokaryotic PAL compositions alone, or in combination with other therapeutic regimens, such as cancer therapeutic agents or targeted cancer therapeutic agents, or a combined regimen of prokaryotic PAL and a protein-restricted (i.e., phenylalanine-free) diet, such that there is produced at least a 10% decrease in the blood, plasma or serum Phe concentrations of the patient. Preferably, the method will produce at least a 25%, and more preferably at least a 50% decrease in the blood, plasma or serum Phe concentration. Even more preferably, the method will produce at least a 50%, 60%, 70%, 80%, 90%, 95% or greater decrease in the blood, serum or plasma Phe concentration of the individual (for example, where a patient with a plasma Phe concentration of 60 μM is treated, a 50%, 70% or 90% decrease in the Phe concentration will produce a plasma Phe concentration of 30 μM, 18 μM or 6 μM, respectively). Of course, it should be understood that the treatment methods of the present invention should attempt to lower the blood, serum or plasma Phe concentrations of the patient upon treatment to a range from below the level of detection to between about 20 μM to 60 μM, preferably to less than about 20 μM, and even more preferably to less than about 10 μM, using standard detection methods well known in the art.

Parenteral, oral, or other standard routes of administration and dosage can be achieved using standard methods.

2. Compositions for Use in the Treatment

The present invention contemplates therapeutic intervention of cancer. Such intervention is based initially on the use of prokaryotic PAL compositions, pharmaceutical compositions and formulations, which may be used alone or in combination with other therapeutic regimens, such as cancer therapeutic agents or targeted cancer therapeutic agents, or a combined regimen of a low protein diet (i.e., low phenylalanine) and prokaryotic PAL, or both. Further, prokaryotic PAL and/or dietary restrictions may be further combined with other therapeutic compositions that are designed, for example, to combat manifestations of low phenylalanine levels, such as, for example and not for limitation, tyrosine supplementation. This section provides a discussion of the compositions, pharmaceutical compositions and formulations that may be used in the treatments contemplated herein.

Prokaryotic PAL Compositions, Pharmaceutical Compositions and Formulations

In general, the present invention contemplates pharmaceutical compositions comprising therapeutically effective amounts of prokaryotic PAL compositions of the invention together with one or more pharmaceutically acceptable excipients, vehicles diluents, stabilizers, preservatives, solubilizers, emulsifiers, adjuvants and/or carriers. Such pharmaceutical compositions include diluents of various buffer content (e.g., Tris-HCl, phosphate), pH and ionic strength; additives such as detergents and solubilizing agents (e.g., Polysorbate 20, Polysorbate 80), anti-oxidants (e.g., ascorbic acid, sodium metabisulfite), preservatives (e.g., Thimerosol, benzyl alcohol) and bulking substances (e.g., lactose, mannitol); see, e.g., Remington's Pharmaceutical Sciences, $18^{th}$ Edition (1990, Mack Publishing Co., Easton, Pa.) pages 1435:1712, which are herein incorporated by reference. An effective amount of active ingredient is a therapeutically, prophylactically, or diagnostically effective amount, which can be readily determined by a person skilled in the art by taking into consideration such factors as body weight, age, and therapeutic goal.

The prokaryotic PAL pharmaceutical compositions of the present invention may include a buffering agent to maintain the pH of the solution within a desired range. Preferred buffering agents include Tris-HCl, sodium acetate, sodium phosphate, and sodium citrate. Mixtures of these buffering agents may also be used. The amount of buffering agent useful in the composition depends largely on the particular buffer used and the pH of the solution. For example, acetate is a more efficient buffer at pH 5 than pH 6 so less acetate may be used in a solution at pH 5 than at pH 6. A more preferred buffering agent is Tris-HCl. A preferred pH range for the pharmaceutical compositions of the present invention is about pH 6.0-8.5. A more preferred pH range for the pharmaceutical compositions of the present invention is about pH 7.0-8.0. A most preferred pH range for the pharmaceutical compositions of the present invention is about pH 7.0-7.6.

The pharmaceutical compositions of the present invention may further include an isotonicity-adjusting agent to render the solution isotonic and more compatible for injection. A preferred agent is sodium chloride within a concentration range of 50-200 mM. A more preferred agent is sodium chloride within a concentration range of 100-150 mM. A most preferred agent is sodium chloride within a concentration range of 130-150 mM.

Pharmaceutically acceptable carriers or excipients may include stabilizers, which are molecules that stabilize the prokaryotic PAL compositions of the invention. The term "stabilize" as used herein, is meant to include, for example and not for limitation, increasing the shelf-life of a prokaryotic PAL enzyme, protecting the prokaryotic PAL enzyme from proteolytic digestion, maintaining the prokaryotic PAL enzyme in an active conformation, and preserving the prokaryotic PAL enzyme activity upon storage at elevated temperatures.

Stabilizers of the present invention include L-phenylalanine (Phe) and structural analogs thereof, such as trans-cinnamic acid (t-CA), benzoic acid, tyrosine (Tyr), and the like. Loss of activity of a plant PAL from *Phaseolus vulgaris* (PvPAL) has been shown upon removal of its substrate L-phenylalanine after affinity purification (Da Cunha, Eur. J. Biochem. 178:243-248 (1988)), and a yeast PAL from *Rhodosporidium toruloides* (RtPAL) has been shown to be protected from protease inactivation by tyrosine (Wang, et al., Mol. Genet. Metab. 86:134-140 (2005); Pilbak, et al., FEBS J. 273:1004-1019 (2006)). As shown herein below, Phe and certain of its structural analogs have the ability to stabilize PEG:PAL conjugates of a prokaryotic PAL from *Anabaena variabilis* (AvPAL) (see EXAMPLE 11). Without being bound to a particular theory, it is hypothesized that the prokaryotic PAL enzyme is more stable as an enzyme-substrate complex, wherein the bound substrate Phe is converted to the product t-CA or to a transition state analog of t-CA. The t-CA remains bound to the otherwise highly reactive active site center (MIO group), thereby stabilizing the PAL enzyme. Accordingly, the PAL enzyme substrate, Phe, product, t-CA, or structural analogs thereof are stabilizers of the invention.

The invention contemplates a pharmaceutical composition comprising a prokaryotic PAL variant and a pharmaceutically acceptable carrier, wherein the pharmaceutically acceptable carrier comprises a stabilizer. The stabilizer is Phe or structural analog thereof. The stabilizer is selected from the group consisting of L-phenylalanine, trans-cinnamic acid and benzoic acid. A preferred range for the stabilizers of the invention is from about 0.1 to 20 moles of stabilizer per mole active site of prokaryotic PAL. A more preferred range for the stabilizers of the invention is from about 0.5 to 10 moles of stabilizer per mole active site of prokaryotic PAL. A most preferred range for the stabilizers of the invention is from about 1 to 10 moles of stabilizer per mole active site of prokaryotic PAL.

In some embodiments, the pharmaceutical composition comprises a prokaryotic PAL variant and a pharmaceutically acceptable carrier, wherein the prokaryotic PAL variant has a greater phenylalanine-converting activity and/or a reduced immunogenicity as compared to a wild-type PAL and is effective in reducing the Phe concentration in the blood, serum or plasma of the subject to a range from below the level of detection to between about 20 μM to 60 μM, preferably to less than about 20 μM, and even more preferably to less than about 10 μM, and wherein the pharmaceutically acceptable carrier comprises a stabilizer. In some embodiments, the stabilizer is Phe or structural analog thereof. In some embodiments, the stabilizer is selected from the group consisting of L-phenylalanine, trans-cinnamic acid and benzoic acid.

In preferred embodiments, the pharmaceutical composition comprises a prokaryotic PAL variant and a pharmaceutically acceptable carrier, wherein the prokaryotic PAL variant is an *Anabaena variabilis* PAL (AvPAL) variant wherein the cysteine residues at positions 503 and 565 of the AvPAL variant have been substituted by serine residues, the AvPAL variant further comprises a water-soluble polymer of polyethylene glycol, wherein the ratio of AvPAL variant and the polyethylene glycol is about 1:3; and the AvPAL variant is effective in reducing the phenylalanine concentration in the blood, serum or plasma of the subject to a range from below the level of detection to between about 20 μM to 60 μM, preferably to less than about 20 μM, and even more preferably to less than about 10 μM, and wherein the pharmaceutically acceptable carrier comprises a stabilizer. In some embodiments, the stabilizer is Phe or structural analog thereof. In preferred embodiments, the stabilizer is selected from the group consisting of L-phenylalanine, trans-cinnamic acid and benzoic acid.

As used herein, when contemplating prokaryotic PAL variant compositions, the term "therapeutically effective amount" refers to an amount that is effective to produce the intended beneficial effect on health of a cancer patient. In some embodiments, a therapeutically effective amount of a prokaryotic PAL variant gives a decrease in blood, plasma or serum, preferably plasma, L-phenylalanine levels that provides benefit to the patient. The amount will vary from one individual to another and will depend upon a number of factors, including the overall physical condition of the patient, diet and disease state. The amount of prokaryotic PAL used for therapy gives an acceptable decrease in blood, plasma or serum, preferably plasma, L-phenylalanine levels, and maintains this value during PAL treatment at a beneficial level (typically in a range from less than about 5% to between about 35% and 100%, preferably in a range from less than about 5% to about 35%, and even more preferably in a range from less than about 5% to about 15% of the normal range of blood, plasma or serum, preferably plasma, L-phenylalanine). In some embodiments, a therapeutically effective amount of a prokaryotic PAL variant reduces tumor growth, tumor size or tumor burden by greater than about 10%, 30%, 50%, 70%, 90%, 95%, 98% or 99% in a treated patient as compared to an untreated patient. In some embodiments, a therapeutically effective amount of a prokaryotic PAL variant maintains the tumor in static condition in a treated patient as compared to an untreated patient. In some embodiments, a therapeutically effective amount of a prokaryotic PAL variant increases survival time or disease-free time at least about 10%, 20%, 50%, 100%, 2-fold, 5-fold or 10-fold longer in a treated patient as compared to an untreated patient. A therapeutically effective amount of the prokaryotic PAL variant compositions of the invention may be readily ascertained by one skilled in the art using publicly available materials and procedures.

The invention provides for administering prokaryotic PAL variants less frequently than native PAL. The dosing frequency will vary depending upon the condition being treated, but in general will be about one time per week. It is understood that the dosing frequencies actually used may vary somewhat from the frequencies disclosed herein due to variations in responses by different individuals to the prokaryotic PAL variants; the term "about" is intended to reflect such variations. It is contemplated that the prokaryotic PAL variants are administered about two times per week, about one time per week, about one time every two weeks, about one time per month, or longer than about one time per month.

The present invention may thus be used to reduce blood, plasma or serum L-phenylalanine levels. Numerous cancer-related conditions, where depletion of blood, plasma or serum L-phenylalanine levels would be beneficial, may be treated with the prokaryotic PAL variant pharmaceutical compositions of the invention.

The prokaryotic PAL pharmaceutical compositions prepared in accordance with the present invention are preferably administered by parenteral injection, either intravenously, intraperitoneally, subcutaneously, intramuscularly, intraarterially or intrathecally. However, it would be clear to one skilled in the art that other routes of delivery could also be effectively utilized using the pharmaceutical compositions of the present invention.

The methods described herein use prokaryotic PAL pharmaceutical compositions comprising the molecules described above, together with one or more pharmaceutically acceptable excipients, vehicles, diluents, stabilizers, preservatives, solubilizers, emulsifiers, adjuvants and/or carriers, and optionally other therapeutic and/or prophylactic ingredients. Such excipients include liquids such as water, saline, glycerol, polyethylene glycol, hyaluronic acid, ethanol, cyclodextrins, modified cyclodextrins (i.e., sulfobutyl ether cyclodextrins), etc. Suitable excipients for non-liquid formulations are also known to those of skill in the art.

Pharmaceutically acceptable salts can be used in the compositions of the present invention and include, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients and salts is available in Remington's Pharmaceutical Sciences, $18^{th}$ Edition (Easton, Pa.: Mack Publishing Company, 1990).

Additionally, auxiliary substances, such as wetting or emulsifying agents, biological buffering substances, surfactants, and the like, may be present in such vehicles. A biological buffer can be virtually any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions may be in the form of solid, semi-solid or liquid dosage forms, such as, for example, tablets, suppositories, pills, capsules, powders, liquids, suspensions, creams, ointments, lotions or the like, preferably in unit dosage form suitable for single administration of a precise dosage. The compositions will include a therapeutically effective amount of the prokaryotic PAL in combination with a pharmaceutically acceptable carrier and, in addition, may include other pharmaceutical agents, adjuvants, diluents, buffers, etc.

In general, the prokaryotic PAL pharmaceutical compositions of this invention will be administered as pharmaceutical formulations including those suitable for oral (including buccal and sub-lingual), rectal, nasal, topical, pulmonary, vaginal or parenteral (including intramuscular, intraarterial, intrathecal, subcutaneous and intravenous) administration or in a form suitable for administration by inhalation or insufflation. The preferred manner of administration is intravenous using a convenient daily dosage regimen, which can be adjusted according to the degree of affliction.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, etc., a prokaryotic PAL variant composition as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents, tonicifying agents, and the like, for example, sodium acetate, sorbitan monolaurate, triethanolamine sodium acetate, triethanolamine oleate, etc. Actual methods of preparing such dosage forms are known, or will be apparent, to those skilled in this art; for example, see Remington's Pharmaceutical Sciences, referenced above.

For oral administration, the composition will generally take the form of a tablet, capsule, or softgel capsule, or may be an aqueous or nonaqueous solution, suspension or syrup. Tablets and capsules are preferred oral administration forms. Tablets and capsules for oral use will generally include one or more commonly used carriers such as lactose and corn starch. Lubricating agents, such as magnesium stearate, are also typically added. When liquid suspensions are used, the active agent may be combined with emulsifying and suspending agents. If desired, flavoring, coloring and/or sweetening agents may be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid or lyophilized forms suitable for reconstitution, solubilization or suspension in liquid prior to injection, or as emulsions. Preferably, sterile injectable suspensions are formulated according to techniques known in the art using suitable carriers, dispersing or wetting agents and suspending agents. The sterile injectable formulation may also be a sterile injectable solution or a suspension in a nontoxic parenterally acceptable diluent or solvent. Among the acceptable vehicles and solvents that may be employed are water, Ringer's solution and isotonic sodium chloride solution. In addition, sterile, fixed oils, fatty esters or polyols are conventionally employed as solvents or suspending media. In addition, parenteral administration may involve the use of a slow release or sustained release system such that a constant level of dosage is maintained.

The prokaryotic PAL compositions of the invention described herein can be administered to a patient at therapeutically effective doses to treat cancer. The toxicity and therapeutic efficacy of such prokaryotic PAL compositions can be determined by standard pharmaceutical procedures in cell cultures or experimental animals, such as, for example, by determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Prokaryotic PAL compositions exhibiting large therapeutic indices are normally preferred.

The data obtained from the cell culture assays and animal studies can be used in formulating a range of dosage for use in humans. The dosage preferably lies within a range of circulating concentrations that include the $ED_{50}$ with little or minimal toxicity. The dosage can vary within this range depending upon the dosage form employed and the route of administration utilized. The therapeutically effective dose or amount can be determined from cell culture assays, and from animal models.

Dietary Protein

In addition to administering prokaryotic PAL compositions to cancer patients, it is contemplated that the dietary protein of the patients also may be restricted or modified. Those of skill in the art are aware of various commercially available protein formulas for use in the treatment of PKU. Such formulas include MAXIMAID, PHENEX 1, PHENEX 2 (Ross Laboratories, Liverpool, UK), LOFENALAC, PHENYL-FREE (Mead-Johnson), and the like.

Those of skill in the art may use the referenced protein formulas, which are generally free of Phe concentrations. The protein formulas often are supplemented with amino acids that are deficient in PKU patients. Such amino acids include, for example, L-tyrosine, and L-glutamine.

Further, as it is known that L-carnitine and taurine, which are normally found in human milk and other foodstuffs of animal origin, also should be supplied in addition to the protein restriction. In certain embodiments, the L-carnitine may be supplied as 20 mg/100 g of protein supplement, and the taurine may be supplied as 40 mg/100 g protein supplement in order to help supply amounts of these factors normally found in human milk and foods of animal origin.

In addition, those of skill in the art are referred to the 2000 National Academy of Sciences-National Research Council Dietary Reference Intakes for a further listing of other components, such as essential vitamins and minerals that should be supplied to the patient to ensure that other supplements are being provided despite the dietary protein restriction.

Referring to the discussion above regarding total protein amounts and desirable plasma Phe concentrations, one of skill in the art will be able to determine the amount of dietary protein restriction that is required and thus adjust the diet of the patient accordingly. Upon administering prokaryotic PAL to that subject, determining whether the methods of the invention are effective will entail determining the plasma Phe concentrations of the patient on a regular basis to ensure that the plasma Phe concentrations remain in a range from below the level of detection to between about 20 μM to 60 μM, preferably to less than about 20 μM, and even more preferably to less than about 10 μM. Tests for determining such concentrations are described below. Preferably, concentrations of less than the level of detection to between about 20 μM to 60 μM are achieved, more preferably to less than about 20 μM, and even more preferably to less than about 10 μM.

In certain embodiments, the invention provides a method for treating cancer comprising administering to a subject in need of such treatment a therapeutically effective amount of a pharmaceutical composition comprising a prokaryotic phenylalanine ammonia-lyase (PAL) variant and a pharmaceutically acceptable carrier, wherein the PAL variant has a greater phenylalanine-converting activity and/or a reduced immunogenicity as compared to a wild-type PAL, and is effective in reducing the phenylalanine concentration in the blood, serum or plasma of the subject to a range from below the level of detection to between about 20 μM to 60 μM, preferably to less than about 20 μM, and even more preferably to less than about 10 μM, and further comprising administering to the subject a protein-restricted (i.e., phenylalanine-free) diet.

Certain methods of the invention involve the combined use of prokaryotic PAL and dietary protein restriction to effect a therapeutic outcome in patients with various forms of cancer. To achieve the appropriate therapeutic outcome in the combination therapies contemplated herein, preferably one would generally administer to the subject the prokaryotic PAL composition and the dietary restriction in a combined amount effective to produce the desired therapeutic outcome (i.e., a lowering of plasma Phe concentration to a range from below the level of detection to optimally about 20 μM to 60 μM, preferably to less than about 20 μM, and even more preferably to less than about 10 μM, using standard detection methods well known in the art). This process may involve administering the prokaryotic PAL composition and the dietary protein therapeutic composition at the same time. This may be achieved by administering a single composition or pharmacological protein formulation that includes all of the dietary protein requirements and also includes the prokaryotic PAL within said protein formulation. Alternatively, the dietary protein (supplement or normal protein meal) is taken at about the same time as a pharmacological formulation (tablet, injection or drink) of prokaryotic PAL. Prokaryotic PAL also may be formulated into a protein bar or other foodstuff such as brownies, pancakes, cake, suitable for ingestion.

As the administration of prokaryotic PAL would not generate tyrosine (unlike administration of PAH), such treatment will still result in tyrosine being an essential amino acid for such patients. Therefore, dietary supplementation with tyrosine may be desirable for patients receiving prokaryotic PAL alone in combination with the dietary protein therapy.

In other alternatives, prokaryotic PAL treatment may precede or follow the dietary protein therapy by intervals ranging from minutes to hours. In embodiments where the protein and the prokaryotic PAL compositions are administered separately, one would generally ensure that a significant period of time did not expire between the time of each delivery, such that PAL will still be able to exert an advantageously effect on the patient. In such instances, it is contemplated that one would administer the PAL within about 2-6 hours (before or after) of the dietary protein intake, with a delay time of only about 1 hour being most preferred. In certain embodiments, it is contemplated that PAL therapy will be a continuous therapy where a daily dose of PAL is administered to the patient indefinitely.

3. Combination Therapy

Further, in addition to therapies based solely on the delivery of prokaryotic PAL and dietary protein regulation, the methods of the present invention also contemplate combination therapy with a composition that specifically targets one or more of the symptoms of cancer. Such compositions include, for example and not for limitation, cancer therapeutic agents and targeted cancer therapeutic agents.

Cancer Therapeutic Agents

In accordance with the methods described herein, any agent that exerts a therapeutic effect on cancer cells (i.e., inhibition of proliferation and/or survival) can be used as the cancer therapeutic agent in combination with the prokaryotic PAL compositions of the invention. Typically, the cancer therapeutic agent is a cytotoxic agent or a cytostatic agent.

The cancer therapeutic agent can be administered as a cancer co-therapy with the prokaryotic PAL compositions of the invention. "Cancer co-therapy" as used herein means that the cancer therapeutic agent and the prokaryotic PAL composition are administered simultaneously or sequentially, either the cancer therapeutic agent followed by the prokaryotic PAL composition, or vice versa.

Useful classes of cytotoxic agents include, for example, antitubulin agents, auristatins, DNA minor groove binders, DNA replication inhibitors, alkylating agents (e.g., platinum complexes such as cis-platin, mono(platinum), bis(platinum) and tri-nuclear platinum complexes and -carboplatin), anthracyclines, antibiotics, antifolates, antimetabolites, chemotherapy sensitizers, duocannycins, etoposides, fluorinated pyrimidines, ionophores, lexitropsins, nitrosoureas, platinols, pre-forming compounds, purine antimetabolites, puromycins, radiation sensitizers, steroids, taxanes, topoisomerase inhibitors, vinca alkaloids, and the like.

Individual cytotoxic agents include, for example, an androgen, anthramycin (AMC), asparaginase, 5-azacytidine, azathioprine, bleomycin, busulfan, buthionine sulfoximine, camptothecin, carboplatin, carmustine (BSNU), CC-1065, chlorambucil, cisplatin, colchicine, cyclophosphamide, cytarabine, cytidine arabinoside, cytochalasin B, dacarbazine, dactinomycin (formerly actinomycin), daunorubicin, decarbazine, docetaxel, doxorubicin, an estrogen, 5-fluordeoxyuridine, 5-fluorouracil, gramicidin D, hydroxyurea, idarubicin, ifosfamide, irinotecan, lomustine (CCNU), mechlorethamine, melphalan, 6-mercaptopurine, methotrexate, mithramycin, mitomycin C, mitoxantrone, nitroimidazole, paclitaxel, plicamycin, procarbizine, streptozotocin, tenoposide, 6-thioguanine, thioTEPA, topotecan, vinblastine, vincristine, vinorelbine, VP-16 and VM-26.

In some embodiments, the cancer therapeutic agent is a cytotoxic agent. Suitable cytotoxic agents include, for example, dolastatins (e.g., auristatin E, AFP, MMAF, MMAE), DNA minor groove binders (e.g., enediynes and lexitropsins), duocarnycins, taxanes (e.g., paclitaxel and docetaxel), puromycins, vinca alkaloids, CC-1065, SN-38, topotecan, morpholino-doxorubicin, rhizoxin, cyanomorpholino-doxorubicin, echinomycin, combretastatin, netropsin, epothilone A and B, estramustine, cryptophysins, cemadotin, maytansinoids, discoderrnolide, eleutherobin, and mitoxantrone.

In certain embodiments, the cytotoxic agent is a conventional chemotherapeutic such as, for example, doxorubicin, paclitaxel, melphalan, vinca alkaloids, methotrexate, mitomycin C or etoposide. In addition, potent agents such as CC-1065 analogues, calicheamicin, maytansine, analogues of dolastatin 10, rhizoxin, and palytoxin can be used.

In certain embodiments, the cytotoxic agent is a DNA minor groove binding agent, for example, a CBI compound or an enediyne (e.g., calicheamicin).

In certain embodiments, the cancer therapeutic agent is an anti-tubulin agent. Examples of anti-tubulin agents include, but are not limited to, taxanes (e.g., TAXOL (paclitaxel), TAXOTERE (docetaxel)), T67 (Tularik), vinca alkyloids (e.g., vincristine, vinblastine, vindesine, and vinorelbine), and dolastatins (e.g., auristatin E, AFP, MMAF, MMAE, AEB, AEVB). Other antitubulin agents include, for example, baccatin derivatives, taxane analogs (e.g., epothilone A and B), nocodazole, colchicine and colcimid, estramustine, cryptophysins, cemadotin, maytansinoids, combretastatins, discodermolide, and eleutherobin.

In certain embodiments, the cytotoxic agent is a maytansinoid, another group of anti-tubulin agents, for example, maytansine or DM-1.

In certain embodiments, the cancer therapeutic agent is a radioisotope. In certain other embodiments, the cancer therapeutic agent is not a radioisotope.

In certain embodiments, the cytotoxic agent is an antimetabolite. The antimetabolite can be, for example, a purine antagonist (e.g., azothioprine or mycophenolate mofetil), a dihydrofolate reductase inhibitor (e.g., methotrexate), acyclovir, gangcyclovir, zidovudine, vidarabine, ribavarin, azidothymidine, cytidine arabinoside, amantadine, dideoxyuridine, iododeoxyuridine, poscarnet, or trifluridine.

In other embodiments, the cytotoxic agent is tacrolimus, cyclosporine or rapamycin. In further embodiments, the cytoxic agent is aldesleukin, alemtuzumab, alitretinoin, allopurinol, altretamine, amifostine, anastrozole, arsenic trioxide, bexarotene, bexarotene, calusterone, capecitabine, celecoxib, cladribine, Darbepoetin alfa, Denileukin diftitox, dexrazoxane, dromostanolone propionate, epirubicin, Epoetin alfa, estramustine, exemestane, Filgrastim, floxuridine, fludarabine, fulvestrant, gemcitabine, gemtuzumab ozogamicin, goserelin, idarubicin, ifosfamide, imatinib mesylate, Interferon alfa-2a, irinotecan, letrozole, leucovorin, levamisole, meclorethamine or nitrogen mustard, megestrol, mesna, methotrexate, methoxsalen, mitomycin C, mitotane, nandrolone phenpropionate, oprelvekin, oxaliplatin, pamidronate, pegademase, pegaspargase, pegfilgrastim, pentostatin, pipobroman, plicamycin, porfimer sodium, procarbazine, quinacrine, rasburicase, Rituximab, Sargramostim, streptozocin, tamoxifen, temozolomide, teniposide, testolactone, thioguanine, toremifene, Tositumomab, Trastuzumab, tretinoin, uracil mustard, valrubicin, vinblastine, vincristine, vinorelbine and zoledronate.

In certain embodiments, the invention provides a method for treating cancer comprising administering to a subject in need of such treatment a therapeutically effective amount of a pharmaceutical composition comprising a prokaryotic phenylalanine ammonia-lyase (PAL) variant and a pharmaceutically acceptable carrier, wherein the PAL variant has a greater phenylalanine-converting activity and/or a reduced immunogenicity as compared to a wild-type PAL, and is effective in reducing the Phe concentration in the blood, serum or plasma of the subject to a range from below the level of detection to between about 20 μM to 60 μM, preferably to less than about 20 μM, and even more preferably to less than about 10 μM, and further comprising administering a therapeutically effective amount of a pharmaceutical composition comprising a cancer therapeutic agent.

Targeted Cancer Therapeutic Agents

In accordance with the methods described herein, any agent that exerts a therapeutic effect on specific cancer cells (i.e., inhibition of proliferation and/or survival) can be used as the targeted cancer therapeutic agent in combination with the prokaryotic PAL compositions of the invention. Typically, the targeted cancer therapeutic agent is an antibody or an enzyme or protein that binds selectively to particular type of tumor cells or tissues, for example and not for limitation, by virtue of having an antibody-like targeting domain or via receptor-mediated binding. The antibody, polypeptide having an antibody-like targeting domain, enzyme or protein can be radiolabeled, or can be conjugated to a toxin or other agent that is able to exert a cytotoxic or cytostatic effect on the targeted cells or tissues. Alternatively, the targeted cancer therapeutic agent can be an agent that exerts a therapeutic effect on specific cancer cells or tissues (i.e., inhibition of proliferation and/or survival) by virtue of inhibiting or activating a protein, for example and not for limitation, an enzyme or a receptor, which is preferentially expressed or active in that particular type of tumor cell or tissue.

The targeted cancer therapeutic agent can be administered as a targeted cancer co-therapy with the prokaryotic PAL compositions of the invention. "Targeted cancer co-therapy" means that the targeted cancer therapeutic agent and the prokaryotic PAL composition are administered simultaneously or sequentially, either the targeted cancer therapeutic agent followed by the prokaryotic PAL composition, or vice versa.

In certain embodiments, the targeted cancer therapeutic agent is a humanized anti HER2 monoclonal antibody, RITUXAN (rituximab; Genentech; a chimeric anti CD20 monoclonal antibody); OVAREX (AltaRex Corporation, MA); PANOREX (Glaxo Wellcome, NC; a murine IgG2a antibody); Cetuximab Erbitux (Imclone Systems Inc., NY; an anti-EGFR IgG chimeric antibody); Vitaxin (MedImmune, Inc., MD; Campath I/H (Leukosite, MA; a humanized IgG1 antibody); Smart MI95 (Protein Design Labs, Inc., CA; a humanized anti-CD33 IgG antibody); LymphoCide (Immunomedics, Inc., NJ; a humanized anti-CD22 IgG antibody); Smart ID10 (Protein Design Labs, Inc., CA; a humanized anti-HLA-DR antibody); Oncolym (Techniclone, Inc., CA; a radiolabeled murine anti-HLA-Dr10 antibody); Allomune (BioTransplant, CA; a humanized anti-CD2 mAb); Avastin (Genentech, Inc., CA; an anti-VEGF humanized antibody); Epratuzamab (Immunomedics, Inc., NJ and Amgen, CA; an anti-CD22 antibody); and CEAcide (Immunomedics, NJ; a humanized anti-CEA antibody).

Other suitable antibodies include, but are not limited to, antibodies against the following antigens: CA 125, CA 15-3, CA19-9, L6, Lewis Y, Lewis X, alpha fetoprotein, CA 242, placental alkaline phosphatase, prostate specific antigen, prostatic acid phosphatase, epidermal growth factor, MAGE-1, MAGE-2, MAGE-3, MAGE-4, anti transferrin receptor, p97, MUC1-KLH, CEA, gp100, MART1, Prostate Specific Antigen, IL-2 receptor, CD20, CD52, CD33, CD22, human chorionic gonadotropin, CD38, CD40, mucin, P21, MPG, and Neu oncogene product.

In certain embodiments, the targeted cancer therapeutic agent is an enzyme or other protein having an antibody-like targeting domain or having the ability to selectively bind to particular cells or tissues (e.g., by ligand-receptor binding). Typically, protein having an antibody-like targeting domain, enzyme or other protein is conjugated to a cancer therapeutic agent, for example, a compound or peptide/polypeptide, such as a toxin e.g., ricin, Diptheria toxin, Pseudomonas endotoxin, and the like (Kreitman, AAPS J. 8(3):E532-E551 (2006)) or other agent that is able to exert a cytotoxic or cytostatic effect on the targeted cells or tissues.

In certain embodiments, the targeted cancer therapeutic agent is compound (e.g., small molecule or peptide/polypeptide) that exerts a therapeutic effect on specific cancer cells or tissues, e.g., a serine/threonine kinase inhibitor, a tyrosine kinase inhibitor, a nuclear receptor agonist, a nuclear receptor antagonist, and the like.

In certain embodiments, the invention provides a method for treating cancer comprising administering to a subject in need of such treatment a therapeutically effective amount of a pharmaceutical composition comprising a prokaryotic phenylalanine ammonia-lyase (PAL) variant and a pharmaceutically acceptable carrier, wherein the PAL variant has a greater phenylalanine-converting activity and/or a reduced immunogenicity as compared to a wild-type PAL, and is effective in reducing the Phe concentration in the blood, serum or plasma of the subject to a range from below the level of detection to between about 20 μM to 60 μM, preferably to less than about 20 μM, and even more preferably to less than about 10 μM, and further comprising administering a therapeutically effective amount of a pharmaceutical composition comprising a targeted cancer therapeutic agent.

4. Identifying and Monitoring Patient Populations

As discussed herein throughout, it will be necessary in various embodiments of the present invention to determine whether a given cancer patient may be responsive to prokaryotic PAL therapy, and to determine the phenylalanine (Phe) concentrations of the patient both initially and during an ongoing therapeutic regimen to monitor the efficacy of the regimen in terms of reduction in plasma Phe concentration. Exemplary such methods are described herein below.

Identifying Patients Responsive to Prokaryotic PAL Therapy

The identification of patients for which treatment with the prokaryotic PAL compositions of the present invention may be useful can be made on the basis of in vitro culture experiments or in vivo human tumor xenograft studies in mice, or by comparison with tumor types with known or demonstrated dependence on Phe for its growth and its sensitivity to Phe restriction or depletion in animal models of human cancer.

In vitro culture experiments, in which tumor cells (e.g., from a tumor biopsy or clinical aspirate) are grown in the absence or presence of a prokaryotic PAL composition or in the absence or presence of a phenylalanine-deficient medium, can be performed using protocols known in the art (see, for example, Abell, et al., Cancer Res. 32:285-290 (1972); Stith, et al., Cancer Res. 33:966-971 (1973); Fu, et al., Cancer Res. 59:758-765 (1999); Fu, et al., J. Cell. Physiol. 209:522-534 (2006); Elstad, et al., Nutr. Cancer 25:47-60 (1996); Nunez, et al., Cancer Lett. 236:133-141 (2006)). See also EXAMPLE 14.

In vivo human tumor xenograft studies in mice, in which tumor cells (e.g., from a tumor biopsy or clinical aspirate) are injected into nude or SCID mice, and then transplanted into naïve nude or SCID mice in the absence or presence of a prokaryotic PAL composition or in the absence or presence of a phenylalanine-deficient diet, can be performed using protocols known in the art (see, for example, Abell, et al., Cancer Res. 33:2529-2532 (1973); Shen, et al., Cancer Res. 37:1051-105 (1977); Fu, et al., Nutr. Cancer 31:1-7 (1998); Fu, et al., Nutr. Cancer 45:60-73 (2003); Meadows, et al., Cancer Res. 42:3056-3063, 1982; Elstad, et al., Anticancer Res. 13:523-528, (1993)). See also EXAMPLE 15.

Tumor types with known or demonstrated dependence on Phe for its growth and its sensitivity to Phe restriction or depletion in animal models of human cancer include, for example, leukemia, metastatic myeloma, and androgen-independent prostate cancer (Abell, et al., (1973), ibid.; Shen, et al., (1977), ibid.; Fu, et al., (1998), ibid.; Fu, et al., (2003), ibid.; Meadows, et al., (1982), ibid.; Elstad, et al., (1993), ibid.).

EXAMPLE 14 shows that the proliferation and/or survival of tumor cells derived from lung cancer, brain or central nervous system cancer, colon cancer, prostate cancer, renal cancer, metastatic melanoma, head and neck cancer, uterine cancer, leukemia (e.g., acute myeloid leukemia or acute lymphoblastoid leukemia) and myeloma is sensitive to Phe restriction upon incubation with a prokaryotic PAL composition of the present invention.

Determination of Phenylalanine Concentrations

Methods for determining the concentration of phenylalanine (Phe) in blood, serum or plasma are known in the art, some of which are described in prior co-pending U.S. patent application Ser. No. 11/230,374 filed on Sep. 19, 2005, which is herein incorporated by reference in its entirety. It is contemplated that the plasma Phe levels of the patients will be monitored at convenient intervals (e.g., daily, every other day or weekly) throughout the time course of the therapeutic regimen. By monitoring the plasma Phe levels with such regularity, the clinician will be able to assess the efficacy of the treatment and adjust the prokaryotic PAL and/or dietary protein requirements accordingly.

E. Production Of Prokaryotic PAL

Another aspect of the invention is a method of producing prokaryotic PAL or biologically active fragment, mutant variant or analog thereof. In a preferred embodiment, recombinant prokaryotic PAL or a biologically active fragment, mutant, variant or analog thereof is over-expressed, with or without an N-terminal tag (e.g., octahistidyl-tag), in a vector, preferably pIBX1 (Su, et al., Appl. Environ. Microbiol. 62:2723-2734 (1996)) or pET28a (Invitrogen) with an inducible promoter such as with IPTG (isopropyl-beta-D-thiogalactopyranoside), in *E. coli* BLR(DE3)/pLysS (Novagen) or *E. coli* BL21 (DE3)/pLysS (anvitrogen) cells. Seed culture for a bioreactor/fermenter is grown from a glycerol stock in shake flasks. Such seed culture is then used to spike into a controlled bioreactor in fed-batch mode. Glucose is supplemented and pH is controlled with base ($NH_4OH$) and agitation is up to 1200 rpm. $O_2$ feed keeps dissolved oxygen to greater than 20%. The cells are grown at a temperature of 37° C. until reaching an $OD_{600}$ of 70-100 (~22-25 hrs) and then induced with 0.4 mM IPTG. The temperature is reduced to 30° C. and grown until activity change is <0.1 IU/mL (approximately 40-48 hrs and an $OD_{600}$ typically of 200). Cell culture media is typically defined and composed of yeast extract protein, peptone-tryptone, glucose, glycerol, casamino acids, trace salts and phosphate buffering salts. The recombinant prokaryotic PAL product or biologically active fragment, mutant, variant or analog thereof is produced intracellularly and not secreted. The bacteria are harvested by continuous centrifugation (Alfa-Laval, Carr, Ceba, or equivalent).

F. Purification Of Prokaryotic PAL

A further aspect of the present invention features a method to purify prokaryotic PAL or a biologically active fragment, mutant, variant or analog thereof. According to a first embodiment, a transformed cell mass is grown and ruptured leaving crude recombinant enzyme. Exogenous materials are normally separated from the crude bulk to prevent fouling of the columns. Chromatographic purification is conducted using one or several chromatographic resins. Subsequently, the purified protein is formulated into a buffer designed to provide stable activity over an extended period of time. In another preferred embodiment, the method to purify the prokaryotic PAL or biologically active fragment, mutant, variant or analog thereof comprises: (a) lysis of the bacteria containing recombinant prokaryotic PAL or biologically active fragment, mutant, variant or analog thereof using a pressure homogenizer (but potentially by other physical means such as glass bead lysis); (b) heat treatment; (c) clarification of this lysate using a second continuous centrifugation step and/or depth filtration (as with Cuono Zeta Plus or Maximizer, Pall Filtron, or Millipore Millistak or Opticao filters); (d) passage through a charcoal filtration step (as with Millipore Millistak 40AC); (e) passage through a final filtration step (as with a Sartorious Sartopore 0.2 μm filter); (f) passage over a butyl hydrophobic interaction chromatography (as in Toyopearl Butyl 650M from Tosoh Biosciences); (g) passage over a Q ion exchange column (as in a Macroprep High Q from BioRad); and (b) recovery of final product by buffer exchange with tangential flow filtration (as with a Sartorious Hydrosart or PES 100 kDa membrane). Those skilled in the art readily appreciate that one or more of the chromatography steps may be omitted or substituted, or that the order of the chromatography steps may be changed within the scope of the present invention. Finally, appropriate sterilizing steps may be performed as desired.

Having now generally described the invention, the same may be more readily understood through the following reference to the following examples. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

EXAMPLES

Example 1

Cloning of *Nostoc punctiforme* and *Anabaena variabilis* PAL

DNA Manipulations

*N. punctiforme* genomic DNA was purchased from ATCC (29133D) and the PAL gene (ZP_00105927) was PCR-amplified from primers 5'-CACTGTCATATGAATATAACATCTCTACAACAGAACAT-3' (SEQ ID NO:12) and 5'-GACAGTGGCGGCCGCTCACGTTGACTTTAAGCTCGAAAAAATATG-3' (SEQ ID NO:13). The resulting PCR product was digested with NdeI and NotI and the 1.7 kb fragment was ligated into pET-28a(+) and pET-30a (+) (Novagen) for N-His tagged and untagged, respectively.

*A. variabilis* cells were purchased from ATCC (29413). Genomic DNA was extracted (Qiagen) and the PAL gene (YP_324488) was amplified by SOE-PCR to remove an NheI site. Primer 1 (5'-CACTGTGCTAGCATGAAGACACTATCTCAAGCACAAAG-3') (SEQ ID NO:14) and primer 2 (5'-GGAAATTTCCTCCATGATAGCTGGCTTGGTTATCAACATCAATTAGTGG-3') (SEQ ID NO:15) were used to amplify nucleotides 1-1190 and primer 3 (5'-CCACTAATTGATGTTGATAACCAAGCCAGCTATCATGGAGGAAATTTCC-3') (SEQ ID NO:16) and primer 4 (5'-CACTGTGCGGCCGCTTAATGCAAGCAGGGTAAGATATCTTG-3') (SEQ ID NO:17) were used to amplify nucleotides 1142-1771. These two PCR products were combined to amplify the full-length gene with primers 1 and 4. The resulting PCR product was digested with NheI, blunted with Klenow (NEB), then digested with NotI. The 1.7 kb fragment was ligated into pET-28a(+) and pET-30a(+) (Novagen). This plasmid was named 3p86-23.

The *A. variabilis* PAL (AvPAL) gene was also cloned into the vector pIBX7 (Tkalec, et al., Appl. Environ. Microbiol. 66:29-35 (2000)), which was derived from pIBX1 (Su, et al., Appl. Environ. Microbiol. 62:2723-2734 (1996)) (see EXAMPLE 7).

Bacterial Strains and Culture Conditions

For *N. punctiforme* PAL (NpPAL), *E. coli* BL21(DE3) cells (Stratagene) were transformed with pGro7 (TaKaRa) and competent BL21 (DE3)pGro7 cells were prepared by the Inoue Method (Sambrook and Russell, Molecular Cloning: A Laboratory Manual, 3rd Edition (Cold Spring Harbor Laboratory Press, Cold Spring Harbor, 2001)). These cells were transformed with pET-28-NpPAL and cultured in 25 mL LB with 50 mg/L kanamycin and 20 mg/L chloramphenicol overnight at 37° C. Twenty milliliters of this culture was seeded into 1 L of LB medium with kanamycin, chloramphenicol, and 500 mg/L L-arabinose and grown at 37° C. At an $OD_{600}$ of 0.6, the culture was chilled on ice. After 5 minutes, the culture was induced with 0.3 mM IPTG and grown for 16 hours at 20° C. Cells were harvested by centrifugation.

BL21(DE3)pLysS cells (Stratagene) were transformed with AvPAL and cultured identically to NpPAL without the arabinose induction.

AvPAL cloned in the pIBX7 vector (see EXAMPLE 7) was introduced by transformation into BLR(DE3)/pLysS (Novagen) cells and cultured in 25 mL LB with 50 mg/L kanamycin overnight at 37° C. Twenty milliliters of this culture was seeded into 1 L of LB medium with kanamycin, and grown at 37° C. At an $OD_{600}$ of 0.6, the culture was chilled on ice. After 5 minutes, the culture was induced with 0.3 mM IPTG and grown for 16 hours at 30° C. Cells were harvested by centrifugation.

Example 2

Purification of NpPAL and AvPAL

The cultures were centrifuged in a bench-top centrifuge at 5,000 g for 20 minutes and the supernatant discarded. The cell pellets were typically frozen at −70° C. prior to further processing. Upon thawing, the cell pellets were suspended to approximately 80 optical density units (600 nm) in TBS (25 mM Tris, 150 mM NaCl, pH 7.8). The cells were lysed by two passes through an APV pressure homogenizer at 12-14,000 psi. The crude lysate was then heat-treated at 55° C. for 2 hours. The lysate is centrifuged at 10,000 g for 30 minutes and the supernatant retained and filtered with a 0.2 μm vacuum filter (Corning).

The PAL was purified from the clarified lysate by passage sequentially over a butyl 650M column (Tosoh BioSciences) and a MacroPrep High Q column (BioRad). The eluted product showed a high level of purity by both SDS PAGE and reverse phase HPLC.

Example 3

Generation of Pegylated PAL Variants

A method for pegylation of PAL from *Rhodosporidium toruloides* (RtPAL) is described below. Similar methods are used for pegylation of prokaryotic PAL (e.g., *Nostoc punctiforme* (NpPAL) or *Anabaena variabilis* (AvPAL)) are described in EXAMPLE 6.

Protein Pegylation

Pegylation uses modifications of literature methods (Hershfield, et al., (1991), ibid.; U.S. Pat. No. 6,057,292; Lu, et al., Biochemistry 40(44):13288-13301 (2001); Nektar Therapeutics, 2003 catalog). Activated PEGs include both the linear PEG succinimidyl succinates (mPEG-SPA, MW 5 kDa or MW 20 kDa) and the branched PEG hydrosuccinimides ($mPEG_2$-NHS ester, MW 10 kDa or MW 40 kDa), which are both capped on one end with a methoxy group and available from Nektar Therapeutics; experimental determination of optimal pegylated proteins is normally required (Veronese, et al., J. Bioactive Compatible Polymers 12:196-207 (1997)). Optimal pegylation conditions are determined using different ratios of PAL:PEG (taking into account the molar ratio of protein along with the number of lysines per protein monomer), different pHs, different buffers, various temperatures and incubation times. High PAL protein:PEG derivatization ratios are necessary since native PAL has a large number of lysines (29 per *Rhodosporidium toruloides* (Rt) monomer) and because un-modified PAL displays immunoreactivity upon repeated injection in mice and since naked (wild-type) PAL is quickly inactivated upon exposure to proteases. Pegylation reactions are stopped by freezing at −20° C., and the samples will be analyzed by SDS-PAGE, MALDI-TOF mass spectroscopy, activity assessment, proteolytic sensitivity, and immunoreactivity.

Prior to activity, proteolysis, and immune assessment, and in order to remove excess unreacted PEG, reactions are dialyzed against pH 8.5, 0.05 M potassium phosphate buffer overnight at 4° C. with stirring using Tube-O-Dialyzers (GenoTechnology). After protein concentration is determined using the NI protein assay kit (GenoTechnology), PAL activity measurements will be performed on underivatized and PEG derivatized PAL samples using standard reaction conditions, as previously described. Following in vitro characterization, in vivo trials will be conducted with the most promising pegylated therapeutic candidates using the PKU mouse model.

Characterization

Protein concentration is determined using the PAL extinction coefficient (0.5 and 0.75 mg mL$^{-1}$ cm$^{-1}$ for RtPAL and AvPAL, respectively) at 280 nm for non-modified protein samples and for pegylated protein samples the concentration is calculated using the NI Protein Assay (GenoTechnology) that includes sample processing to remove non-protein contaminants that might interfere with accurate protein concentration determination.

PEG-PAL products are characterized by peptide mapping techniques to determine site-specific pegylation (LC/ESI-MSD), and trinitrobenzene sulfonate (TNBS) to determine the free amine titration before and after pegylation. Peptide mapping determines the relative occupancy of pegylation at a majority of the tryptic peptides that terminate with lysine, however, due to size and multiple adjacent lysine tryptic peptides, not all sites are visible using this technique. The TNBS assay more accurately defines the average number of PEG molecules per mol of enzyme, but gives no information about which sites get pegylated. For this reason, both assays are used and are complementary to each other. Rough estimates of percent derivatization of PAL products by PEG can be determined by SDS-PAGE and native gel analyses. Enzymatic assays are used to assess specific activity before and after pegylation and to provide evidence that there is no loss of the tetrameric PAL structure.

PAL Activity Assay

The PAL activity assay is conducted using a Cary UV spectrophotometer (Cary 50) in the kinetics mode. The activity of PAL with L-phenylalanine substrate is assayed at room temperature (25° C.) by measuring the production of trans-cinnamate monitored by the absorbance increase at 290 nm (Hodgins, (1968), ibid.). The molar extinction coefficient of trans-cinnamic acid at 290 nm is 10,238 liter M$^{-1}$ cm$^{-1}$. Reaction mixtures contain 22.5 mM phenylalanine in 100 mM Tris-HCl buffer, pH 8.5. For standard measurements the final enzyme concentration is 0.0035 mg/mL, but for kinetic studies the enzyme concentration in the assay is adjusted so that the slope at 290 nm per min is in the range of 0.005 to 0.02. Activity data is expressed as specific activity (µmol× min$^{-1}$ mg$^{-1}$). One unit of PAL is defined as that amount of enzyme that produces 1 µmol of trans-cinnamic acid per minute at room temperature.

Example 4

Test of In Vitro Half-Life and Immunogenicity

After biochemical characterization, the most promising PEG-PAL candidates are screened for immunoreactivity against antibodies raised by PKU mice injected with native PAL (non-pegylated) using three different and complementary techniques (Western blot, ELISA, and immunoprecipitation (IP)).

For Western blot analysis, PAL anti-serum (from mice injected with native PAL) is used in a dilution 1:10,000. As a negative control the serum from buffer treated-mice is also used in the same dilution. The secondary antibody, alkaline phosphatase-conjugated goat anti-mouse IgG (Promega), is diluted to 1:5,000 and color is developed using the AP substrate Western Blue (Promega). The ELISA test is performed using Nunc/Immuno Maxisorp plates (Nalge Nunc International) following standard procedures using 1 mg/mL of PAL in PBS and blocking with PBS, 0.05% Tween-20, 2% BSA. The mouse antisera (from native PAL exposed mice) is diluted 1:10,000 in EB block solution (PBS, 0.05% Tween-20, 2% BSA), and a HRP-goat anti-mouse IgG is used as secondary antibody with TMB used for detection at 450 nm.

Immunoprecipitation is used to test for PAL antibody binding. Protein samples (PAL or pegylated PAL) are incubated in TIBS buffer (Tris buffered saline with 0.1% Tween) and PAL activity is measured before adding the antibody sample. Each sample is incubated with 8-fold excess of positive control anti-PAL serum and a duplicate negative control reaction using non-immune mouse serum. After incubation, protein G Sepharose 4 (50%, v/v) is added in excess, taking into account the mouse IgG binding capacity of the beads, and the samples are incubated again at 4° C. overnight with rotation. Supernatants are recovered by centrifugation and the PAL activity of each sample is assayed on the supernatants. The bead pellets are not discarded, so that further analysis by Western blot can be performed. To confirm that antibody-bead binding has occurred, Western blot is used to detect the PAL antigen on the beads. Beads that have been recovered by centrifugation after the PAL binding step are washed several times with TTBS and TBS buffers. Following these rinses, SDS-PAGE loading buffer is added to the beads and the samples are heated at 95° C. for 5 minutes. Samples are then analyzed by Western blot using PAL anti-serum. Enzyme variants showing poor antibody binding have corresponding little PAL in the pelleted bead fractions as detected by Western blot and show higher activities remaining in the supernatant as compared to native un-modified PAL which displays high antibody binding.

Example 5

Test of Protease Sensitivity

Protease mapping studies on native PAL from *R. toruloides* have indicated primary sites of proteolytic sensitivity. Removal of such sites may reduce or eliminate proteolytic sensitivity and contribute to the development of an effective PKU enzyme substitute. However, elimination of such sites for proteolytic sensitivity may result in the reduction or loss of enzyme activity.

After protein engineering has created improved PAL (and PEG-PAL) mutants that retain activity, screening for protease resistance using incubation with a trypsin/chymotrypsin protease cocktail, followed by monitoring for retention of activity (via $OD_{290}$ measurement) and reduced protein cleavage (via PAGE gel analysis) allows for the identification of mutants with appropriate in vitro properties to be used for in vivo testing.

Proteolytic stability will be assessed using incubation with a protease cocktail that approximates the intestinal environment and contains 2.3 mM trypsin, 3.5 mM chymotrypsin, 3.05 mM carboxypeptidase A, and 3.65 mM carboxypeptidase B. Proteolysis testing will involve enzymatic incubations, adding proteases to the PAL solutions, to determine the degree of protease sensitivity for the different protein variants being examined (native or mutant protein with or without pegylation or other chemical modification), including time courses of activity retention and stability retention after protease exposure. SDS-PAGE and MALDI-TOF mass spectrometric mapping experiments will be used to determine the location of any protease sensitive sites (Kriwacki, R. W., et al., J. Biomol. Tech. 9(3):5-15 (1980)). These mapping results will be important to determine primary sites of protease susceptibility (such as the two primary sites already identified), so that all major sensitivity sites can be removed using pegylation protection and/or mutation to remove and/or protect susceptible regions from the PAL architecture.

Example 6

Generation of PEGylated NpPAL and AvPAL

In general, PEGylation for both NpPAL and AvPAL involves mixing the protein with SUNBRIGHT ME-200HS 20 kDa NHS-activated PEG (NOF).

Protocol for PEGylation, standard "HC" method using NHS-activated 20 kDa linear PEG:

1) The protein was evaluated for the presence of endotoxin. A protein solution (0.1 mL) was diluted in 0.9 mL fresh MQ water and tested with a hand-held Charles River apparatus (EndoPTS) for endotoxin at the 0.5 EU/mL sensitivity level. If endotoxin was greater than 0.5 EU/mL, then endotoxin was reduced initially by Mustang E filtration, followed by Sterogene Etox resin, and less preferably by further chromatographic purification. Reduction was limited but sufficiently useful by passage over DEAE FF (Amersham) at pH 7.8.

2) Concentration and buffer exchange of protein. The protein was concentrated to greater than 25 mg/mL but less than or equal to 75 mg/mL and buffer exchanged to 50 mM $KPO_4$, pH 8.5. If a spin filter was used to prepare this concentration, the filter was first tested for endotoxin by spinning at reduced speed and time (3000 rpm, 3 minutes) with buffer alone, then testing the retained buffer for endotoxin in the same way as the protein in step 1. The buffer batch record/recipe for 50 mM KPO4, pH 8.5 consisted of water (QS to 1 L), potassium phosphate dibasic (8.4913 g/L of 48.75 mM), and potassium phosphate monobasic (0.17011 g/L of 1.25 mM). The solution was filtered through a 0.2 μm filter and stored at room temperature. The concentrated product was slowly filtered (1-2 mL/min) through a Mustang E filter acrodisc. A sample diluted and blanked with sterile TBS, pH 7.5 was measured at A280 to determine protein concentration. The extinction coefficient was 0.83 for NpPAL and 0.75 for AvPAL.

3) PEGylation of NpPAL and AvPAL. PEG normally stored at −80° C. was warmed to room temperature. KPO4 buffer was added to PEG to resuspend by vortexing at maximum speed, and shaking tube hard in hand to ensure all large chunks were suspended. The protein was added to the well-suspended PEG solution within one minute of having first wetted the PEG and mixed by very gentle inversion. Tubes wrapped in aluminum foil were placed on the axis of a rocker and rocked very gently at room temperature for 3 hours. The tubes were filled with TBS (pH 7.5) and sterile filtered. The suspensions were either formulated immediately or stored at 4° C. until ready for formulation.

4) Formulation. The formulation buffer recipe/batch record consisted of water (QS to 1 L), Tris-Base (3.2 mM), Tris-HCl (16.8 mM), and sodium chloride; the buffer solution was filtered through a 0.2 μm filter and stored at room temperature. The buffer solution was subjected to tangential flow filtration using a Vivaflow 50 (smaller lots) or Vivaflow 200 (larger lots) with a 100 MWCO regenerated cellulose membrane. The solution was flushed with MQ water, 0.1 N NaOH, and 200 mL water again. The solution was equilibrated with TBS, pH 7.5 at 50 mL/min cross-flow. The pH of the permeate was determined to ensure a pH of 7.5.

The solution was buffer exchanged by first diluting with TBS approximately 3-fold and returning to original volume at least four times. Cross-flow was typically 180-200 mL/min for both Vivaflow 50 and 200.

The final product was filtered through Mustang E. The presence of endotoxin was evaluated after diluting 0.1 mL with 1.9 mL sterile fresh water. If endotoxin was greater than 1 EU/mL, reduction was conducted with Sterogene Etox gel. Formulated, sterile PEGylated NpPAL or AvPAL were sealed in vials and placed at −70° C. until ready for in vivo studies.

Example 7

Generation of AvPAL Variants (Cysteine Mutants)

Amino acid substitutions were made in the AvPAL polypeptide to reduce aggregation that occurs in bacterially expressed, recombinant proteins. Protein aggregation may reduce enzyme activity and/or increase immunogenicity in vivo. One such form of aggregation occurs as a result of formation of inter-chain disulfide bonds. To minimize this possibility, various AvPAL cysteine residues, alone or in combination, were replaced with serine residues.

The AvPAL polypeptide has 6 cysteine residues, at positions 64, 235, 318, 424, 503 and 565 (SEQ ID NO:4). The following AvPAL single cysteine mutants were generated: AvPAL_C64S (SEQ ID NO:7), AvPAL_C318S (SEQ ID NO:8), AvPAL_C503S (SEQ ID NO:9), and AvPAL_C565S (SEQ ID NO:10). An AvPAL double cysteine mutant, AvPAL_S565SC503S (SEQ ID NO:11), was also generated. FIG. 5A-5E shows the amino acid sequences of these AvPAL cysteine mutants.

Cloning

The AvPAL gene was amplified from *Anabaena variabilis* genomic DNA (ATCC 29413-U, Qiagen DNeasy Kit) with forward primer AvarPALfor (5'-CACTGTCATATGAAGACACTATCTCAAGCACAAAG-3') (SEQ ID NO:18) and reverse primer AvarPALrev (5'-CACTGTCTCGAGATGCAAGCAGGGTAAGATATCTTG-3') (SEQ ID NO:19). The resulting PCR product was treated with Taq and then ligated into pCR2.1 TOPO TA (Invitrogen). The resulting plasmid was named 1p40.

A 5' NheI site was added and an internal NheI site was removed by SOE-PCR. The upstream AvPAL fragment was amplified from 1p40 with forward primer N-Nhe-AvPAL (5'-CACTGTGCTAGCATGAAGACACTATCTCAAGCACAAAG-3') (SEQ ID NO:20) and reverse primer Nhe-AvPALrev (5'-GGAAATTTCCTCCATGATAGCTG-GCTTGGTTATCAACATCAATTAGTGG-3') (SEQ ID NO:21), and the downstream AvPAL fragment was amplified from 11p40 with forward primer Nhe-AvPALfor (5'-CCAC-TAATTGATGTTGATAACCAAGCCAGC-TATCATGGAGGAAATTTCC-3') (SEQ ID NO:22) and reverse primer AvPALrev-r (5'-ACAGTGGCGGCCGCT-TAATGCAAGCAGGGTAAGATATCTTG-3') (SEQ ID NO:23). In a single PCR reaction, the two PCR products were annealed and extended with DNA polymerase to produce the full-length AvPAL gene, and then amplified with primers N-Nhe-AvPAL and AvPALrev-r. The resulting PCR product was digested with NheI, blunted with Klenow, digested with NotI, and ligated into the pET28a+ vector (prepared by digestion with NdeI, blunting with Klenow, and digestion with NotI). The resulting plasmid was named 3p86-23.

New restriction sites were added by PCR. AvPAL was amplified from plasmid 3p86-23 with forward primer AvEcoRIfor (5'-CACTGTGAATTCATGAAGACAC-TATCTCAAGCACAAAG-3') (SEQ ID NO:24) and reverse primer AvSmaIrev (5'-CACTGTCCCGGGTTAATGCAAG-CAGGGTAAGATATCT-3') (SEQ ID NO:25). The resulting PCR product was digested with EcoRI and SmaI and ligated into EcoRI- and SmaI-digested pIBX7 vector. The resulting plasmid was named 7p56 Av3.

Cysteine Mutants

Two cysteine codons in the AvPAL gene, corresponding to positions 503 and 565 of the AvPAL polypeptide, were substituted with serine codons by site-directed mutagenesis (QuickChange XL II, Stratagene). The cysteine codon at position 503 was changed to a serine codon in plasmid 7p56 Av3 by PCR with forward primer Av_C503S (5'-GTCAT-TACGATGCACGCGCC TCTCTATCACCTGCAACTGAG-3') (SEQ ID NO:26) and reverse primer Av_C503Srev (5'-CTCAGTTGCAGGT-GATAGAGAGGCGCGTGCATCGTAATGAC-3') (SEQ ID NO:27). The serine codon is underlined and the G to C mutation in the coding strand (C to G mutation in the non-coding strand) is indicated in bold. The resulting plasmid was named j282. The cysteine codon at position 565 was changed to a serine codon in plasmid j282 with forward primer Av_C565S (5'-CAGTTCAAGATATCTTACCC TCCTTGCATTAACCCGGGCTGC-3') (SEQ ID NO:28) and reverse primer Av_C565Srev (5'-GCAGCCCGGGT-TAATGCAAGGAGGGTAAGATATCTTGAACTG-3') (SEQ ID NO:29). The serine codon is underlined and the G to C mutation in the coding strand (C to G mutation in the non-coding strand) is indicated in bold. The resulting plasmid was named j298a.

Cysteine codons in the AvPAL gene at positions 64, 318 and 565 of the AvPAL polypeptide were similarly substituted with serine codons using the following primer pairs: C64S, forward primer Av_C64S (5'-GCAGGGTATTCAGGCATCT TCTGATTACATTAATAATGCTGTTG-3') (SEQ ID NO:30) and reverse primer Av_C64Srev (5'-CAACAGCAT-TATTAATGTAATC AGAAGATGCCTGAATACCCTGC-3') (SEQ ID NO:31); C318S, forward primer Av_C318S (5'-CAAGATCGTTACT-CACTCCGATCCCTTCCCCAGTATTTGGGGC-3') (SEQ ID NO:32) and reverse primer Av_C318Srev (5'-GC-CCCAAATACTGGGGAAG GGATCGGAGTGAGTAACGATCTTG-3') (SEQ ID NO:33); and C565S, forward primer Av_C565S (SEQ ID NO:28) and reverse primer Av_C565Srev (SEQ ID NO:29). The serine codons are underlined, and the G to C mutations in the coding strands and the C to G mutations in the non-coding strands are indicated in bold.

Example 8

In Vitro Enzyme Activity of AvPAL Variants (Cysteine Mutants)

The purpose of this study was to determine the effect of serine substitution of the various cysteine residues in the AvPAL polypeptide on in vitro phenylalanine ammonia-lyase (PAL) enzyme activity.

AvPAL variants (i.e., cysteine mutants) were cloned as described in EXAMPLE 7. The AvPAL cysteine mutant expression plasmids were transformed into bacteria and the AvPAL cysteine mutant polypeptides were expressed as described in EXAMPLE 1 and purified as described in EXAMPLE 2.

The wild-type (WT) AvPAL and AvPAL cysteine mutants were tested for in vitro PAL enzyme activity as described in EXAMPLE 3. Table 1 shows that compared to unpegylated WT AvPAL, the in vitro PAL specific activity of the purified, unpegylated AvPAL cysteine mutant proteins was reduced by serine substitution of the cysteine residue at position 64 (AvPAL_C64S), but was not adversely affected by serine substitution of the cysteine residues at either of positions 503 or 565, or at both positions 503 and 565 (AvPAL_C503S, AvPAL_C565S, and AvPAL_C565SC503S, respectively).

TABLE 1

Specific Activity of AvPAL Cysteine Mutants

| AvPAL Protein | PEGylation | Specific Activity (U/mg) |
|---|---|---|
| WT AvPAL | − | 1.7 |
| AvPAL__C503S | − | 1.9 |
| AvPAL__C64S | − | 1.3 |
| AvPAL__C565S E1 | − | 2.0 |
| AvPAL__C565S E2 | − | 2.1 |
| AvPAL__C565SC503S | − | 2.2 |
| WT AvPAL | + | 1.1 |
| AvPAL__C565SC503S | + | 1.1 |

To determine whether the introduction of the serine residues had any effect on enzymatic activity of pegylated AvPAL proteins, the WT AvPAL and double cysteine mutant, AvPAL_C565SC503S, were pegylated as described in EXAMPLE 6. Table 1 shows that the in vitro PAL specific activity of the pegylated AvPAL protein was not adversely affected by serine substitution of the cysteine residues at both positions 503 and 565.

Example 9

In Vitro Biochemical Characterization of AvPAL Variants (Cysteine Mutants)

The purpose of this study was to determine the effect of serine substitution of the various cysteine residues in the AvPAL polypeptide on: (1) accelerated stability; (2) aggregate formation; and (3) site-specific pegylation.

Accelerated Stability

The effect of serine substitution of cysteine residues in AvPAL on in vitro stability was determined by storing the purified AvPAL cysteine mutants, either pegylated or unpegylated, for various time periods at 37° C., and then measuring the in vitro PAL specific activity of these proteins as described in EXAMPLE 3.

Wild-type AvPAL and AvPAL cysteine mutants, either unpegylated or pegylated, were prepared as described in EXAMPLE 8.

As shown in FIG. 6A, the specific activities of the unpegylated AvPAL proteins were stable for at least 5 days at 37° C., and were not adversely affected by serine substitution of the cysteine residues at position 565, or at both positions 503 and 565. Similarly, as shown in FIG. 6B, the specific activities of the pegylated AvPAL proteins were stable for at least 6 days at 37° C. The single cysteine AvPAL mutant, AvPAL_C565S, showed somewhat reduced stability compared to wild-type AvPAL and the double cysteine AvPAL mutant, AvPAL_C565SC503S, after 6 days at 37° C.

Aggregate Formation

The effect of serine substitution of cysteine residues in AvPAL on formation of protein aggregates in solution was determined by separating the purified, unpegylated wild-type AvPAL and AvPAL cysteine mutants by either denaturing and native gel electrophoresis or by SEC-HPLC.

The purified AvPAL preparations were separated by gel electrophoresis under either denaturing conditions (4-12% NuPAGE Bis-Tris) or native conditions (8% Tris-Gly, pH 8.3). The separated AvPAL proteins were stained with Coomassie Blue.

The purified AvPAL preparations were separated by SEC-HPLC. AvPAL proteins were loaded onto a TSK gel column (G3000SWxl, 7.8 mm×30 cm, 5 μm (Tosoh Bioscience, LLC)) in 20 mM Na-phosphate, 300 mM NaCl, pH 6.9, and eluted at a flow rate of 0.5 mL/min. The separated AvPAL proteins were analyzed on an Agilent series 1100 spectrometer.

Aggregates were present in the wild-type AvPAL preparation and in the AvPAL_C503S and AvPAL_C64S preparations, but not in the AvPAL_C565S and AvPAL_C565SC503S preparations, as judged by either gel electrophoresis (FIG. 7A) or SEC-HPLC (FIG. 7B).

Site-Specific Pegylation

The effect of serine substitution of cysteine residues in AvPAL on site-specific pegylation was determined by pegylating the wild-type AvPAL and double cysteine mutant AvPAL_C503SC565S as described in EXAMPLE 6, and then comparing the relative pegylation at the AvPAL lysine residues: K2, K10, K32, K115, K145, K195, K301, K335, K413, K419, K493, K494 and K522.

Approximately 100 μg (10 μL at 10 μg/μL) of unpegylated or pegylated AvPAL proteins were denatured in 8 M urea. The denatured proteins were then digested in a 100 μL reaction volume with trypsin in 0.8 M urea at pH 8.2 overnight (~20 hours) at 37° C. The trypsin-digested proteins were reduced by treatment with 1 μL of 1 M DTT for 1 hour at 37° C., followed by quenching with 3 μL 15% TFA. Digested proteins were separated on a C18 reverse-phase column. Percent pegylation of each of the pegylated AvPAL peptides was calculated by subtractive peptide mapping of the corresponding unpegylated peptide.

As shown in FIG. 8, at a ratio of AvPAL protein:PEG of 1:3, there was no striking difference in the percent pegylation of any of the lysine (K) residues with the possible exception of K419, in which the percent pegylation of the double cysteine mutant C565SC503S was lower compared to wild-type AvPAL. However, the results obtained using the double cysteine mutant at increasing AvPAL protein:PEG ratios, in which no dose-response relationship was observed, taken together with the relatively small percent pegylation, indicates that the observed differences at K1419 are not likely to be meaningful. Thus, serine substitution of cysteine residues at positions 503 and 565 does not appear to affect site-specific pegylation of AvPAL.

Example 10

Mechanism of Aggregation of AvPAL Proteins

Studies were performed to investigate the mechanism of aggregation of bacterially expressed AvPAL proteins.

Concentrating the purified AvPAL preparations, and incubating the concentrated protein solutions for 2 hours at 37° C., accelerated aggregation of purified AvPAL proteins in solution. Aggregation was detected by separating the AvPAL proteins by SEC-HPLC. To determine whether disulfide cross-linking was responsible for the aggregation, 50 mM dithiothreitol (DTT) was added to the concentrated protein solution, followed by incubation for 2 hours at 37° C.

AvPAL proteins expressed in bacteria were purified as described in EXAMPLE 2, and concentrated using a spin filter (Millipore Biomax-10K NMWL). Proteins were spun at about 15,000 g for a few minutes in an Eppendorf Centrifuge 5415C. For cysteine mutants that tend to aggregate (e.g., AvPAL_C503S and AvPAL_C64S), proteins were concentrated to about 20 mg/mL and incubated for 2 hours at 37° C. For cysteine mutants that are resistant to aggregation (e.g., AvPAL_C565S and AvPAL_C565SC503S), proteins were concentrated to about 40 mg/mL and incubated for 2 hours at 37° C.

As shown in Table 2, preparations of purified AvPAL cysteine mutants AvPAL_C64S and AvPAL_C503S formed aggregates upon incubation for 2 hours at 37° C. As expected, this aggregation was exacerbated when the AvPAL proteins were concentrated prior to incubation for 2 hours at 37° C. The aggregation could be blocked by exposure of the concentrated proteins to DTT, indicating that the aggregation is due to disulfide cross-linking. In contrast, the preparations of purified AvPAL cysteine mutants AvPAL_C565S and AvPAL_C565SC503S did not form aggregates upon incubation for 2 hours at 37° C., indicating that the cysteine residue at position 565 is involved in aggregation of AvPAL via disulfide cross-linking.

TABLE 2

Disulfide Cross-link Related Aggregation of AvPAL Cysteine Mutants

| AvPAL Protein | Treatment | Aggregate Formation |
|---|---|---|
| AvPAL_C503S | 37° C./2 h | + |
| AvPAL_C64S | 37° C./2 h | + |
| AvPAL_C565S E1 | 37° C./2 h | – |
| AvPAL_C565S E2 | 37° C./2 h | – |
| AvPAL_C565SC503S | 37° C./2 h | – |
| AvPAL_C503S | Concentrate + 37° C./2 h | ++ |
| AvPAL_C64S | Concentrate + 37° C./2 h | ++ |
| AvPAL_C565S E1 | Concentrate + 37° C./2 h | – |
| AvPAL_C565S E2 | Concentrate + 37° C./2 h | – |
| AvPAL_C565SC503S | Concentrate + 37° C./2 h | – |
| AvPAL_C503S | Conc. + DTT + 37° C./2 h | – |
| AvPAL_C64S | Conc. + DTT + 37° C./2 h | – |
| AvPAL_C565S E1 | Conc. + DTT + 37° C./2 h | – |
| AvPAL_C565S E2 | Conc. + DTT + 37° C./2 h | – |
| AvPAL_C565SC503S | Conc. + DTT + 37° C./2 h | – |

To determine which cysteine residues exist as free sulfhydryls, a purified AvPAL preparation was denatured in the presence of 8 M urea, alkylated by iodoacetamide, digested with trypsin, and analyzed by LC/MS. All of the AvPAL cysteine residues were labeled by iodoacetamide, indicating that all of the cysteine residues of bacterially expressed AvPAL exist as free sulfhydryls (data not shown).

To determine which cysteine residues are present on the surface of the native protein, a purified AvPAL preparation was first treated with N-ethylmaleimide (NEM), then denatured in the presence of 8 M urea, alkylated by iodoacetamide, digested with trypsin, and analyzed by LC/MS. The cysteine residues at positions 235 and 424 were not alkylated by NEM, and the cysteine residue at position 318 was only partially alkylated by NEM, indicating that the cysteine residues at positions 64, 503 and 565 are on the surface of native AvPAL and the cysteine residue at position 318 is partially exposed on the surface of native AvPAL (data not shown).

To determine which cysteine residues are involved in the inter-chain disulfide cross-linking, 67 μL of a 0.7 mg/mL solution of purified, unpegylated wild-type AvPAL preparation was denatured and alkylated in 8 M urea containing 20 mM iodoacetamide for 1 hour at 37° C., and then digested in a 100 μL reaction volume with trypsin at pH 8.2 overnight (~17.5 hours) at 25° C. The trypsin-digested proteins were separated and analyzed by mass spectrometry, in which peptides corresponding to the predicted disulfide pairs were identified and quantitated as total ion counts (TIC).

Table 3 shows that disulfide pairs were detected for C503-C503, C503-C565, C565-C318 and C565-C565. The cysteine residues at position 565, and to a lesser extent at position 503, were found in disulfide pairs in the purified AvPAL preparation.

TABLE 3

Aggregate Disulfide Pairs

| Disulfide Pair | Results (TIC/1000) |
|---|---|
| C64-C318 | n.d.# |
| C64-C64 | n.d. |
| C64-C503 | n.d. |
| C64-C565 | n.d. |
| C503-C318 | n.d. |
| C503-C503 | 11 |
| C503-C565 | 112 |
| C565-C318 | 13 |
| C565-C565 | 37 |
| C318-C318 | n.d. |

#not detected

Studies were performed to determine whether additional mechanisms besides disulfide cross-linking might be involved in AvPAL protein aggregation.

Purified AvPAL preparations were incubated with either 0.05% Tween or 10 mM EDTA, and then separated by SEC-HPLC as described in EXAMPLE 9. Tween reduces protein aggregation due to hydrophobic interactions, and EDTA reduces protein aggregation due to the presence of divalent cations. As shown in FIG. 9, exposure to 0.05% Tween or 10 mM EDTA had no effect on AvPAL protein aggregation. The additional peak at 10 minutes in the 10 mM EDTA treated AvPAL is due to absorbance of EDTA at 210 nm.

To further investigate the role of disulfide cross-linking in AvPAL protein aggregation, purified AvPAL was reduced by treatment with DTT and then desalted prior to separation by SEC-HPLC. As shown in FIG. 10A, AvPAL protein aggregation was minimized by treatment with DTT, and aggregates re-formed following incubation for 18 hours at 37° C. In contrast, as shown in FIG. 10B, aggregates did not re-form once the AvPAL surface cysteines were modified (i.e., alkylated) by treatment with N-methylmaleimide (NEM) after DTT exposure, but before desalting and incubation for 18 hours at 37° C.

Based on the above, aggregation of bacterially expressed AvPAL appears to be due solely to formation of inter-chain disulfide bonds, and not due to hydrophobic effects or presence of divalent cations. The cysteine residues at positions 565 and 503 are involved in formation of inter-chain disulfide bonds in AvPAL preparations.

Example 11

Liquid Formulations of PEGylated Forms of AvPAL Variants (Cysteine Mutants)

Studies were performed to investigate the effect of various excipients, e.g., stabilizers, on the accelerated stability of a PEGylated form of an AvPAL polypeptide variant (e.g., with serine substitution of the cysteine residues at positions 503 and 565) in formulations of the invention.

The pegylated AvPAL double cysteine mutant AvPAL_C565SC503S was prepared as described in EXAMPLE 7.

Accelerated stability of different formulations of pegylated AvPAL_C565SC503S was determined using an in vitro activity assay, either a cuvette assay or a plate assay. For the cuvette assay, purified pegylated AvPAL_C565SC503S was diluted in TBS dilution buffer and then added to an assay buffer containing 22.5 mM phenylalanine (Phe), 100 mM Tris-HCl, pH 8.5. After incubation for 2 minutes at 30° C., the amount of trans-cinnamic acid (t-CA) released was measured by absorbance at 290 nm. For the plate assay, purified pegylated AvPAL_C565SC503S was diluted in TBS dilution buffer plus BSA/Phe/Brij and then added to an assay buffer containing 22.5 mM Phe, 100 mM Tris-HCl, pH 8.5. After incubation for 10-20 minutes at 30° C., the amount of trans-cinnamic acid (t-CA) released was measured by absorbance at 290 nm. One IU of PAL activity is equal to 1 μMol TCA/min.

In a first accelerated stability study, the effect of pH on stability of the pegylated double cysteine mutant AvPAL AvPAL_C565SC503S was evaluated. Purified pegylated AvPAL_C565SC503S was pre-formulated in 10 mM buffer and 140 mM NaCl at various pH, from 4 to 9. Buffers tested: citrate (pH 4), acetate (pH 5), histidine (pH 6), phosphate (pH 7), Tris (pH 7.5, pH 8) and arginine (pH 9). After storing the enzyme formulations for up to 30 days at 4° C., 25° C. or 37° C., in vitro activity was measured. A total loss of PAL enzyme activity was observed at pH 4. A pH range from 7 to 8 was chosen for further evaluation.

In a second accelerated stability study, the effect of pH and a variety of excipients on stability of the pegylated AvPAL double cysteine mutant AvPAL_C565SC503S was evaluated. Purified pegylated AvPAL_C565SC503S was pre-formulated in 10 mM Tris and 140 mM NaCl at pH 7, 7.5 or 8.0 in the absence or presence of 0.5% EDTA, 0.5% EDTA plus 0.5% ascorbic acid or 0.5% EDTA plus 5 mM methionine (Met). After storing the enzyme formulations for up to 60 days at 4° C., 25° C. or 37° C., in vitro activity was measured. pH 7.0 and 7.5 appeared equivalent in maintaining enzyme activity, EDTA had little or no effect on enzyme activity, and the anti-oxidants ascorbic acid and methionine negatively affected enzyme activity.

In the same accelerated stability study, the effect of pegylation of the AvPAL double cysteine mutant AvPAL_C565SC503S was evaluated. The rate of loss of enzyme activity was similar between unpegylated and pegylated AvPAL_C565SC503S.

In a third accelerated stability study, the effect of enzyme substrate and product as excipient on stability of the pegylated AvPAL double cysteine mutant AvPAL_C565SC503S was evaluated. Purified pegylated AvPAL_C565SC503S at approximately 12 mg/mL (0.2 mM) was pre-formulated in 10 mM Tris and 140 mM NaCl at pH 7.5 in the absence or presence of 1 mM Phe (substrate at 5 moles per mole active site), 2 mM TCA (product at 10 moles per mole active site) or 0.05% Tween 80 (a surfactant). After storing the enzyme formulations for various times at 4° C., 25° C. or 37° C., in vitro activity was measured weekly. Both Phe and t-CA significantly increased stability of the enzyme, whereas Tween had no effect on enzyme stability.

A summary of the accelerated stability studies 1, 2 and 3 is shown in FIG. 11.

In a fourth accelerated stability study, the effect of Phe and t-CA at low concentrations as excipient on stability of the pegylated AvPAL double cysteine mutant AvPAL_C565SC503S was evaluated. Purified pegylated AvPAL_C565SC503S at approximately 12 mg/mL (0.2 mM) was pre-formulated in 10 mM Tris and 140 mM NaCl at pH 7.5 in the absence or presence of 0.4 mM Phe (substrate at 2 moles per mole active site) or 0.4 mM TCA (product at 2 moles per mole active site). After storing the enzyme formulations for various times at 4° C., 25° C. or 37° C., in vitro activity was measured weekly. Both Phe and t-CA at low concentration were effective at stabilizing enzyme activity.

In a fifth accelerated stability study, the effect of a weak enzyme substrate, tyrosine (Tyr), as excipient on stability of the pegylated AvPAL double cysteine mutant AvPAL_C565SC503S was evaluated. Purified pegylated AvPAL_C565SC503S at approximately 12 mg/mL (0.2 mM) was pre-formulated in 10 mM Tris and 140 mM NaCl at pH 7.5 in the absence or presence of 1 or 5 mM Tyr (substrate at 5 or 25 moles per mole active site, respectively). After storing the enzyme formulations for various times at 4° C., 25° C. or 37° C., in vitro activity was measured weekly. Tyr had a minimal, non-dose dependent stabilizing effect on enzyme activity (FIG. 12).

In a sixth accelerated stability study, the effect of nucleophilic scavengers as excipient on stability of the pegylated AvPAL double cysteine mutant AvPAL_C565SC503S was evaluated. Purified pegylated AvPAL_C565SC503S at approximately 20 mg/mL (0.33 mM) was pre-formulated in 10 mM Tris and 140 mM NaCl at pH 7.5 in the absence or presence of 1 Phe (substrate at 3 moles per mole active site), 2 mM nucleophilic scavenger (either benzoic acid or pyridoxamine at 6 moles per mole active site), or both 1 mM Phe and 2 mM nucleophilic scavenger. After storing the enzyme formulations for various times at 4° C. or 37° C., in vitro activity was measured weekly. Benzoic acid, but not pyridoxamine, was effective at stabilizing enzyme activity (FIG. 13A). There was no additive effect of Phe and benzoic acid, suggesting a similar stabilizing mechanism.

The stabilizing effects of benzoic acid and t-CA suggest that they function as structural analogs of Phe (see FIG. 13B).

The data from the six accelerated stability studies were combined in order to predict the effective shelf-life of the pegylated AvPAL double cysteine mutant AvPAL_C565SC503S in various formulations. Shelf-life was determined as follows: (1) determining the rate of activity decay ($k_{decay}$) which followed first order kinetics, for each formulation condition; (2) plotting the $\ln(k_{decay})$ v. 1/Temperature (° K); (3) determining the Ea ($\Delta G_{decay}$) required for activity decay for a given formulation condition; (4) extrapolating the $k_{decay}$ at 4° C. using the calculated Ea and the observed $k_{decay}$ at a given temperature; and (5) determining the shelf life ($T_{90}$), which is the time in which specific enzyme activity has dropped by ≧10% at 4° C.

Table 4 shows that Phe and t-CA greatly enhances the predicted shelf-life of the pegylated AvPAL double cysteine mutant AvPAL_C565SC503S.

TABLE 4

Predicted Shelf-Life $T_{90}$ (in Weeks) of Pegylated Double Cysteine Mutant AvPAL_C565SC503S with Various Excipients

| Excipient | 42° C. | 37° C. | 25° C. | 4° C.* | 4° C. (Observed) |
|---|---|---|---|---|---|
| None (TBS) | 0.67 | 0.8 | 2.1 | 12.9 | ~9-13 |
| Phe | 1.63 | 2.2 | 9.1 | 85 | >20 |
| t-CA | ND | 2.0 | 7.1 | 85.8 | >20 |

*Numbers are estimates based on data from up to 6 different experiments.

In summary, the above preformulation studies indicate that the pH optimum for the pegylated AvPAL double cysteine mutant AvPAL_C565SC503S is 7 to 7.5. The presence of anti-oxidants result in a drastic loss of enzyme activity. Both phenylalanine (Phe) and trans-cinnamic acid (t-CA) increase the stability of rAvPAL-PEG by 50% or more under accelerated conditions (25° C. and 37° C.). A 2-fold excess Phe or t-CA per rAvPAL-PEG active site is sufficient to stabilize activity and higher concentrations appear to have no additional benefit. A weaker PAL substrate, tyrosine (Tyr), does not appear to stabilize enzyme activity, whereas benzoic acid, stabilizes rAvPAL-PEG activity to a similar degree as its structural analog, Phe. When combined with Phe, no additional activity stabilization is observed with benzoic acid, suggesting a common mechanism for activity stabilization.

Example 12

Lyophilized Formulations of PEGylated Forms of AvPAL Variants (Cysteine Mutants)

Studies were performed to investigate the effect of various solid (e.g., lyophilized) formulations on the activity of a PEGylated form of an AvPAL polypeptide variant (e.g., with serine substitution of the cysteine residues at positions 503 and 565) of the invention.

The pegylated AvPAL double cysteine mutant AvPAL_C565SC503S was prepared as described in EXAMPLE 7.

The pegylated AvPAL double cysteine mutant AvPAL_C565SC503S was formulated as follows: (F1) 10 mg/mL AvPAL_C565SC503S, 10 mM Tris, pH 7.5; (F2) 10 mg/mL AvPAL_C565SC503S, 10 mM Tris, pH 7.5, 25 mg/mL mannitol; or (F3) 10 mg/mL AvPAL_C565SC503S, 10 mM Tris, pH 7.5, 20 mg/mL mannitol, 5 mg/mL sucrose. After formulation, the PAL enzyme activity of each was 1.7 to 1.8 U/mg. After lyophilization, the formulations were stored for up to 26 at 4° C., and then resuspended in fresh, sterile-filtered MilliQ water. The PAL enzyme activities were determined as described in EXAMPLE 11. Table 5 shows that there appeared to be no loss of activity upon lyophilization, storage or resuspension of the various AvPAL_C565SC503 S formulations.

TABLE 5

Specific Activity of Pegylated Double Cysteine Mutant AvPAL_C565SC503S Upon Lyophilized Formulation (LF)

| LF | Before LF | After LF | After LF + 5 days/ 4° C. | After LF + 11 days/4° C. | After LF + 26 days/4° C. |
|---|---|---|---|---|---|
| F1 | 1.78 +/− 0.04 | 1.60 | 1.59 | 1.71 | 1.48 |
| F2 | 1.72 +/− 0.01 | 1.67 | 1.62 | 1.68 | 1.72 |
| F3 | 1.65 +/− 0.09 | 1.66 | 1.73 | 1.76 | 1.59 |

Example 13

Toxicity/Pharmacokinetic Studies of PEGylated Forms of AvPAL Variants (Cysteine Mutants) in Cynomolgus Monkeys and Rats Toxicity/pharmacokinetic studies were performed to determine the effect of administration of a single dose of a PEGylated form of an AvPAL polypeptide variant (e.g., with serine substitution of the cysteine residues at positions 503 and 565) in Cynomolgus monkeys and in rats.

The pegylated AvPAL double cysteine mutant AvPAL_C565SC503S was prepared as described in EXAMPLE 7.

Cynomolgus Monkey Toxicity/Pharmacokinetic Study

This study used four (4) groups of monkeys, each with three males and three females. Group 1 received placebo (mL/kg); and Groups 2, 3 and 4 received a single subcutaneous injection of pegylated AvPAL double cysteine mutant AvPAL_C565SC503S in solution at 4, 12 and 60 mg/kg, respectively. Plasma samples were collected from the monkeys pre-dose, and at various times post-dose, from 3 to 504 hours. The 60 mg/kg dose was found to be toxic to the monkeys, so the Group 4 portion of this study was terminated.

FIG. 14A shows the concentration of pegylated AvPAL double cysteine mutant AvPAL_C565 SC503 S in the plasma at various times after a single subcutaneous injection at 4 and 12 mg/kg. The data shows monophasic elimination of the pegylated AvPAL double cysteine mutant AvPAL_C565SC503S. A single compartment model with $1^{st}$ order absorption appears to describe the plasma profile of the pegylated AvPAL double cysteine mutant AvPAL_C565SC503S after a single subcutaneous injection.

FIG. 14B shows the concentrations of phenylalanine (Phe) and pegylated AvPAL double cysteine mutant AvPAL_C565SC503S in the plasma at various times after a single subcutaneous injection at 4 mg/kg. At this dose, the plasma Phe concentration was reduced to below the limit of quantitation in the GC/MS assay within 24 hours, and the drop in plasma Phe was sustained over 10 days.

Rat Toxicity/Pharmacokinetic Study

This study used eight (8) groups of rats, with 3 males and 3 females in the placebo groups, and 6 males and 6 females in the test groups. Groups 1 and 5 received single intravenous and subcutaneous injections of placebo. Groups 2, 3 and 4 received single intravenous injections of pegylated AvPAL double cysteine mutant AvPAL_C565SC503S at 1, 5 and 25 mg/kg, respectively. Groups 6, 7 and 8 received single subcutaneous injections of pegylated AvPAL double cysteine mutant AvPAL_C565SC503S at 10, 25 and 250 mg/kg, respectively. Blood samples were collected from the rats pre-dose, and at various times post-dose, from 1 to 360 hours. At each collection time, blood was collected from 3 rats in each group. No toxicity was observed in the rats in this study.

FIG. 15A shows the concentration of pegylated AvPAL double cysteine mutant AvPAL_C565SC503S in the plasma at various times after a single intravenous injection at 1, 5 and 25 mg/kg. The data shows monophasic elimination of the pegylated AvPAL double cysteine mutant AvPAL_C565SC503S from the plasma after a single intravenous injection.

FIG. 15B shows the concentration of pegylated AvPAL double cysteine mutant AvPAL_C565SC503S in the plasma at various times after a single subcutaneous injection at 10, 25 and 250 mg/kg. A single compartment model with first order absorption appears to describe the plasma profile of the pegylated AvPAL double cysteine mutant AvPAL_C565SC503S after a single subcutaneous injection.

Figure 3:
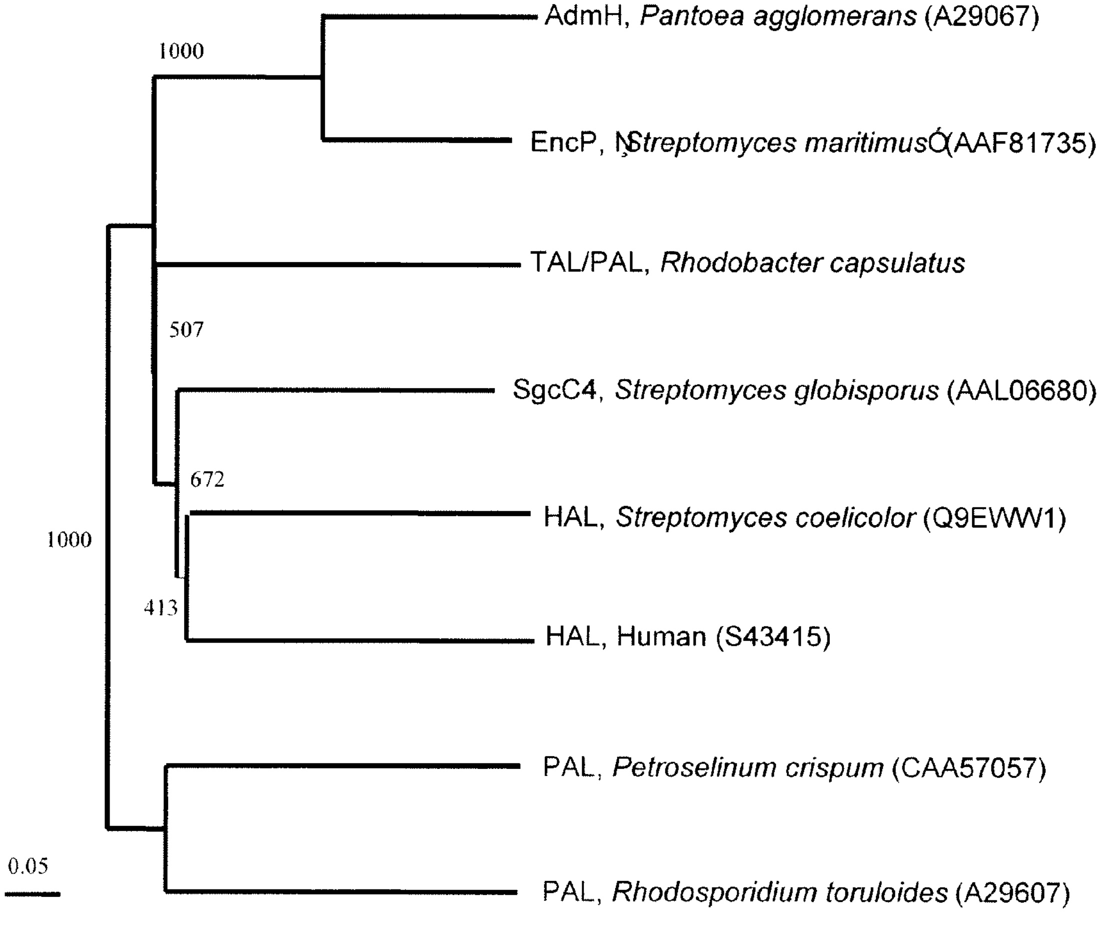
Figure 6A:
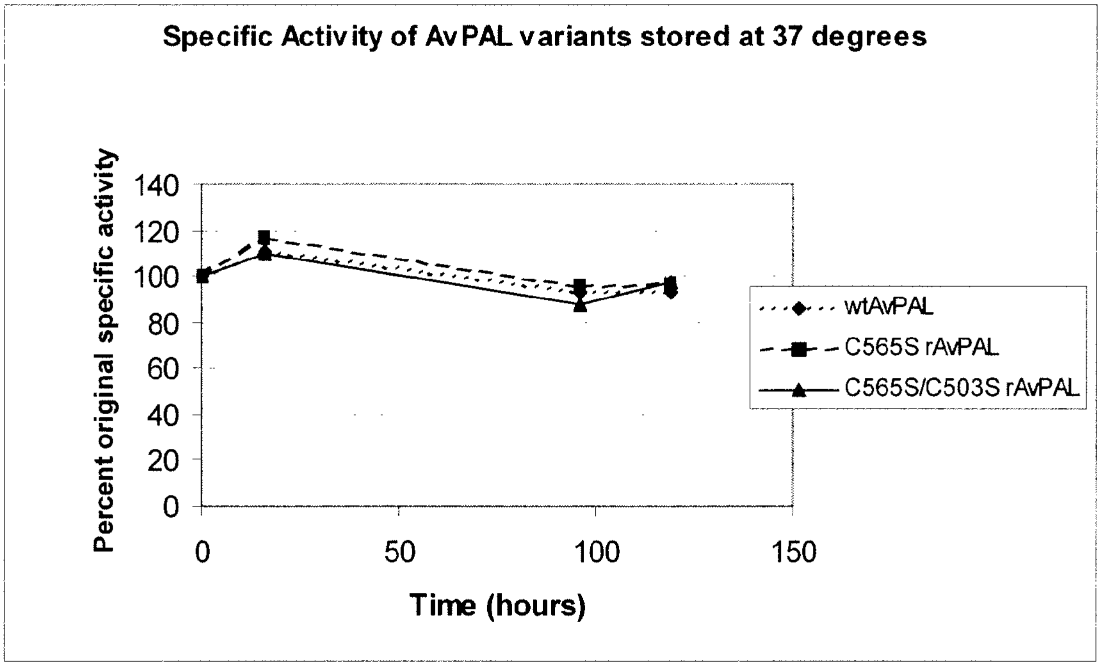
Figure 6B:
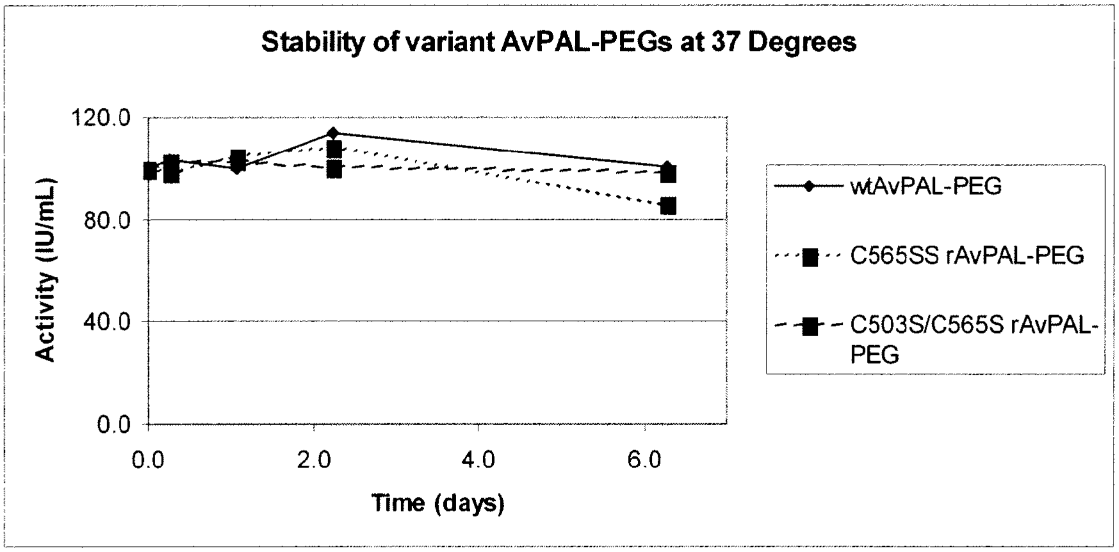
Figure 7A:
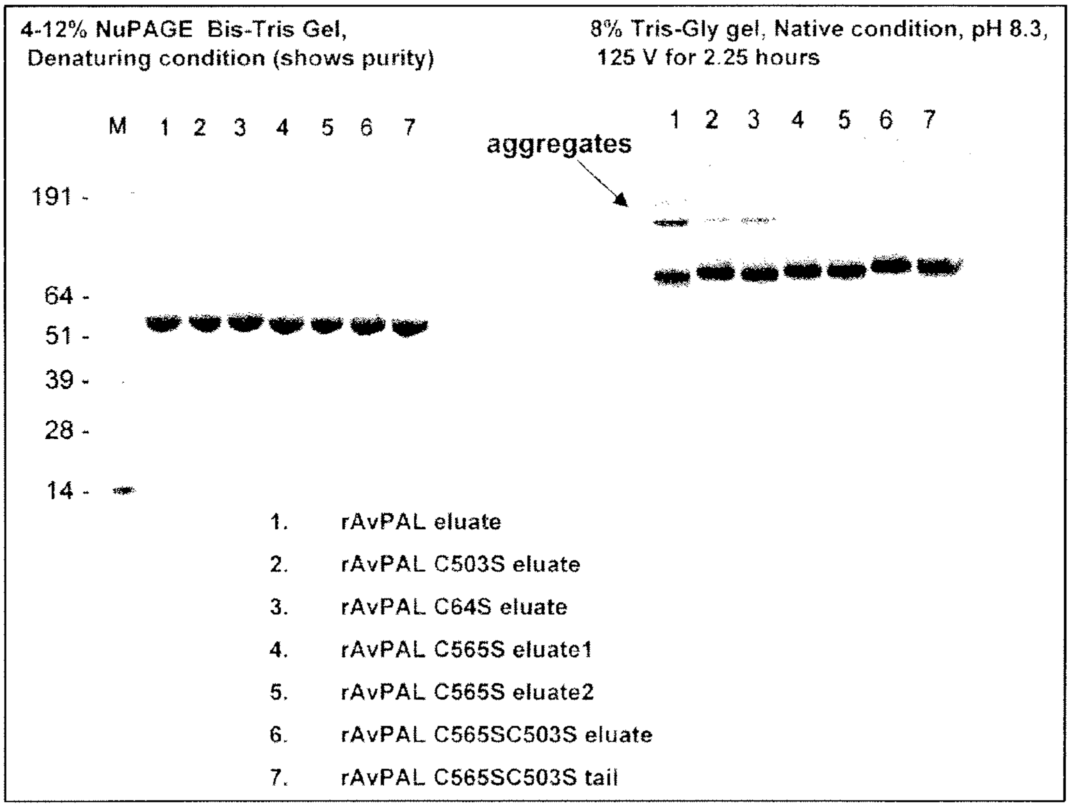
Figure 7B:
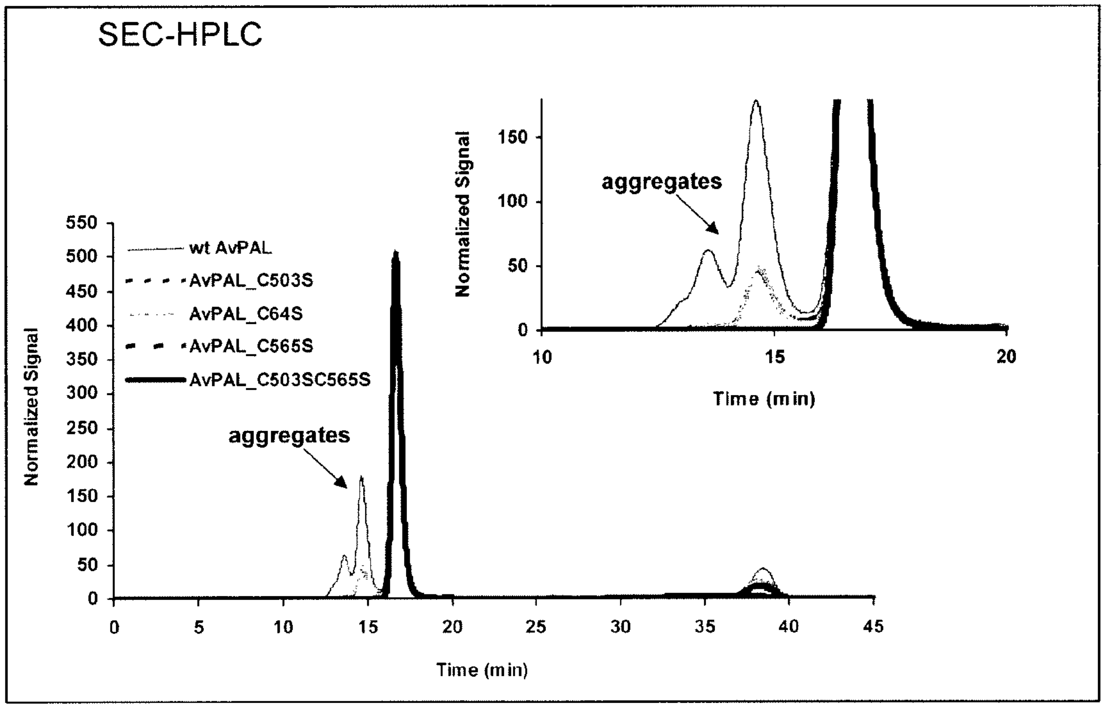
Figure 8:
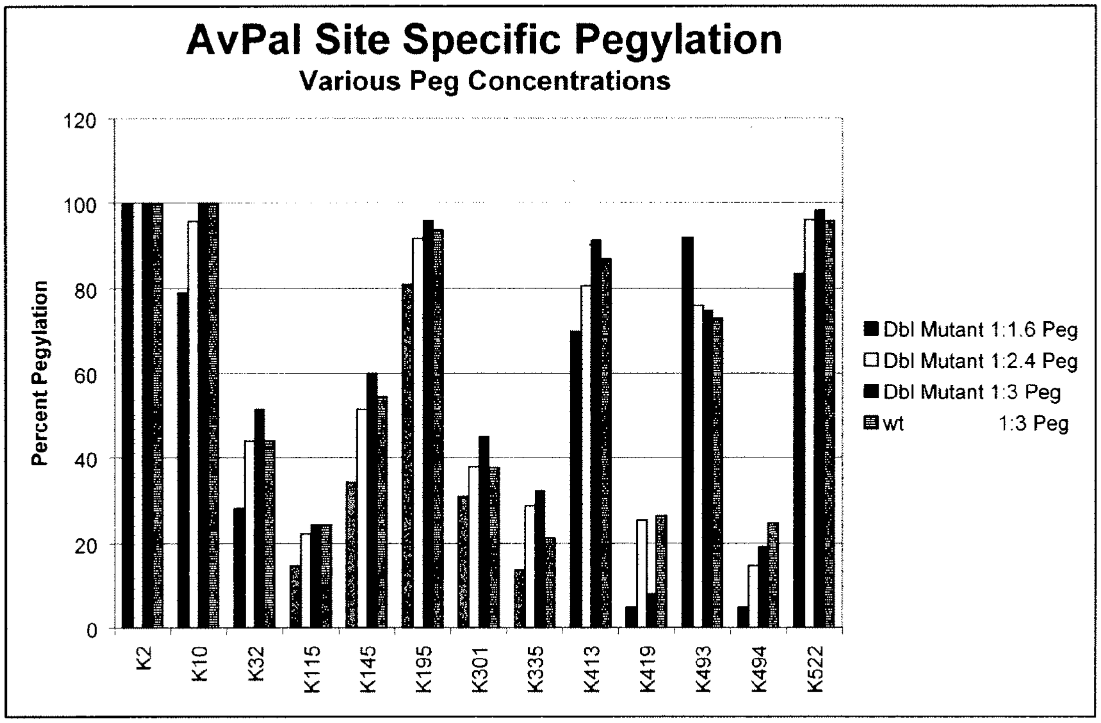
Figure 9:
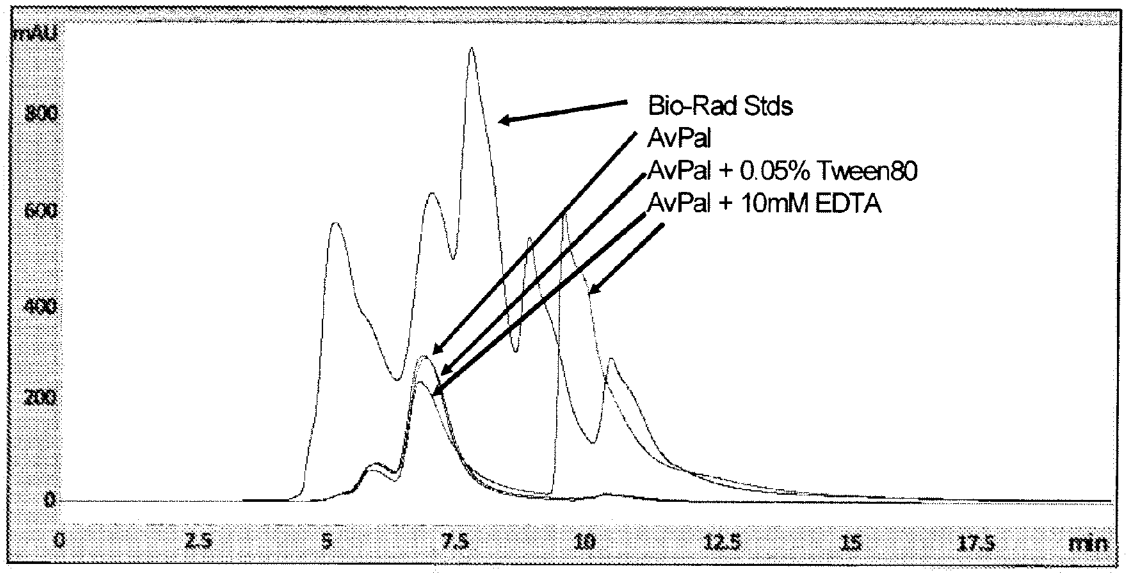
Figure 10A:
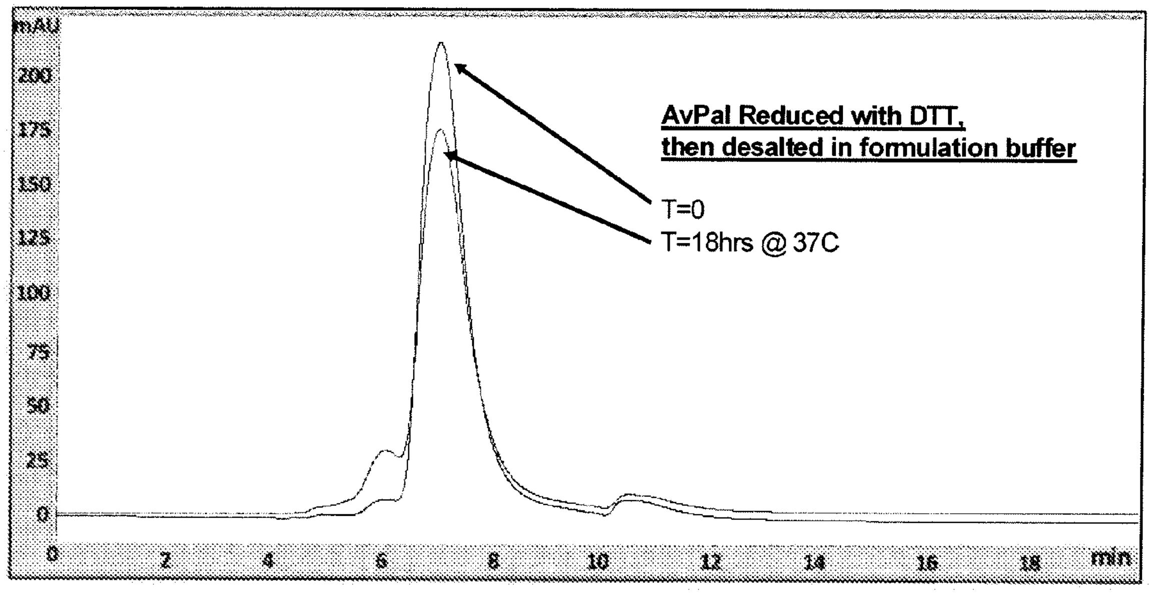
Figure 10B:
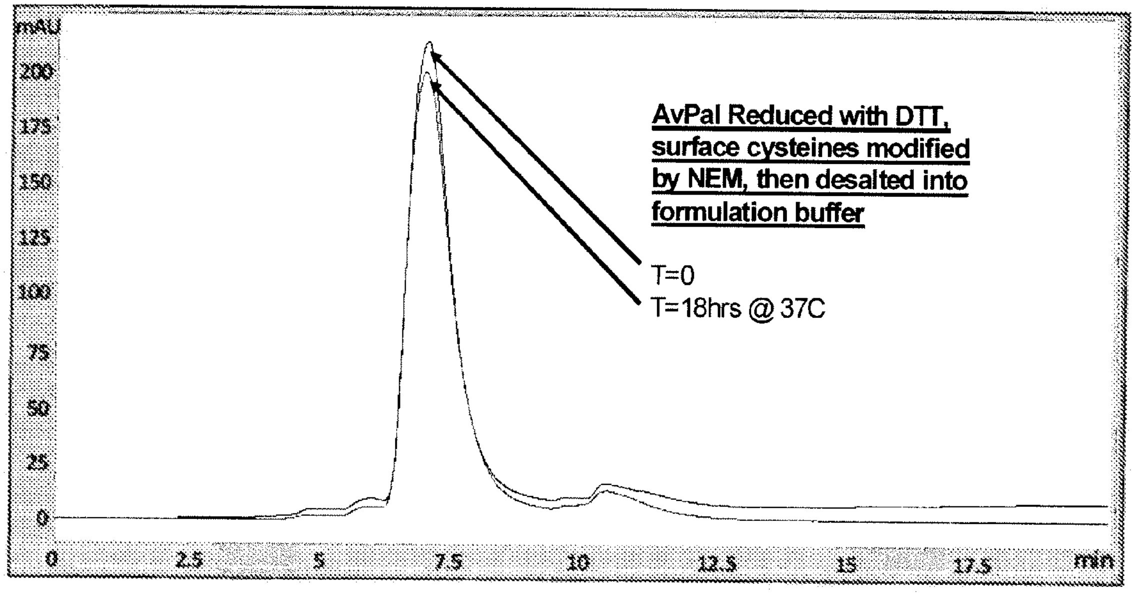
Figure 12:
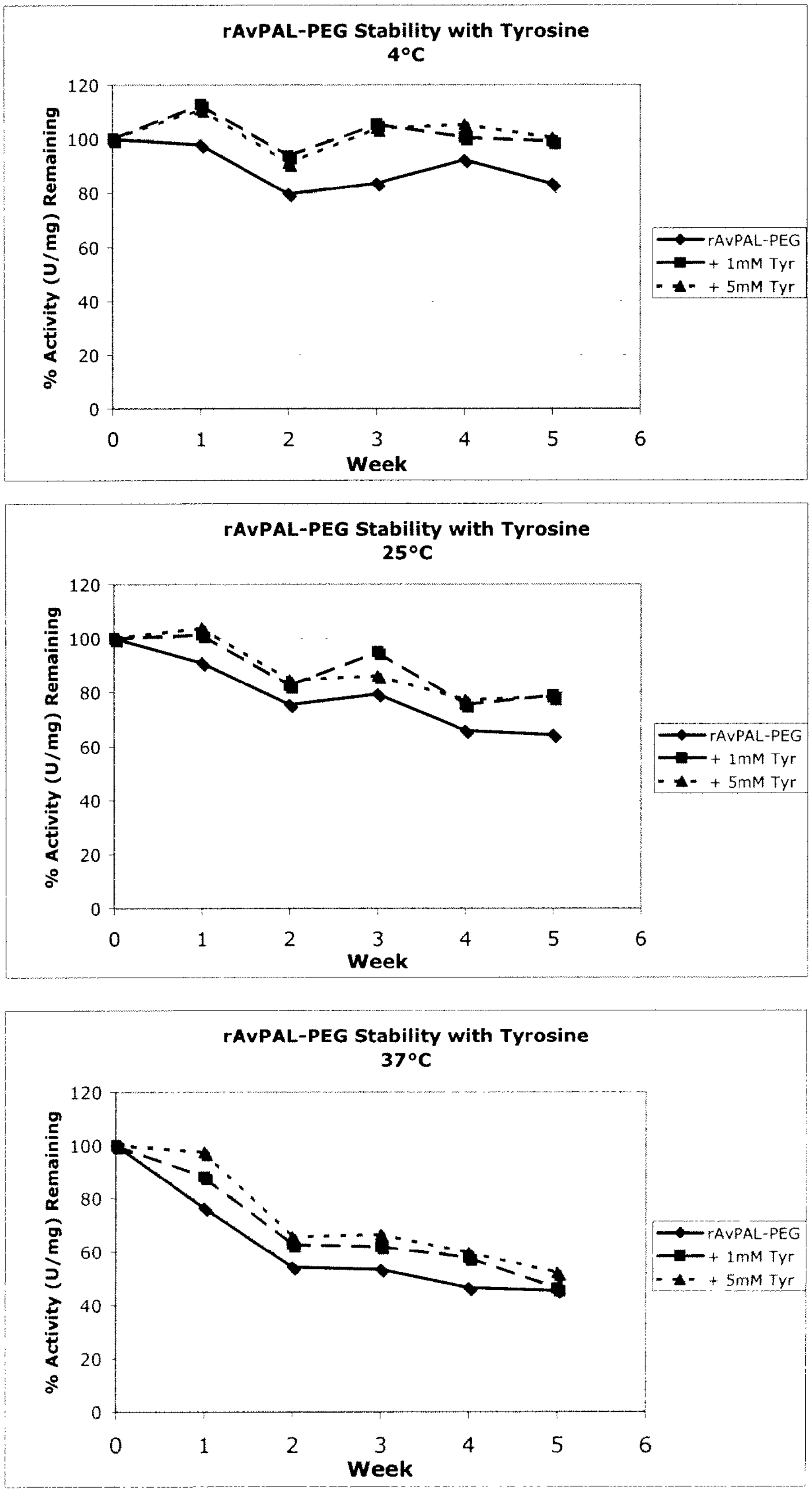

Table 6 shows pharmacokinetic parameters of the pegylated AvPAL double cysteine mutant AvPAL_C565SC503S after a single intravenous or subcutaneous injection.

TABLE 6

Pharmacokinetic Parameters of Pegylated Double Cysteine Mutant AvPAL_C565SC503S After a Single Intravenous or Subcutaneous Dose

| Route | Dose (mg/kg) | $AUC_{0-\infty}$ (ng-hr/mL) | $C_{max}$ (ng/mL) | $T_{max}$ (hr) | $t_{1/2}$* (hr) | F (%) |
|---|---|---|---|---|---|---|
| Intravenous | 1 | 657131 | 12600 | 4.5 | 27.9 | — |
| | 5 | 3579327 | 87667 | 2 | 39.1 | — |
| | 25 | 10860907 | 202238 | 9.0 | 30.4 | — |
| Subcutaneous | 10 | 1304016 | 16674 | 18.0 | 46.9 | 19.7 |
| | 25 | 2290754 | 29260 | 42.0 | 21.0 | 12.5# |
| | 250 | 37254683 | 225200 | 72.0 | 62.8 | 34.0 |

*For the subcutaneous route of administration, terminal $t_{1/2}$ is longer than intravenous; this may be due to a slower rate of absorption from subcutaneous tissues than the rate of elimination (so that the $t_{1/2}$ observed is actually absorption).

#Bioavailability using intravenous AUC data at 25 mg/kg is 21.5%.

There appeared to be no gender difference in this pharmacokinetic study. The $AUC_{inf}$ and $C_{max}$ were roughly proportional with dose for both the intravenous and subcutaneous routes of administration.

Multiple Dose Toxicity Studies in Rats and Cynomolgus Monkeys

The safety of pegylated AvPAL double cysteine mutant AvPAL_C565SC503S was evaluated in repeat-dose toxicity studies in rats and Cynomolgus monkeys.

Rats administered up to 25 mg/kg pegylated AvPAL double cysteine mutant AvPAL_C565SC503S twice weekly, subcutaneously over 28 days exhibited no toxicity.

Cynomolgus monkeys administered up to doses of 1 mg/kg pegylated AvPAL double cysteine mutant AvPAL_C565SC503 S twice weekly, subcutaneously over 28 days exhibited no significant toxicity. A dose dependent decrease in plasma Phe levels was observed after the first dose; however, after the seventh dose, plasma Phe levels returned to baseline in all dose groups, indicating a possible antibody response toward the administered enzyme. Minimal anti-AvPAL_C565SC503S IgG titers were observed in most 1 mg/kg treated animals at day 28. No IgM titers were observed in any animal in the study at day 28.

Example 14

Effects of AvPAL Variants (Cysteine Mutants) on Tumor Cells in Culture

Studies were performed to investigate the effect a PEGylated form of an AvPAL polypeptide variant (e.g., with serine substitution of the cysteine residues at positions 503 and 565) on the proliferation of tumor cells grown in culture in vitro.

The pegylated AvPAL double cysteine mutant AvPAL_C565SC503S was prepared as described in EXAMPLE 7.

The proliferation of tumor cells in vitro was measured using a propidium iodide fluorescence assay as described in Dengler, et al., Anti-Cancer Drugs 6:522-532 (1995).

Hematological Tumors

A panel of twenty-four (24) hematological tumor cell lines, including 14 leukemias, 5 lymphomas and 5 myelomas, were evaluated for the effect of pegylated double cysteine mutant AvPAL_C565SC503S on cell proliferation in vitro.

The hematological tumor cell lines were seeded into culture plates at 5,000 cells/well on Day 0. On Day 1, pegylated double cysteine mutant AvPAL_C565SC503S was added to the cultures at various concentrations, from 0.01 to 100 μg/mL. On Day 5, cells were harvested and DNA content was measured by propidium iodide staining. The $IC_{50}$, $IC_{70}$ and $IC_{90}$ were determined. These experiments were performed twice or three times for each hematological tumor cell line.

Table 7 shows that pegylated double cysteine mutant AvPAL_C565SC503S was effective in inhibiting in vitro proliferation, as measured by propidium iodide staining, of several hematological tumor cell lines.

TABLE 7

Inhibition of Propidium Iodide Staining of Hematological Tumor Lines In Vitro by Pegylated Double Cysteine Mutant AvPAL_C565SC503S

| Tumor Line | Cell Type | $IC_{50}$ μg/mL | $IC_{70}$ μg/mL |
|---|---|---|---|
| CCRF CEM | ALL - T Cell Lymphoma | 1 | >100 |
| | | >100 | >100 |
| | | >100 | >100 |
| EM2 | CML | >100 | >100 |
| | | >100 | >100 |
| | | >100 | >100 |
| HL-60 | APL | 0.904 | >100 |
| | | >100 | >100 |
| | | 46.41 | >100 |
| JURKAT | Human T Cell Leukemia | 0.38 | 2.928 |
| | | 14.125 | >100 |
| | | 10.000 | >100 |
| JURLMK1 | CML | 0.766 | >100 |
| | | 10 | >100 |
| | | 3.162 | >100 |
| K562 | CML | 0.701 | 59.948 |
| | | >100 | >100 |
| | | 11.659 | >100 |
| KCL22 | CML | 0.9 | 15.399 |
| | | >100 | >100 |
| | | 1 | >100 |
| KG1 | AML | 43.287 | >100 |
| | | >100 | >100 |
| | | >100 | >100 |
| MEG01 | CML | 1.258 | >100 |
| | | >100 | >100 |
| | | 0.926 | >100 |
| MOLT4 | ALL - T cell lymphoma | 0.326 | 1.873 |
| | | 1.082 | 5.298 |
| | | 1.096 | 6.918 |
| Mv411 | AML | 5.994 | 74.989 |
| | | >100 | >100 |
| | | >100 | >100 |
| NOMO1 | AML | 0.304 | 2.511 |
| | | 0.732 | 8.659 |
| | | 0.863 | 6.449 |
| OCIAML2 | AML | 0.261 | 0.938 |
| | | >100 | >100 |
| | | 7.305 | >100 |
| PL21 | AML | >100 | >100 |
| | | >100 | >100 |
| | | >100 | >100 |
| HUT78 | Lym CTL | 6.105 | 18.276 |
| | | 17.782 | >100 |
| | | 0.096 | >100 |
| L5178Y | Mouse T cell Leukemia | 6.683 | 41.595 |
| | | 3.981 | 10 |
| | | 3.019 | 7.585 |
| MYLA | Lym CTL | 4.436 | >100 |
| | | 5.379 | >100 |
| | | 8.171 | >100 |
| RAJI | Burkitt Lymphoma | 0.261 | 0.938 |
| | | 21.544 | >100 |
| | | 2.154 | >100 |
| U937 | Histio Lymphoma | 0.803 | >100 |
| | | >100 | >100 |
| | | >100 | >100 |
| 8226 | Myeloma | 0.229 | 0.825 |
| | | >100 | >100 |
| | | 0.691 | 7.742 |
| IM9 | Human Lymphoblastic Cells | 0.271 | 1.467 |
| | | 0.295 | 1.311 |
| | | 0.063 | 0.188 |
| L363 | Human Plasma Cell Leukemia | 7.943 | >100 |
| | | 1.73 | 15.505 |
| LP1 | Human Multiple Myeloma | 0.774 | 100 |
| | | 0.71 | 6.309 |
| NCIH929 | Human Multiple Myeloma | >100 | >100 |
| | | 11.288 | >100 |
| | | 2.154 | >100 |

Dose-dependent inhibition of cell proliferation, as determined by a reduction in propidium iodide staining, by the pegylated double cysteine mutant AvPAL_C565SC503S in two sensitive hematological tumor cells, NOMO1 and IM9, are shown in FIGS. 14A and 21B, respectively. These tumor cell lines had $IC_{50}$ and $IC_{70}$ of less than 1.0 and 10.0 μg/mL, respectively. For comparison, asparaginase has an $IC_{50}$ of 1-10 μg/mL in human leukemia cell lines. In general, however, the hematological tumor cell lines were more resistant, as judged by $IC_{70}$ values, than the solid tumor lines (see below).

Solid Tumors

A panel of thirty-six (36) solid tumor cell lines, including tumors derived from bladder, brain, colon, stomach, head and neck, lung, breast, ovary, pancreas, prostate, kidney and uterus, were evaluated for the effect of pegylated double cysteine mutant AvPAL_C565SC503S on cell proliferation in vitro. The solid tumor cell lines were seeded into culture plates at 5,000 cells/well on Day 0. On Day 1, pegylated double cysteine mutant AvPAL_C565SC503S was added to the cultures at various concentrations, from 0.01 to 100

μg/mL. On Day 5, DNA content was measured by propidium iodide staining. The $IC_{50}$, $IC_{70}$ and $IC_{90}$ were determined.

Table 8 shows that pegylated double cysteine mutant AvPAL_C565SC503S was effective in inhibiting in vitro proliferation, as measured by propidium iodide staining, of several solid tumor cell lines.

TABLE 8

Inhibition of Propidium Iodide Staining of Solid Tumor Lines In Vitro by Pegylated Double Cysteine Mutant AvPAL_C565SC503S

| Tumor Line | Organ/Cell Type | $IC_{50}$ μg/mL | $IC_{70}$ μg/mL |
|---|---|---|---|
| | Bladder | | |
| 1218L | ATCC, Freiburg; Urothelial Adenocarcinoma | 1.1 | 7.498 |
| T24 | Xenograft | 0.617 | 2.154 |
| | Brain/CNS | | |
| 498NL | Xenograft, Freiburg | 0.691 | 2.154 |
| SF268 | NCI | 0.59 | 1.492 |
| | Colon | | |
| HCT116 | NCI; Adenocarcinoma, pd | 0.316 | 0.9 |
| HT29 | NCI; Adenocarcinoma, pd | 0.508 | 0.94 |
| | Gastric | | |
| 251L | Xenograft, Freiburg; Adenocarcinoma, pd | 2.682 | 37.275 |
| | Head and Neck | | |
| 536L | Xenograft, Freiburg; Hypopharynx Carcinoma | 0.606 | 1.887 |
| | Lung | | |
| 1121L | Xenograft | 0.715 | 3.548 |
| 289L | Xenograft, Freiburg; Adenocarcinoma, pd | 2.807 | 23.101 |
| 529L | Xenograft, Freiburg; Large Cell, du | 0.539 | 1.73 |
| 629L | Xenograft, Freiburg; Adenocarcinoma, pd | 0.457 | 1.467 |
| H460 | NCI; Large Cell Carcinoma | 0.215 | 0.644 |
| | Breast | | |
| 401NL | Xenograft, Freiburg; Pap Adenocarcinoma, wd | 1.873 | 7.564 |
| MCF7 | NCI; Mammary Carcinoma | 0.599 | 1.623 |
| | Melanoma | | |
| 276L | Xenograft | 4.124 | 268.269 |
| 394NL | Xenograft | 0.887 | 3.856 |
| 462NL | Xenograft | 0.954 | 6.189 |
| 514L | Xenograft | 0.828 | 4.216 |
| 520L | Xenograft | 1.359 | 6.309 |
| | Ovarian | | |
| 1619L | Xenograft, Freiburg; Adenocarcinoma, md | 0.322 | 0.688 |
| 899L | Xenograft, Freiburg; Pap Serous Carcinoma, md | 1.279 | 6.628 |
| OVCAR3 | NCI; Adenocarcinoma, md | 1.185 | 6.528 |
| | Pancreatic | | |
| 1657L | Xenograft, Freiburg; Adenocarcinoma, md | 1.951 | 8.619 |
| PANC1 | ATCC | 0.825 | 5.179 |
| | Prostate | | |
| 22RV1 | ATCC; Adenocarcinoma, md | 0.87 | 7.079 |
| DU145 | NCI; Adenocarcinoma, md | 0.622 | 1.873 |
| LNCAP | DSMZ; Adenocarcinoma, md | 0.584 | 0.974 |
| PC3M | NCI; Adenocarcinoma, md | 0.501 | 1.274 |
| | Pleuramesothelioma | | |
| 1752L | Xenograft, Freiburg; Pleuramesothelioma | 1.637 | 8.483 |

TABLE 8-continued

Inhibition of Propidium Iodide Staining of Solid Tumor Lines In Vitro by Pegylated Double Cysteine Mutant AvPAL_C565SC503S

| Tumor Line | Organ/Cell Type | $IC_{50}$ μg/mL | $IC_{70}$ μg/mL |
|---|---|---|---|
| | Renal | | |
| 1781L | Xenograft, Freiburg; Renal Carcinoma | 2.371 | 10 |
| 393NL | Xenograft, Freiburg; Hypernephroma, wd | 0.55 | 1.995 |
| 486L | Xenograft | 0.859 | 5.336 |
| 944L | Xenograft | 0.71 | 3.727 |
| | Uterine | | |
| 1138L | Xenograft, Freiburg; Carcinosarcoma, wd | 0.621 | 1.258 |

Figure 17D:
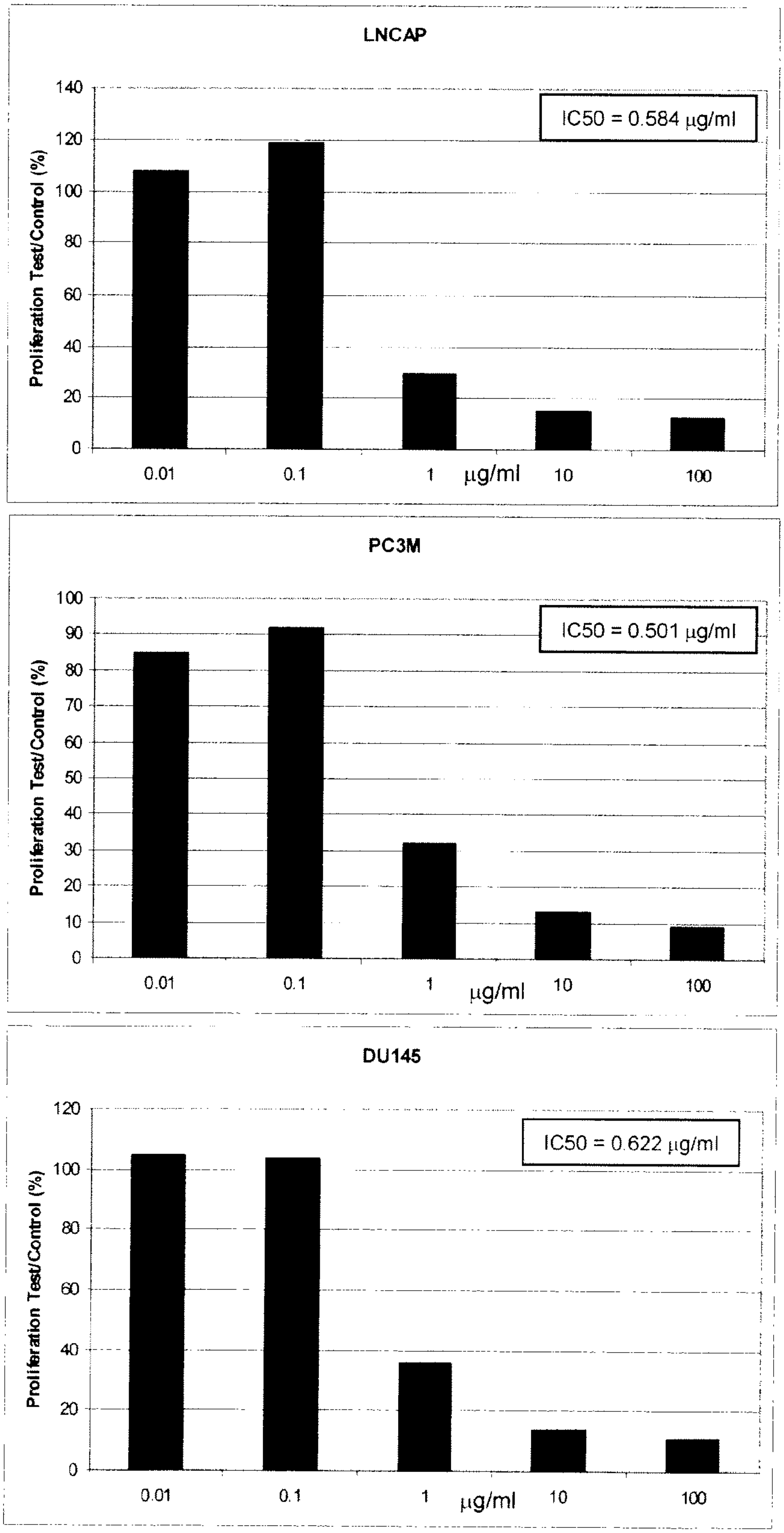

Dose-dependent inhibition of cell proliferation, as determined by a reduction of propidium iodide staining, by the pegylated double cysteine mutant AvPAL_C565SC503S in tumor cell lines derived from brain/CNS, colon, lung and prostate cancer is shown in FIG. 17A-D, respectively.

The AvPAL_C565SC503S displayed a selective anti-proliferative activity in this broad panel of solid tumor cell lines, and was particularly potent (i.e., $IC_{50}$ between 0.2 and 0.7 μg/mL) in tumor cell lines derived from lung, brain/CNS, colon, prostate and kidney. At least on tumor cell line derived from bladder, head and neck, breast, ovary and uterus were also sensitive to cell killing by AvPAL_C565SC503S. Several melanomas were also sensitive to cell killing by AvPAL_C565SC503S.

Example 15

Antitumor Activity of AvPAL Variants (Cysteine Mutants) in Nude Mice

Studies are performed to investigate the effect of a PEGylated form of an AvPAL polypeptide variant (e.g., with serine substitution of the cysteine residues at positions 503 and 565) on the proliferation of tumor cells grown in nude mice in vivo.

The pegylated AvPAL double cysteine mutant AvPAL_C565SC503S is prepared as described in EXAMPLE 7.

Subcutaneous xenografts of human tumor cells in immunodeficient nude or SCID mice have been successfully used as models for human cancers to test the in vivo efficacy of cancer therapeutic agents as well as targeted cancer therapeutic agents, such as antibodies and toxin conjugates (for review, see Kerbel, Cancer Biol. Ther. 2(4):Suppl. 1:S134-S139 (2003)).

The in vivo antitumor activity of the pegylated AvPAL double cysteine mutant AvPAL_C565SC503S can be tested alone or in combination with cancer therapeutic agents or targeted cancer therapeutic agents, or in combination with a phenylalanine-restricted diet, using xenografts of human tumor cells in nude mice.

To establish human tumor xenografts, nude mice are injected subcutaneously with about $5\times10^6$ human tumor cells in 0.2 mL PBS. The average tumor size increases over time. Human xenograft tumors are excised from the tumor bearing nude mice and tumor tissue blocks of approximately 30 $mm^3$ are prepared. Naive nude mice to be used for evaluating in vivo antitumor activity of pegylated AvPAL double cysteine mutant AvPAL_C565SC503S are each implanted subcutaneously with one tumor tissue block. Therapeutic treatment is initiated before tumor initiation or when the average tumor size within a group of nude mice is approximately 100-150 $mm^3$ (prevention model), and/or after the establishment of tumors when the average tumor size within a group of nude mice is above 500 $mm^3$ (treatment model).

In a first step, the dose of pegylated AvPAL double cysteine mutant AvPAL_C565SC503S that will lower plasma phenylalanine (Phe) levels to near zero is determined. Experiments are performed such as those described in Examples 7 to 9 and 14 in prior co-pending U.S. patent application Ser. No. 11/451,999 filed on Jun. 12, 2006, except nude mice rather than ENU2 mice are used. The PAL enzyme dose and the frequency of administration are determined in this initial step.

In a second step, the anti-tumor activity of pegylated AvPAL double cysteine mutant AvPAL_C565SC503S is assessed in various human tumor xenografts derived from patients or cell lines. Tumor models include different cancer types, for example and not for limitation, central nervous system (CNS), colon, lung, prostate, metastatic melanoma and renal cancer. Non-comprehensive lists of tumors and tumor cell lines that can be tested are provided in Tables 7 (hematological tumors) and 8 (solid tumors).

To assess the antitumor activity of pegylated AvPAL double cysteine mutant AvPAL_C565SC503S, nude mice bearing different human tumor xenografts subcutaneously are treated with AvPAL_C565SC503S given subcutaneously at, e.g., three different dose levels, ranging from about 5 to 500 mg/kg. This dose may result in a human dose of about 0.1 to 10 mg/kg. Antitumor activity is analyzed as tumor volume inhibition and/or absolute growth delay. The tolerability of the AvPAL_C565SC503S is also evaluated as mortality and/or body weight changes.

Each in vivo antitumor study consists of at least four groups, one vehicle control group and at least three prokaryotic PAL enzyme-treated groups. The group size will be at least 8 mice, resulting in a total of 32 mice receiving subcutaneous tumor implantations. Mice with similar sized tumors (100-150 $mm^3$) will be used for randomization (Day 0).

In the case of an antitumor effect, mice may be monitored for additional 2 weeks after termination of prokaryotic PAL enzyme treatment to detect a possible reinitiation of tumor growth. According to regulations for animal experiments, mice are sacrificed if the tumor diameters exceed 1.6 cm.

Tumor diameters are measured twice weekly together with body weight. Tumor volume is calculated according to the formula $a*b^2/2$ (where 'a' is the largest diameter of the tumor and 'b' is the perpendicular axis). Relative tumor volumes and body weights are calculated for each individual tumor based on the value on Day 0 (the first day of dosing). Treatment starts when the tumors have reached a volume of approximately 100-150 $mm^3$. Mice are sacrificed if the tumor volume exceeds 1600 $mm^3$, per regulations for animal studies.

Patient-derived tumors established in serial passage in nude mice can also be used as test tumors. Typically, these tumors retain important characteristics of the original patient tumor, including histology and drug sensitivity. For certain tumors, e.g., one CNS and both prostate cancers, cancer cell line-derived tumors are used.

Example 16

Exemplary Prokaryotic PAL Formulations

The following example provides guidance on the parameters to be used to formulate compositions comprising prokaryotic PAL or biologically active fragments, mutant, variants or analogs thereof, which are useful for treatment of neoplastic disease and cancer. Parameters to be used to formulate prokaryotic PAL compositions of the invention include, but are not limited to, buffering agents to maintain pH, isotonicity-adjusting agents, absence or presence of stabilizers, and absence or presence of other excipients, vehicles, diluents, and the like.

In EXAMPLE 11, the pegylated AvPAL double cysteine mutant AvPAL_C565SC503S was formulated at a concentration of about 12-20 mg/mL (about 0.2-0.33 mM). A preferred prokaryotic PAL variant is formulated at a concentration ranging from about 1 to 50 mg/mL (about 0.016 to 0.8 mM), preferably from about 5 to 20 mg/mL (about 0.08 to 0.33 mM), and more preferably from about 5 to 15 mg/mL (about 0.08 to 0.25 mM). A most preferred formulation of the prokaryotic PAL compositions of the invention has a PAL enzyme concentration of about 10+/−5 mg/mL (about 0.16+/−0.08 mM).

In EXAMPLE 11, the pegylated AvPAL double cysteine mutant AvPAL_C565SC503S was formulated in 10 mM Tris-HCl, 140 mM NaCl at pH 7.0, 7.5 and 8.0. A preferred buffering agent is Tris-HCl, or its equivalent, with a concentration ranging from 5 to 50 mM, preferably from 5 to 20 mM, and more preferably from 5 to 15 mM. A most preferred formulation of the prokaryotic PAL compositions of the invention has a Tris-HCl buffer concentration of about 10+/−5 mM.

A preferred pH of the pharmaceutical composition is about pH 6.0-8.5, preferably about pH 7.0-8.0, and more preferably about pH 7.0-7.6. A most preferred formulation of the prokaryotic PAL compositions of the invention has a pH of about pH 7.3+/−0.3.

A preferred isotonicity-adjusting agent is NaCl, or its equivalent, with a concentration ranging from about 100 to 200 mM, preferably from about 130 to 170 mM, and more preferably from about 130 to 150 mM. A most preferred formulation of the prokaryotic PAL compositions of the invention has a NaCl concentration of about 140+/−10 mM.

As shown in EXAMPLE 11, the pegylated AvPAL double cysteine mutant AvPAL_C565SC503 S was stabilized in the presence of phenylalanine (Phe), and certain of its structural analogs, including, for example, trans-cinnamic acid (t-CA) and benzoic acid; tyrosine (Tyr) had a minimal stabilizing effect on the PAL enzyme. A preferred stabilizer is Phe, or structural analog thereof, with a range for the stabilizer from about 0.1 to 20 moles of stabilizer per mole active site of prokaryotic PAL, preferably from about 0.5 to 10 moles of stabilizer per mole active site of prokaryotic PAL, and more preferably from about 1 to 10 moles of stabilizer per mole active site of prokaryotic PAL. A most preferred formulation of the prokaryotic PAL compositions of the invention has a stabilizer concentration of about 5+/−4 moles of stabilizer per mole active site of prokaryotic PAL.

The pegylated AvPAL double cysteine mutant AvPAL_C565SC503S was not significantly stabilized at pH<7 or pH>7.6, or in the presence of EDTA, aminoguanidine or Tween 80; the anti-oxidants ascorbic acid and methionine destabilized the PAL enzyme (EXAMPLE 11 and data not shown).

The prokaryotic PAL compositions of the invention are preferably made as liquid formulations, but may also be prepared as solid (e.g., lyophilized) formulations. In such case, excipients, e.g, bulking agents, such as mannitol and/or sucrose, may be added. In EXAMPLE 12, the pegylated AvPAL double cysteine mutant AvPAL_C565SC503S was formulated and lyophilized in 10 mM Tris-HCl, 140 mM NaCl at pH 7.5 in the absence of mannitol or sucrose, in the presence of 25 mg/mL mannitol, or in the presence of 20 mg/mL mannitol plus 5 mg/mL sucrose. A preferred lyophilized formulation comprises mannitol at a concentration from about 1 to 5% (w/v) or 10 to 50 mg/mL, preferably from about 2 to 4%, and more preferably from about 2 to 3%. Another preferred lyophilized formulation comprises mannitol and sucrose, with a concentration of mannitol from about 1 to 5% (w/v) or 10 to 50 mg/mL, preferably from about 1 to 3%, and more preferably from about 1.5 to 2.5%, and a concentration of sucrose from about 0.1 to 2% (w/v) or 0.1 to 2 mg/mL, preferably from about 0.2% to 1%, and more preferably from about 0.3% to 0.7%. A most preferred lyophilized formulation of the prokaryotic PAL compositions of the invention has a mannitol concentration of about 2.5+/−0.5% mannitol or 2.0+/−0.5% mannitol plus 0.5+/−0.2% sucrose.

Accordingly, a preferred formulation of the prokaryotic PAL compositions of the invention is shown in Table 9.

TABLE 9

Exemplary Formulations of Prokaryotic PAL Variants

| Ingredient Class | Ingredient Type | Concentration Range |
|---|---|---|
| Prokaryotic PAL Variant | Pegylated AvPAL_C565SC503S | 10 +/− 5 mg/mL (0.16 +/− 0.08 mM) |
| Buffering Agent | Tris-HCl | 10 mM +/− 5 mM, and pH 7.3 +/− 0.3 |
| Isotonicity-Adjusting Agent | NaCl | 140 mM +/− 10 mM |
| Stabilizer | Phe, t-CA, or Benzoic Acid | 5 +/− 4 moles of stabilizer per mole PAL active site |
| Other Excipients, Bulking Agents* | Mannitol +/− Sucrose | 2.5 +/− 0.5% (w/v) mannitol; 2.0 +/− 0.5% (w/v) mannitol + 0.5 +/− 0.2% (w/v) sucrose |

*For lyophilized prokaryotic PAL formulations

Example 17

Clinical Evaluation with Prokaryotic PAL Compositions for Treatment of Cancer The following example provides guidance on the parameters to be used for the clinical evaluation of compositions comprising prokaryotic PAL or biologically active fragments, mutant, variants or analogs thereof in the therapeutic methods of the present invention. As discussed herein throughout, prokaryotic PAL compositions will be used in the treatment of cancer. Clinical trials will be conducted which will provide an assessment of oral or subcutaneous doses of prokaryotic PAL for safety, pharmacokinetics, and initial response of both surrogate and defined clinical endpoints. The trial will be conducted for a minimum, but not necessarily limited to, 24 weeks to collect sufficient safety information for 100 evaluable patients. The initial dose for the trials will vary from about 0.001 to about 1.0 mg/kg/week. In the event that this dose does not produce a reduction in plasma phenylalanine (Phe) levels in a patient, e.g., a reduction from the normal range about 50 μM to about 70 μM to a range from below the level of detection to less than about 30 μM, preferably less than about 20 μM, and even more preferably less than about 10 μM, the dose should be increased as necessary, and maintained for an additional minimal period of, but necessarily limited to, 24 weeks to establish safety and to evaluate further efficacy.

Measurements of safety will include adverse events, allergic reactions, complete clinical chemistry panel (kidney and liver function), urinalysis, and CBC with differential. In addition, other parameters including the reduction in levels of blood Phe levels, neuropsychological and cognitive testing, and global assessments also will be monitored. The present example also contemplates the determination of pharmacokinetic parameters of the drug in the circulation, and general distribution and half-life of PAL in blood. It is anticipated that these measures will help relate dose to clinical response.

Methods

Cancer-free control patients and patients who have been diagnosed with a form of cancer will undergo a baseline a medical history and physical exam, neuropsychological and cognitive testing, a standard set of clinical laboratory tests (CBC, Panel 20, CH50, UA), levels of urinary pterins, dihydropteridine reductase (DHPR) levels, and a fasting blood (plasma) panel of serum amino acids. Baseline blood, serum or plasma Phe levels will be measured. The patient will be followed closely with weekly visits to the clinic. Patients will return to the clinic for a complete evaluation one week after completing the treatment period. Should dose escalation be required, the patients will follow the same schedule outlined above. Safety will be monitored throughout the trial.

Diagnosis and Inclusion/Exclusion Criteria

The patient may be male or female, with a documented diagnosis of a form of cancer. The study will include cancer patients who have previously undergone surgery, chemotherapy, radiation therapy and/or other anti-cancer therapy and are in remission (e.g., disease-free for at least 5 years). A patient will be excluded from this initial study if the patient has been diagnosed with a form of cancer, but has not undergone some form of anti-cancer therapy.

Prokaryotic PAL Safety

Prokaryotic PAL therapy will be determined to be safe if no significant acute or chronic drug reactions occur during the course of the study. The longer-term administration of the drug will be determined to be safe if no significant abnormalities are observed in the clinical examinations, clinical labs, or other appropriate studies.

Prokaryotic PAL Efficacy

Once prokaryotic PAL therapy has been determined to be safe and effective to reduce the plasma phenylalanine (Phe) levels in a patient, e.g., a reduction from the normal range about 50 μM to about 70 μM to a range from below the level of detection to less than about 30 μM, preferably less than about 20 μM, and even more preferably less than about 10 μM, the prokaryotic PAL compositions of the invention can be tested in cancer patients who have previously undergone surgery, chemotherapy, radiation therapy and/or other anti-cancer therapy and are in remission (e.g., disease-free for at least 5 years), as well as in patients who have been diagnosed with a form of cancer, but have not as yet undergone any form of anti-cancer therapy.

For cancer patients in remission, prokaryotic PAL is administered, alone or in combination with standard cancer therapy for the particular form of cancer, to determine whether patients given the PAL therapy remain in remission (i.e., disease-free) for a longer period of time than patients not given prokaryotic PAL compositions of the invention.

For cancer patients with an active form of cancer, prokaryotic PAL is administered, alone or in combination with standard cancer therapy for the particular form of cancer, to determine whether patients given the PAL therapy have a better response to the cancer therapy (e.g., remain disease-free longer, have longer survival time, or have lower tumor growth, tumor size or tumor burden) than patients not given prokaryotic PAL compositions of the invention.

Prokaryotic PAL therapy can be administered alone, or in combination with a cancer therapeutic agent or targeted cancer therapeutic agent, or with a protein-restricted diet (i.e., phenylalanine-free), or both.

Numerous modifications and variations in the invention as set forth in the above illustrative examples are expected to occur to those skilled in the art. Consequently only such limitations as appear in the appended claims should be placed on the invention.

What is claimed:

1. A method for treating a subject having cancer, comprising administering to the subject a therapeutically effective amount of a pharmaceutical composition comprising (a) an *Anabaena variabilis* phenylalanine ammonia-lyase (AvPAL) variant, wherein the cysteine residue at position 503 of said AvPAL variant has been substituted by a seine residue (SEQ ID NO:9), and wherein said AvPAL variant further comprises a polyethylene glycol, and (b) a pharmaceutically acceptable carrier.

2. A method for treating a subject having cancer, comprising administering to the subject a therapeutically effective amount of a pharmaceutical composition comprising (a) an AvPAL variant, wherein the cysteine residue at position 565 of said AvPAL variant has been substituted by a seine residue (SEQ ID NO:10), and wherein said AvPAL variant further comprises a polyethylene glycol, and (b) a pharmaceutically acceptable carrier.

3. A method for treating a subject having cancer, comprising administering to the subject a therapeutically effective amount of a pharmaceutical composition comprising (a) an AvPAL variant, wherein the cysteine residues at positions 503 and 565 of said AvPAL variant have been substituted by serine residues (SEQ ID NO:11), and wherein said AvPAL variant further comprises a polyethylene glycol, and (b) a pharmaceutically acceptable carrier.

4. The method of claim 3, wherein the ratio of the AvPAL variant to the polyethylene glycol is about 1:3.

5. The method of claim 3, wherein the effective amount decreases blood, serum or plasma phenylalanine concentration of the subject to a range from below the level of detection to between 20 μM and 60 μM.

6. The method of claim 3, wherein the pharmaceutically acceptable carrier comprises a stabilizer.

7. The method of claim 6, wherein the stabilizer is L-phenylalanine or structural analog thereof.

8. The method of claim 6, wherein the stabilizer is L-phenylalanine.

9. The method of claim 6, wherein the stabilizer is trans-cinnamic acid.

10. The method of claim 6, wherein the stabilizer is benzoic acid.

11. The method of claim 3, wherein the cancer is a lung cancer, brain cancer, central nervous system cancer, colon cancer, prostate cancer, renal cancer, head and neck cancer, ovarian cancer, uterine cancer, bladder cancer, breast cancer, pancreatic cancer, acute myeloid leukemia, acute lymphoblastic leukemia, myeloma, pediatric cancer or a resistant cancer.

12. The method of claim 3, wherein the cancer is metastatic melanoma.

13. The method of claim 3, wherein the proliferation and/or survival of cells derived from the cancer is sensitive to phenylalanine restriction or depletion.

14. The method of claim 3, further comprising administering a therapeutically effective amount of a pharmaceutical composition comprising a cancer therapeutic agent or a targeted cancer therapeutic agent.

15. The method of claim 3, further comprising administering to the subject a protein-restricted diet.

16. The method of claim 3, wherein the effective amount decreases blood, serum or plasma phenylalanine concentration of the subject to a range from below the level of detection to less than about 20 μM.

17. The method of claim 3, wherein the effective amount decreases blood, serum or plasma phenylalanine concentration of the subject to a range from below the level of detection to less than about 10 μM.

18. The method of claim 3, wherein the subject is a human.

19. A method for decreasing blood, serum or plasma phenylalanine concentration of a subject having cancer, comprising administering to the subject a therapeutically effective amount of a pharmaceutical composition comprising (a) an AvPAL variant, wherein the cysteine residues at positions 503 and 565 of said AvPAL variant have been substituted by serine residues (SEQ ID NO:11), and wherein said AvPAL variant further comprises a polyethylene glycol, and (b) a pharmaceutically acceptable carrier.

20. The method of claim 19, wherein the ratio of the AvPAL variant to the polyethylene glycol is about 1:3.

21. The method of claim 19, wherein the effective amount decreases blood, serum or plasma phenylalanine concentration of the subject to a range from below the level of detection to between 20 μM and 60 μM.

22. The method of claim 19, wherein the pharmaceutically acceptable carrier comprises a stabilizer.

23. The method of claim 22, wherein the stabilizer is L-phenylalanine or structural analog thereof.

24. The method of claim 22, wherein the stabilizer is L-phenylalanine.

25. The method of claim 22, wherein the stabilizer is trans-cinnamic acid.

26. The method of claim 22, wherein the stabilizer is benzoic acid.

* * * * *

SEQUENCE LISTING

```
<160> NUMBER OF SEQ ID NOS: 33

<210> SEQ ID NO 1
<211> LENGTH: 1710
<212> TYPE: DNA
<213> ORGANISM: Nostoc punctiforme

<400> SEQUENCE: 1

atgaatataa catctctaca acagaacata acgcgttctt ggcaaatacc tttcactaat     60

agttcagatt caatcgtaac tgtaggcgat cgcaatctga caatcgacga ggttgtaaat    120

gttgctcgtc atggaacaca ggtgcgctta actgataatg cagatgtcat tcggggtgtt    180

caagcatctt gtgattacat taacaatgca gtcgaaacag cacagccaat ttacggggtg    240

acatctggct ttggcggtat ggcagatgtt gtcatctctc gcgaacaagc agcggaactt    300

cagactaatt taatttggtt tctgaaatcc ggcgcaggaa acaaattatc gttagcagac    360

gtgcgtgcag ctatgctctt acgtgcaaat tcacatttgt atggtgcgtc tggtatacga    420

ctcgaactta ttcagcggat tgaaactttc ctcaacgctg gcgtgacacc ccatgtctat    480

gagtttggct ctatcggtgc tagcggcgat ttggtgccat tatcctacat tactggggca    540

ctaatcggtc tagatcctag ctttacagtt gacttcgacg gtaaagaaat ggatgccgtt    600

acagccttgt ctcgtttggg tttgccaaag ttgcaattgc aaccgaaaga aggtttagca    660

atgatgaatg gcacctcagt catgacaggt attgcagcta actgtgtgta cgatgcgaaa    720

gttttgctcg ctctgacaat gggtgtacac gccttagcca tccaaggttt atacggaacg    780

aatcaatctt tccacccgtt tattcatcag tgcaagccac atcccggtca actatggaca    840

gcagatcaaa tgttttctct gctgaaagat tcatctttag ttcgtgaaga gttggatggt    900

aaacacgaat accgtggtaa agatctgata caggatcgtt attctctccg ctgtctggca    960

cagttcatag ggccaatcgt tgatggggta tcagagatta ccaagcaaat cgaggtagaa   1020

atgaactcag tcaccgataa cccattgatt gatgtcgaga accaagttag ttatcacggc   1080

ggcaattttc tcggacagta tgtgggtgtg acaatggatc gcctacgtta ttacataggg   1140

ctattggcca aacacatcga tgtgcagatt gcacttcttg tctcgccaga gtttagcaac   1200

ggcttaccac cctctttagt tggtaatagc gatcgcaaag ttaatatggg actcaaaggt   1260

ttgcaaatca gtggaaactc gattatgcca ctgttgagct tctatggaaa ttccctagcc   1320

gatcgctttc ctacccacgc cgagcaattt aatcaaaata ttaacagcca aggctatatt   1380

tccgcaaatt tgacacgtcg ttccgtagac atatttcaga attatatggc gatcgcgttg   1440

atgtttggag ttcaagctgt tgacctccgc acatataaga tgaaaggtca ttatgatgca   1500

cgtacatgcc tctcacccaa tactgtgcag ttatacacag cagtctgcga ggtagttgga   1560

aagccactaa cgtctgtgcg tccatacatt tggaacgaca acgagcaatg tttagatgag   1620

catattgccc ggatttcagc tgatatcgct ggtggtggtt taattgtgca agcagttgag   1680

catatttttt cgagcttaaa gtcaacgtaa                                     1710

<210> SEQ ID NO 2
```

-continued

<211> LENGTH: 569
<212> TYPE: PRT
<213> ORGANISM: Nostoc punctiforme

<400> SEQUENCE: 2

```
Met Asn Ile Thr Ser Leu Gln Gln Asn Ile Thr Arg Ser Trp Gln Ile
1               5                   10                  15

Pro Phe Thr Asn Ser Ser Asp Ser Ile Val Thr Val Gly Asp Arg Asn
            20                  25                  30

Leu Thr Ile Asp Glu Val Val Asn Val Ala Arg His Gly Thr Gln Val
        35                  40                  45

Arg Leu Thr Asp Asn Ala Asp Val Ile Arg Gly Val Gln Ala Ser Cys
    50                  55                  60

Asp Tyr Ile Asn Asn Ala Val Glu Thr Ala Gln Pro Ile Tyr Gly Val
65                  70                  75                  80

Thr Ser Gly Phe Gly Gly Met Ala Asp Val Val Ile Ser Arg Glu Gln
                85                  90                  95

Ala Ala Glu Leu Gln Thr Asn Leu Ile Trp Phe Leu Lys Ser Gly Ala
            100                 105                 110

Gly Asn Lys Leu Ser Leu Ala Asp Val Arg Ala Ala Met Leu Leu Arg
        115                 120                 125

Ala Asn Ser His Leu Tyr Gly Ala Ser Gly Ile Arg Leu Glu Leu Ile
    130                 135                 140

Gln Arg Ile Glu Thr Phe Leu Asn Ala Gly Val Thr Pro His Val Tyr
145                 150                 155                 160

Glu Phe Gly Ser Ile Gly Ala Ser Gly Asp Leu Val Pro Leu Ser Tyr
                165                 170                 175

Ile Thr Gly Ala Leu Ile Gly Leu Asp Pro Ser Phe Thr Val Asp Phe
            180                 185                 190

Asp Gly Lys Glu Met Asp Ala Val Thr Ala Leu Ser Arg Leu Gly Leu
        195                 200                 205

Pro Lys Leu Gln Leu Gln Pro Lys Glu Gly Leu Ala Met Met Asn Gly
    210                 215                 220

Thr Ser Val Met Thr Gly Ile Ala Ala Asn Cys Val Tyr Asp Ala Lys
225                 230                 235                 240

Val Leu Leu Ala Leu Thr Met Gly Val His Ala Leu Ala Ile Gln Gly
                245                 250                 255

Leu Tyr Gly Thr Asn Gln Ser Phe His Pro Phe Ile His Gln Cys Lys
            260                 265                 270

Pro His Pro Gly Gln Leu Trp Thr Ala Asp Gln Met Phe Ser Leu Leu
        275                 280                 285

Lys Asp Ser Ser Leu Val Arg Glu Glu Leu Asp Gly Lys His Glu Tyr
    290                 295                 300

Arg Gly Lys Asp Leu Ile Gln Asp Arg Tyr Ser Leu Arg Cys Leu Ala
305                 310                 315                 320

Gln Phe Ile Gly Pro Ile Val Asp Gly Val Ser Glu Ile Thr Lys Gln
                325                 330                 335

Ile Glu Val Glu Met Asn Ser Val Thr Asp Asn Pro Leu Ile Asp Val
            340                 345                 350

Glu Asn Gln Val Ser Tyr His Gly Gly Asn Phe Leu Gly Gln Tyr Val
        355                 360                 365

Gly Val Thr Met Asp Arg Leu Arg Tyr Tyr Ile Gly Leu Leu Ala Lys
    370                 375                 380

His Ile Asp Val Gln Ile Ala Leu Leu Val Ser Pro Glu Phe Ser Asn
```

-continued 385 390 395 400

Gly Leu Pro Pro Ser Leu Val Gly Asn Ser Asp Arg Lys Val Asn Met
405 410 415

Gly Leu Lys Gly Leu Gln Ile Ser Gly Asn Ser Ile Met Pro Leu Leu
420 425 430

Ser Phe Tyr Gly Asn Ser Leu Ala Asp Arg Phe Pro Thr His Ala Glu
435 440 445

Gln Phe Asn Gln Asn Ile Asn Ser Gln Gly Tyr Ile Ser Ala Asn Leu
450 455 460

Thr Arg Arg Ser Val Asp Ile Phe Gln Asn Tyr Met Ala Ile Ala Leu
465 470 475 480

Met Phe Gly Val Gln Ala Val Asp Leu Arg Thr Tyr Lys Met Lys Gly
485 490 495

His Tyr Asp Ala Arg Thr Cys Leu Ser Pro Asn Thr Val Gln Leu Tyr
500 505 510

Thr Ala Val Cys Glu Val Val Gly Lys Pro Leu Thr Ser Val Arg Pro
515 520 525

Tyr Ile Trp Asn Asp Asn Glu Gln Cys Leu Asp Glu His Ile Ala Arg
530 535 540

Ile Ser Ala Asp Ile Ala Gly Gly Gly Leu Ile Val Gln Ala Val Glu
545 550 555 560

His Ile Phe Ser Ser Leu Lys Ser Thr
565

<210> SEQ ID NO 3
<211> LENGTH: 1704
<212> TYPE: DNA
<213> ORGANISM: Anabaena variabilis

<400> SEQUENCE: 3
atgaagacac tatctcaagc acaaagcaaa acctcatctc aacaattttc ttttactgga 60
aattcttctg ccaatgtaat tattggtaat cagaaactca caatcaatga tgttgcaagg 120
gtagcgcgta atggcacctt agtgtcttta accaataaca ctgatatttt gcagggtatt 180
caggcatctt gtgattacat taataatgct gttgaatctg gggaaccaat ttatggagtg 240
acatctggtt ttggcggtat ggccaatgtt gccatatccc gtgaacaagc atctgaactc 300
caaaccaact tagtttggtt cctgaaaaca ggtgcaggga acaaattacc cttggcggat 360
gtgcgcgcag ctatgctctt gcgtgcaaac tctcatatgc gcggtgcatc tggcatcaga 420
ttagaactta tcaagcgtat ggagattttc cttaacgctg gtgtcacacc atatgtgtat 480
gagtttggtt caattggtgc aagtggtgat ttagtgccac tatcctacat tactggttca 540
ctgataggct tagatcccag ttttaaggtt gacttcaacg gtaaagaaat ggatgcgcca 600
acagctctac gtcaactgaa tttgtcaccc ttgacattgt tgccgaagga aggcttggcg 660
atgatgaacg gcacttcagt catgacaggt attgcagcaa actgcgtcta cgatactcaa 720
attttaactg cgatcgctat gggcgttcac gctctagata tccaagcttt aaacggaacc 780
aatcaatcat tccatccatt tatccataat tccaaaccac atcctggtca attatgggca 840
gcagatcaga tgatttcttt gttagccaat tcccagttag ttcgtgatga gttagatggt 900
aaacacgatt atcgtgatca cgagttgatt caagatcgtt actcactccg atgccttccc 960
cagtatttgg ggccaatcgt tgatggaatt tcccagattg ccaaacaaat tgaaatcgaa 1020
atcaactcag tcaccgataa cccactaatt gatgttgata accaagctag ctatcatgga 1080

-continued

```
ggaaatttcc tcggacagta cgtgggtatg ggaatggatc acctgcgtta ctatattggg   1140

ttattggcta aacacctaga tgtgcagatt gccctcctcg cctcaccaga gtttagcaat   1200

ggactaccac catctttatt aggcaaccga gaacgtaaag tcaatatggg actcaaaggt   1260

ctgcaaatat gcggtaactc aattatgcca ctgttgacct tctatggaaa ttccatcgcc   1320

gatcgctttc ctacccatgc agaacaattt aatcagaaca tcaacagtca aggatacact   1380

tcagcgactc tagcccgccg ttctgtggat atcttccaga attatgtggc gatcgctctg   1440

atgtttggag tccaagctgt tgacctccgc acatataaaa agactggtca ttacgatgca   1500

cgcgcctgtc tatcacctgc aactgagcgc ttatattcag cagtccgcca cgtagttgga   1560

caaaaaccaa cttcagatcg cccatatatt tggaatgata atgagcaagg actggatgag   1620

catattgccc ggatttctgc tgatatcgct gctggtggtg tgattgtgca agcagttcaa   1680

gatatcttac cctgcttgca ttaa                                          1704


<210> SEQ ID NO 4
<211> LENGTH: 567
<212> TYPE: PRT
<213> ORGANISM: Anabaena variabilis

<400> SEQUENCE: 4

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
```

-continued

```
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565


<210> SEQ ID NO 5
<211> LENGTH: 523
<212> TYPE: PRT
<213> ORGANISM: Streptomyces maritimus

<400> SEQUENCE: 5

Met Thr Phe Val Ile Glu Leu Asp Met Asn Val Thr Leu Asp Gln Leu
1               5                   10                  15

Glu Asp Ala Ala Arg Gln Arg Thr Pro Val Glu Leu Ser Ala Pro Val
            20                  25                  30

Arg Ser Arg Val Arg Ala Ser Arg Asp Val Leu Val Lys Phe Val Gln
        35                  40                  45

Asp Glu Arg Val Ile Tyr Gly Val Asn Thr Ser Met Gly Gly Phe Val
    50                  55                  60
```

-continued

```
Asp His Leu Val Pro Val Ser Gln Ala Arg Gln Leu Gln Glu Asn Leu
65                  70                  75                  80

Ile Asn Ala Val Ala Thr Asn Val Gly Ala Tyr Leu Asp Asp Thr Thr
                85                  90                  95

Ala Arg Thr Ile Met Leu Ser Arg Ile Val Ser Leu Ala Arg Gly Asn
            100                 105                 110

Ser Ala Ile Thr Pro Ala Asn Leu Asp Lys Leu Val Ala Val Leu Asn
        115                 120                 125

Ala Gly Ile Val Pro Cys Ile Pro Glu Lys Gly Ser Leu Gly Thr Ser
    130                 135                 140

Gly Asp Leu Gly Pro Leu Ala Ala Ile Ala Leu Val Cys Ala Gly Gln
145                 150                 155                 160

Trp Lys Ala Arg Tyr Asn Gly Gln Ile Met Pro Gly Arg Gln Ala Leu
                165                 170                 175

Ser Glu Ala Gly Val Glu Pro Met Glu Leu Ser Tyr Lys Asp Gly Leu
            180                 185                 190

Ala Leu Ile Asn Gly Thr Ser Gly Met Val Gly Leu Gly Thr Met Val
        195                 200                 205

Leu Gln Ala Ala Arg Arg Leu Val Asp Arg Tyr Leu Gln Val Ser Ala
    210                 215                 220

Leu Ser Val Glu Gly Leu Ala Gly Met Thr Lys Pro Phe Asp Pro Arg
225                 230                 235                 240

Val His Gly Val Lys Pro His Arg Gly Gln Arg Gln Val Ala Ser Arg
                245                 250                 255

Leu Trp Glu Gly Leu Ala Asp Ser His Leu Ala Val Asn Glu Leu Asp
            260                 265                 270

Thr Glu Gln Thr Leu Ala Gly Glu Met Gly Thr Val Ala Lys Ala Gly
        275                 280                 285

Ser Leu Ala Ile Glu Asp Ala Tyr Ser Ile Arg Cys Thr Pro Gln Ile
    290                 295                 300

Leu Gly Pro Val Val Asp Val Leu Asp Arg Ile Gly Ala Thr Leu Gln
305                 310                 315                 320

Asp Glu Leu Asn Ser Ser Asn Asp Asn Pro Ile Val Leu Pro Glu Glu
                325                 330                 335

Ala Glu Val Phe His Asn Gly His Phe His Gly Gln Tyr Val Ala Met
            340                 345                 350

Ala Met Asp His Leu Asn Met Ala Leu Ala Thr Val Thr Asn Leu Ala
        355                 360                 365

Asn Arg Arg Val Asp Arg Phe Leu Asp Lys Ser Asn Ser Asn Gly Leu
    370                 375                 380

Pro Ala Phe Leu Cys Arg Glu Asp Pro Gly Leu Arg Leu Gly Leu Met
385                 390                 395                 400

Gly Gly Gln Phe Met Thr Ala Ser Ile Thr Ala Glu Thr Arg Thr Leu
                405                 410                 415

Thr Ile Pro Met Ser Val Gln Ser Leu Thr Ser Thr Ala Asp Phe Gln
            420                 425                 430

Asp Ile Val Ser Phe Gly Phe Val Ala Ala Arg Arg Ala Arg Glu Val
        435                 440                 445

Leu Thr Asn Ala Ala Tyr Val Val Ala Phe Glu Leu Leu Cys Ala Cys
    450                 455                 460

Gln Ala Val Asp Ile Arg Gly Ala Asp Lys Leu Ser Ser Phe Thr Arg
465                 470                 475                 480

Pro Leu Tyr Glu Arg Thr Arg Lys Ile Val Pro Phe Phe Asp Arg Asp
```

-continued

```
                485                 490                 495

Glu Thr Ile Thr Asp Tyr Val Glu Lys Leu Ala Ala Asp Leu Ile Ala
            500                 505                 510

Gly Glu Pro Val Asp Ala Ala Val Ala Ala His
        515                 520


<210> SEQ ID NO 6
<211> LENGTH: 510
<212> TYPE: PRT
<213> ORGANISM: Pseudomonas putida

<400> SEQUENCE: 6

Met Thr Glu Leu Thr Leu Lys Pro Gly Thr Leu Thr Leu Ala Gln Leu
1               5                   10                  15

Arg Ala Ile His Ala Ala Pro Val Arg Leu Gln Leu Asp Ala Ser Ala
            20                  25                  30

Ala Pro Ala Ile Asp Ala Ser Val Ala Cys Val Glu Gln Ile Ile Ala
        35                  40                  45

Glu Asp Arg Thr Ala Tyr Gly Ile Asn Thr Gly Phe Gly Leu Leu Ala
    50                  55                  60

Ser Thr Arg Ile Ala Ser His Asp Leu Glu Asn Leu Gln Arg Ser Leu
65                  70                  75                  80

Val Leu Ser His Ala Ala Gly Ile Gly Ala Pro Leu Asp Asp Asp Leu
                85                  90                  95

Val Arg Leu Ile Met Val Leu Lys Ile Asn Ser Leu Ser Arg Gly Phe
            100                 105                 110

Ser Gly Ile Arg Arg Lys Val Ile Asp Ala Leu Ile Ala Leu Val Asn
        115                 120                 125

Ala Glu Val Tyr Pro His Ile Pro Leu Lys Gly Ser Val Gly Ala Ser
    130                 135                 140

Gly Asp Leu Ala Pro Leu Ala Thr Met Ser Leu Val Leu Leu Gly Glu
145                 150                 155                 160

Gly Lys Ala Arg Tyr Lys Gly Gln Trp Leu Ser Ala Thr Glu Ala Leu
                165                 170                 175

Ala Val Ala Gly Leu Glu Pro Leu Thr Leu Ala Ala Lys Glu Gly Leu
            180                 185                 190

Ala Leu Leu Asn Gly Thr Gln Ala Ser Thr Ala Tyr Ala Leu Arg Gly
        195                 200                 205

Leu Phe Tyr Ala Glu Asp Leu Tyr Ala Ala Ala Ile Ala Cys Gly Gly
    210                 215                 220

Leu Ser Val Glu Ala Val Leu Gly Ser Arg Ser Pro Phe Asp Ala Arg
225                 230                 235                 240

Ile His Glu Ala Arg Gly Gln Arg Gly Gln Ile Asp Thr Ala Ala Cys
                245                 250                 255

Phe Arg Asp Leu Leu Gly Asp Ser Ser Glu Val Ser Leu Ser His Lys
            260                 265                 270

Asn Cys Asp Lys Val Gln Asp Pro Tyr Ser Leu Arg Cys Gln Pro Gln
        275                 280                 285

Val Met Gly Ala Cys Leu Thr Gln Leu Arg Gln Ala Ala Glu Val Leu
    290                 295                 300

Gly Ile Glu Ala Asn Ala Val Ser Asp Asn Pro Leu Val Phe Ala Ala
305                 310                 315                 320

Glu Gly Asp Val Ile Ser Gly Gly Asn Phe His Ala Glu Pro Val Ala
                325                 330                 335
```

-continued

```
Met Ala Ala Asp Asn Leu Ala Leu Ala Ile Ala Glu Ile Gly Ser Leu
            340                 345                 350

Ser Glu Arg Arg Ile Ser Leu Met Met Asp Lys His Met Ser Gln Leu
        355                 360                 365

Pro Pro Phe Leu Val Glu Asn Gly Gly Val Asn Ser Gly Phe Met Ile
    370                 375                 380

Ala Gln Val Thr Ala Ala Ala Leu Ala Ser Glu Asn Lys Ala Leu Ser
385                 390                 395                 400

His Pro His Ser Val Asp Ser Leu Pro Thr Ser Ala Asn Gln Glu Asp
                405                 410                 415

His Val Ser Met Ala Pro Ala Ala Gly Lys Arg Leu Trp Glu Met Ala
            420                 425                 430

Glu Asn Thr Arg Gly Val Pro Ala Ile Glu Trp Leu Gly Ala Cys Gln
        435                 440                 445

Gly Leu Asp Leu Arg Lys Gly Leu Lys Thr Ser Ala Lys Leu Glu Lys
    450                 455                 460

Ala Arg Gln Ala Leu Arg Ser Glu Val Ala His Tyr Asp Arg Asp Arg
465                 470                 475                 480

Phe Phe Ala Pro Asp Ile Glu Lys Ala Val Glu Leu Leu Ala Lys Gly
                485                 490                 495

Ser Leu Thr Gly Leu Leu Pro Ala Gly Val Leu Pro Ser Leu
            500                 505                 510


<210> SEQ ID NO 7
<211> LENGTH: 567
<212> TYPE: PRT
<213> ORGANISM: Artificial
<220> FEATURE:
<223> OTHER INFORMATION: Cysteine to serine substitution at position 64
      in Anabaena variabilis PAL

<400> SEQUENCE: 7

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Ser
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190
```

-continued

```
Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565
```

```
<210> SEQ ID NO 8
<211> LENGTH: 567
<212> TYPE: PRT
<213> ORGANISM: Artificial
<220> FEATURE:
```

-continued

<223> OTHER INFORMATION: Cysteine to serine substitution at position 318
in Anabaena variabilis PAL

<400> SEQUENCE: 8

```
Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Ser Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400
```

-continued

```
Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565


<210> SEQ ID NO 9
<211> LENGTH: 567
<212> TYPE: PRT
<213> ORGANISM: Artificial
<220> FEATURE:
<223> OTHER INFORMATION: Cysteine to serine substitution at position 503
      in Anabaena variabilis PAL

<400> SEQUENCE: 9

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
```

-continued

```
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Ser Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Cys Leu His
                565
```

<210> SEQ ID NO 10
<211> LENGTH: 567
<212> TYPE: PRT
<213> ORGANISM: Artificial

-continued

```
<220> FEATURE:
<223> OTHER INFORMATION: Cysteine to serine substition at position 565
      in Anabaena variabilis PAL

<400> SEQUENCE: 10

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175

Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
```

-continued

```
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Cys Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Ser Leu His
                565


<210> SEQ ID NO 11
<211> LENGTH: 567
<212> TYPE: PRT
<213> ORGANISM: Artificial
<220> FEATURE:
<223> OTHER INFORMATION: Cysteine to serine substitutions at positions
      565 and 503 in Anabaena variabilis PAL

<400> SEQUENCE: 11

Met Lys Thr Leu Ser Gln Ala Gln Ser Lys Thr Ser Ser Gln Gln Phe
1               5                   10                  15

Ser Phe Thr Gly Asn Ser Ser Ala Asn Val Ile Ile Gly Asn Gln Lys
            20                  25                  30

Leu Thr Ile Asn Asp Val Ala Arg Val Ala Arg Asn Gly Thr Leu Val
        35                  40                  45

Ser Leu Thr Asn Asn Thr Asp Ile Leu Gln Gly Ile Gln Ala Ser Cys
    50                  55                  60

Asp Tyr Ile Asn Asn Ala Val Glu Ser Gly Glu Pro Ile Tyr Gly Val
65                  70                  75                  80

Thr Ser Gly Phe Gly Gly Met Ala Asn Val Ala Ile Ser Arg Glu Gln
                85                  90                  95

Ala Ser Glu Leu Gln Thr Asn Leu Val Trp Phe Leu Lys Thr Gly Ala
            100                 105                 110

Gly Asn Lys Leu Pro Leu Ala Asp Val Arg Ala Ala Met Leu Leu Arg
        115                 120                 125

Ala Asn Ser His Met Arg Gly Ala Ser Gly Ile Arg Leu Glu Leu Ile
    130                 135                 140

Lys Arg Met Glu Ile Phe Leu Asn Ala Gly Val Thr Pro Tyr Val Tyr
145                 150                 155                 160

Glu Phe Gly Ser Ile Gly Ala Ser Gly Asp Leu Val Pro Leu Ser Tyr
                165                 170                 175
```

-continued

```
Ile Thr Gly Ser Leu Ile Gly Leu Asp Pro Ser Phe Lys Val Asp Phe
            180                 185                 190

Asn Gly Lys Glu Met Asp Ala Pro Thr Ala Leu Arg Gln Leu Asn Leu
        195                 200                 205

Ser Pro Leu Thr Leu Leu Pro Lys Glu Gly Leu Ala Met Met Asn Gly
    210                 215                 220

Thr Ser Val Met Thr Gly Ile Ala Ala Asn Cys Val Tyr Asp Thr Gln
225                 230                 235                 240

Ile Leu Thr Ala Ile Ala Met Gly Val His Ala Leu Asp Ile Gln Ala
                245                 250                 255

Leu Asn Gly Thr Asn Gln Ser Phe His Pro Phe Ile His Asn Ser Lys
            260                 265                 270

Pro His Pro Gly Gln Leu Trp Ala Ala Asp Gln Met Ile Ser Leu Leu
        275                 280                 285

Ala Asn Ser Gln Leu Val Arg Asp Glu Leu Asp Gly Lys His Asp Tyr
    290                 295                 300

Arg Asp His Glu Leu Ile Gln Asp Arg Tyr Ser Leu Arg Cys Leu Pro
305                 310                 315                 320

Gln Tyr Leu Gly Pro Ile Val Asp Gly Ile Ser Gln Ile Ala Lys Gln
                325                 330                 335

Ile Glu Ile Glu Ile Asn Ser Val Thr Asp Asn Pro Leu Ile Asp Val
            340                 345                 350

Asp Asn Gln Ala Ser Tyr His Gly Gly Asn Phe Leu Gly Gln Tyr Val
        355                 360                 365

Gly Met Gly Met Asp His Leu Arg Tyr Tyr Ile Gly Leu Leu Ala Lys
    370                 375                 380

His Leu Asp Val Gln Ile Ala Leu Leu Ala Ser Pro Glu Phe Ser Asn
385                 390                 395                 400

Gly Leu Pro Pro Ser Leu Leu Gly Asn Arg Glu Arg Lys Val Asn Met
                405                 410                 415

Gly Leu Lys Gly Leu Gln Ile Cys Gly Asn Ser Ile Met Pro Leu Leu
            420                 425                 430

Thr Phe Tyr Gly Asn Ser Ile Ala Asp Arg Phe Pro Thr His Ala Glu
        435                 440                 445

Gln Phe Asn Gln Asn Ile Asn Ser Gln Gly Tyr Thr Ser Ala Thr Leu
    450                 455                 460

Ala Arg Arg Ser Val Asp Ile Phe Gln Asn Tyr Val Ala Ile Ala Leu
465                 470                 475                 480

Met Phe Gly Val Gln Ala Val Asp Leu Arg Thr Tyr Lys Lys Thr Gly
                485                 490                 495

His Tyr Asp Ala Arg Ala Ser Leu Ser Pro Ala Thr Glu Arg Leu Tyr
            500                 505                 510

Ser Ala Val Arg His Val Val Gly Gln Lys Pro Thr Ser Asp Arg Pro
        515                 520                 525

Tyr Ile Trp Asn Asp Asn Glu Gln Gly Leu Asp Glu His Ile Ala Arg
    530                 535                 540

Ile Ser Ala Asp Ile Ala Ala Gly Gly Val Ile Val Gln Ala Val Gln
545                 550                 555                 560

Asp Ile Leu Pro Ser Leu His
                565


<210> SEQ ID NO 12
<211> LENGTH: 38
<212> TYPE: DNA
```

-continued

```
<213> ORGANISM: Artificial
<220> FEATURE:
<223> OTHER INFORMATION: Nostoc punctiforme PAL primer 1 (forward)

<400> SEQUENCE: 12

cactgtcata tgaatataac atctctacaa cagaacat                              38


<210> SEQ ID NO 13
<211> LENGTH: 45
<212> TYPE: DNA
<213> ORGANISM: Artificial
<220> FEATURE:
<223> OTHER INFORMATION: Nostoc punctiforme PAL primer 2 (reverse)

<400> SEQUENCE: 13

gacagtggcg gccgctcacg ttgactttaa gctcgaaaaa atatg                      45


<210> SEQ ID NO 14
<211> LENGTH: 38
<212> TYPE: DNA
<213> ORGANISM: Artificial
<220> FEATURE:
<223> OTHER INFORMATION: Anabaena variabilis PAL primer 1 (forward,
      N-terminal fragment)

<400> SEQUENCE: 14

cactgtgcta gcatgaagac actatctcaa gcacaaag                              38


<210> SEQ ID NO 15
<211> LENGTH: 49
<212> TYPE: DNA
<213> ORGANISM: Artificial
<220> FEATURE:
<223> OTHER INFORMATION: Anabaena variabilis PAL primer 2 (reverse,
      N-terminal fragment)

<400> SEQUENCE: 15

ggaaatttcc tccatgatag ctggcttggt tatcaacatc aattagtgg                  49


<210> SEQ ID NO 16
<211> LENGTH: 49
<212> TYPE: DNA
<213> ORGANISM: Artificial
<220> FEATURE:
<223> OTHER INFORMATION: Anabaena variabilis PAL primer 3 (forward,
      C-terminal fragment)

<400> SEQUENCE: 16

ccactaattg atgttgataa ccaagccagc tatcatggag gaaatttcc                  49


<210> SEQ ID NO 17
<211> LENGTH: 41
<212> TYPE: DNA
<213> ORGANISM: Artificial
<220> FEATURE:
<223> OTHER INFORMATION: Anabaena variabilis PAL primer 4 (reverse,
      C-terminal fragment)

<400> SEQUENCE: 17

cactgtgcgg ccgcttaatg caagcagggt aagatatctt g                          41


<210> SEQ ID NO 18
<211> LENGTH: 35
<212> TYPE: DNA
<213> ORGANISM: Artificial
<220> FEATURE:
<223> OTHER INFORMATION: Anabaena variabilis PAL forward primer
```

-continued

<400> SEQUENCE: 18
cactgtcata tgaagacact atctcaagca caaag 35

<210> SEQ ID NO 19
<211> LENGTH: 36
<212> TYPE: DNA
<213> ORGANISM: Artificial
<220> FEATURE:
<223> OTHER INFORMATION: Anabaena variabilis PAL reverse primer

<400> SEQUENCE: 19
cactgtctcg agatgcaagc agggtaagat atcttg 36

<210> SEQ ID NO 20
<211> LENGTH: 38
<212> TYPE: DNA
<213> ORGANISM: Artificial
<220> FEATURE:
<223> OTHER INFORMATION: Anabaena variabilis PAL primer to create 5' NheI site and delete internal NheI site (forward, N-terminal)

<400> SEQUENCE: 20
cactgtgcta gcatgaagac actatctcaa gcacaaag 38

<210> SEQ ID NO 21
<211> LENGTH: 49
<212> TYPE: DNA
<213> ORGANISM: Artificial
<220> FEATURE:
<223> OTHER INFORMATION: Anabaena variabilis PAL primer to create 5' NheI site and delete internal NheI site (reverse, N-terminal )

<400> SEQUENCE: 21
ggaaatttcc tccatgatag ctggcttggt tatcaacatc aattagtgg 49

<210> SEQ ID NO 22
<211> LENGTH: 49
<212> TYPE: DNA
<213> ORGANISM: Artificial
<220> FEATURE:
<223> OTHER INFORMATION: Anabaena variabilis PAL primer to create 5' NheI site and delete internal NheI site (forward, C-terminal fragment)

<400> SEQUENCE: 22
ccactaattg atgttgataa ccaagccagc tatcatggag gaaatttcc 49

<210> SEQ ID NO 23
<211> LENGTH: 41
<212> TYPE: DNA
<213> ORGANISM: Artificial
<220> FEATURE:
<223> OTHER INFORMATION: Anabaena variabilis PAL primer to create 5' NheI site and delete internal NheI site (reverse, C-terminal fragment)

<400> SEQUENCE: 23
acagtggcgg ccgcttaatg caagcagggt aagatatctt g 41

<210> SEQ ID NO 24
<211> LENGTH: 38
<212> TYPE: DNA
<213> ORGANISM: Artificial
<220> FEATURE:
<223> OTHER INFORMATION: Anabaena variabilis PAL primer to create 5' NheI site and 3' SmaI site (forward)

-continued

<400> SEQUENCE: 24
cactgtgaat tcatgaagac actatctcaa gcacaaag 38

<210> SEQ ID NO 25
<211> LENGTH: 37
<212> TYPE: DNA
<213> ORGANISM: Artificial
<220> FEATURE:
<223> OTHER INFORMATION: Anabaena variabilis PAL primer to create 5' NheI site and 3' SmaI site (reverse)

<400> SEQUENCE: 25
cactgtcccg ggttaatgca agcagggtaa gatatct 37

<210> SEQ ID NO 26
<211> LENGTH: 41
<212> TYPE: DNA
<213> ORGANISM: Artificial
<220> FEATURE:
<223> OTHER INFORMATION: Anabaena variabilis PAL primer to create cysteine to serine substitution at position 503 (forward)

<400> SEQUENCE: 26
gtcattacga tgcacgcgcc tctctatcac ctgcaactga g 41

<210> SEQ ID NO 27
<211> LENGTH: 41
<212> TYPE: DNA
<213> ORGANISM: Artificial
<220> FEATURE:
<223> OTHER INFORMATION: Anabaena variabilis PAL primer to create cysteine to serine substitution at position 503 (reverse)

<400> SEQUENCE: 27
ctcagttgca ggtgatagag aggcgcgtgc atcgtaatga c 41

<210> SEQ ID NO 28
<211> LENGTH: 42
<212> TYPE: DNA
<213> ORGANISM: Artificial
<220> FEATURE:
<223> OTHER INFORMATION: Anabaena variabilis PAL primer to create cysteine to serine substitution at position 565 (forward)

<400> SEQUENCE: 28
cagttcaaga tatcttaccc tccttgcatt aacccgggct gc 42

<210> SEQ ID NO 29
<211> LENGTH: 42
<212> TYPE: DNA
<213> ORGANISM: Artificial
<220> FEATURE:
<223> OTHER INFORMATION: Anabaena variabilis PAL primer to create cysteine to serine substitution at position 565 (reverse)

<400> SEQUENCE: 29
gcagcccggg ttaatgcaag gagggtaaga tatcttgaac tg 42

<210> SEQ ID NO 30
<211> LENGTH: 44
<212> TYPE: DNA
<213> ORGANISM: Artificial
<220> FEATURE:
<223> OTHER INFORMATION: Anabaena variabilis PAL primer to create cysteine to serine substitution at position 64 (forward)

-continued

```
<400> SEQUENCE: 30

gcagggtatt caggcatctt ctgattacat taataatgct gttg                  44


<210> SEQ ID NO 31
<211> LENGTH: 44
<212> TYPE: DNA
<213> ORGANISM: Artificial
<220> FEATURE:
<223> OTHER INFORMATION: Anabaena variabilis PAL primer to create
      cysteine to serine substitution at position 64 (reverse)

<400> SEQUENCE: 31

caacagcatt attaatgtaa tcagaagatg cctgaatacc ctgc                  44


<210> SEQ ID NO 32
<211> LENGTH: 43
<212> TYPE: DNA
<213> ORGANISM: Artificial
<220> FEATURE:
<223> OTHER INFORMATION: Anabaena variabilis PAL primer to create
      cysteine to serine substitution at position 318 (forward)

<400> SEQUENCE: 32

caagatcgtt actcactccg atcccttccc cagtatttgg ggc                   43


<210> SEQ ID NO 33
<211> LENGTH: 43
<212> TYPE: DNA
<213> ORGANISM: Artificial
<220> FEATURE:
<223> OTHER INFORMATION: Anabaena variabilis PAL primer to create
      cysteine to serine substitution at position 318 (reverse)

<400> SEQUENCE: 33

gccccaaata ctggggaagg gatcggagtg agtaacgatc ttg                   43
```